United States Patent
Lee et al.

(10) Patent No.: US 11,980,090 B2
(45) Date of Patent: May 7, 2024

(54) COMPOUND AND ORGANIC LIGHT EMITTING DEVICE COMPRISING THE SAME

(71) Applicant: LG CHEM, LTD., Seoul (KR)

(72) Inventors: Jae Tak Lee, Daejeon (KR); Sung Kil Hong, Daejeon (KR); Jungoh Huh, Daejeon (KR); Dong Uk Heo, Daejeon (KR); Miyeon Han, Daejeon (KR); Junghoon Yang, Daejeon (KR)

(73) Assignee: LG CHEM, LTD., Seoul (KR)

( * ) Notice: Subject to any disclaimer, the term of this patent is extended or adjusted under 35 U.S.C. 154(b) by 627 days.

(21) Appl. No.: 17/262,114

(22) PCT Filed: Nov. 22, 2019

(86) PCT No.: PCT/KR2019/016170
§ 371 (c)(1),
(2) Date: Jan. 21, 2021

(87) PCT Pub. No.: WO2020/106108
PCT Pub. Date: May 28, 2020

(65) Prior Publication Data
US 2021/0313518 A1    Oct. 7, 2021

(30) Foreign Application Priority Data

Nov. 23, 2018 (KR) .................. 10-2018-0146587
Nov. 21, 2019 (KR) .................. 10-2019-0150704

(51) Int. Cl.
*H10K 85/60* (2023.01)
*C07D 405/04* (2006.01)
(Continued)

(52) U.S. Cl.
CPC ......... *H10K 85/654* (2023.02); *C07D 405/04* (2013.01); *C07D 405/10* (2013.01);
(Continued)

(58) Field of Classification Search
CPC ............ H10K 85/654; H10K 85/6574; H10K 85/6576; H10K 85/6572; C07D 405/04;
(Continued)

(56) References Cited

U.S. PATENT DOCUMENTS 10,745,362 B2 *  8/2020  Jung .................... C07D 251/24
10,822,330 B2 * 11/2020  Cha ........................ H10K 99/00
(Continued)

FOREIGN PATENT DOCUMENTS

CN    104066739 A       9/2014
CN    105481811 A   *   4/2016
(Continued)

OTHER PUBLICATIONS

Machine translation of KR 2018-0060619 (no date).*
Machine translation of CN 105481811 (no date).*
Translation of WO written opinion (no date).*

*Primary Examiner* — Amanda C. Walke
(74) *Attorney, Agent, or Firm* — BRYAN CAVE LEIGHTON PAISNER LLP

(57) ABSTRACT

A novel compound represented by the following Chemical Formula 1, and an organic light emitting device comprising the same.

(Continued)

Chemical Formula 1

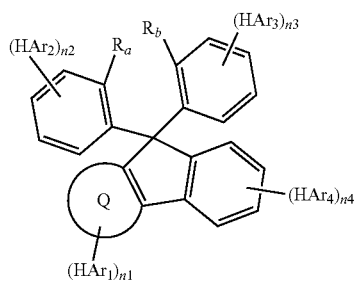

16 Claims, 1 Drawing Sheet

(51) Int. Cl.
  *C07D 405/10*   (2006.01)
  *C07D 409/04*   (2006.01)
  *C07D 409/10*   (2006.01)
  *C07D 409/14*   (2006.01)
  *H10K 50/16*    (2023.01)

(52) U.S. Cl.
  CPC ......... *C07D 409/04* (2013.01); *C07D 409/10* (2013.01); *C07D 409/14* (2013.01); *H10K 85/6572* (2023.02); *H10K 85/6574* (2023.02); *H10K 85/6576* (2023.02); *H10K 50/16* (2023.02)

(58) Field of Classification Search
  CPC .. C07D 405/10; C07D 409/04; C07D 409/10; C07D 409/14
  See application file for complete search history.

(56) References Cited

U.S. PATENT DOCUMENTS

| | | | |
|---|---|---|---|
| 10,873,035 B2 * | 12/2020 | Cha | ............ H10K 85/622 |
| 11,121,329 B2 * | 9/2021 | Uno | ............ C09K 11/06 |
| 2004/0251816 A1 | 12/2004 | Leo et al. | |
| 2014/0225040 A1 | 8/2014 | Parham et al. | |
| 2014/0357866 A1 | 12/2014 | Kim et al. | |
| 2015/0349270 A1 | 12/2015 | Lee et al. | |
| 2016/0329506 A1 | 11/2016 | Lee et al. | |
| 2017/0207397 A1 * | 7/2017 | Lee | ............ C07D 209/86 |
| 2018/0006237 A1 | 1/2018 | Anémain et al. | |
| 2018/0040834 A1 * | 2/2018 | Choi | ............ H10K 85/6574 |
| 2018/0127385 A1 | 5/2018 | Jung et al. | |
| 2020/0123138 A1 | 4/2020 | Cha et al. | |
| 2021/0280794 A1 * | 9/2021 | Heo | ............ C07D 409/04 |

FOREIGN PATENT DOCUMENTS

| | | | | |
|---|---|---|---|---|
| CN | 105899501 A | | 8/2016 | |
| CN | 107108578 A | | 8/2017 | |
| CN | 107325036 A | * | 11/2017 | |
| CN | 107635973 A | | 1/2018 | |
| EP | 3503240 A1 | * | 6/2019 | ......... C07D 405/04 |
| KR | 10-2000-0051826 A | | 8/2000 | |
| KR | 10-1429035 B1 | | 8/2014 | |
| KR | 10-2014-0145456 A | | 12/2014 | |
| KR | 10-2016-0134571 A | | 11/2016 | |
| KR | 10-2017-0100452 A | | 9/2017 | |
| KR | 10-2017-0110641 A | | 10/2017 | |
| KR | 10-2018-0060619 A | | 6/2018 | |
| KR | 2018086126 A | * | 7/2018 | ......... C07D 251/24 |
| KR | 10-2019-0010500 A | | 1/2019 | |
| KR | 10-2136381 B1 | | 7/2020 | |
| WO | 2003-012890 A2 | | 2/2003 | |
| WO | 2013-017189 A1 | | 2/2013 | |
| WO | 2014-185751 A1 | | 11/2014 | |
| WO | 2014-200148 A1 | | 12/2014 | |
| WO | 2017-146522 A1 | | 8/2017 | |

* cited by examiner

【FIG. 1】
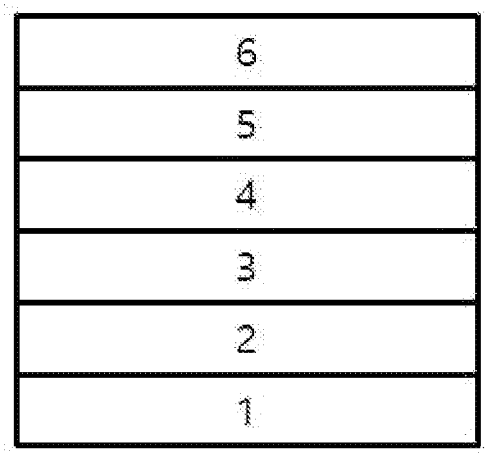
【FIG. 2】
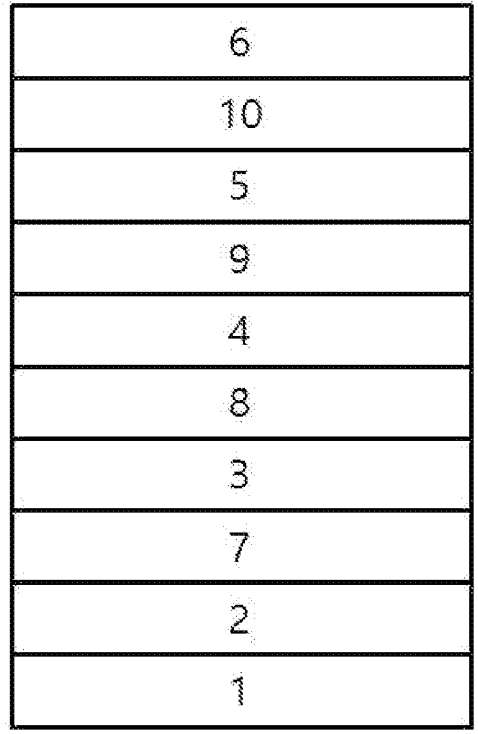

COMPOUND AND ORGANIC LIGHT EMITTING DEVICE COMPRISING THE SAME

CROSS-REFERENCE TO RELATED APPLICATION(S)

This application is a National Stage Application of International Application No. PCT/KR2019/016170 filed on Nov. 22, 2019, which claims the benefit of Korean Patent Application No. 10-2018-0146587 filed on Nov. 23, 2018 and Korean Patent Application No. 10-2019-0150704 filed on Nov. 21, 2019 in the Korean Intellectual Property Office, the disclosures of which are incorporated herein by reference in their entirety.

TECHNICAL FIELD

The present disclosure relates to a novel compound and an organic light emitting device comprising the same.

BACKGROUND

In general, an organic light emitting phenomenon refers to a phenomenon where electric energy is converted into light energy by using an organic material. The organic light emitting device using the organic light emitting phenomenon has characteristics such as a wide viewing angle, an excellent contrast, a fast response time, an excellent luminance, driving voltage and response speed, and thus many studies have proceeded.

The organic light emitting device generally has a structure which comprises an anode, a cathode, and an organic material layer interposed between the anode and the cathode. The organic material layer frequently has a multilayered structure that comprises different materials in order to enhance efficiency and stability of the organic light emitting device, and for example, the organic material layer may be formed of a hole injection layer, a hole transport layer, a light emitting layer, an electron transport layer, an electron injection layer and the like. In the structure of the organic light emitting device, if a voltage is applied between two electrodes, the holes are injected from an anode into the organic material layer and the electrons are injected from the cathode into the organic material layer, and when the injected holes and electrons meet each other, an exciton is formed, and light is emitted when the exciton falls to a ground state again.

There is a continuing need for the development of new materials for the organic materials used in the organic light emitting devices as described above.

PRIOR ART LITERATURE (Patent Literature 0001) Korean Patent Application Laid-Open Publication No. 10-2000-0051826

TECHNICAL PROBLEM

It is an object of the present disclosure to provide a novel compound and an organic light emitting device comprising the same.

TECHNICAL SOLUTION

In an aspect of the present disclosure, there is provided a compound represented by the following Chemical Formula 1:

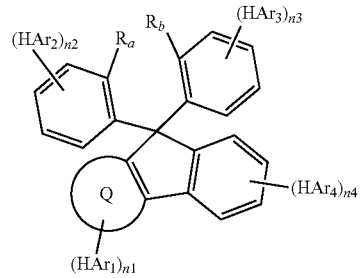

Chemical Formula 1 wherein in Chemical Formula 1,
Q is dibenzofuran, dibenzothiophene, benzofuran, or benzothiophene ring, which is fused with an adjacent pentagonal ring,
$R_a$ and $R_b$ are each hydrogen, or are combined together to form a single bond,
one of $HAr_1$ to $HAr_4$ is the following Chemical Formula 2, another one is the following Chemical Formula 3, and the rest is the following Chemical Formula 2 or 3,

wherein in Chemical Formulas 2 and 3,
$L_1$ and $L_2$ are each independently a single bond; or a substituted or unsubstituted $C_{6-60}$ arylene,
A is a substituted or unsubstituted $C_{2-60}$ heteroaryl containing two or more N atoms,
n1 to n4 are each an integer of 0 to 2,
n1+n2+n3+n4 is an integer of 2 to 8, and
when n1 to n4 are 2 or more, the structures in parentheses are each identical or different.

In another aspect of the present disclosure, there is provided an organic light emitting device comprising: a first electrode; a second electrode that is provided to face the first electrode; and one or more organic material layers that are provided between the first electrode and the second electrode, wherein at least one layer of the organic material layers includes the compound represented by Chemical Formula 1.

ADVANTAGEOUS EFFECTS

The compound represented by Chemical Formula 1 can be used as a material of an organic material layer of an organic light emitting device, and can improve the efficiency, achieve low driving voltage and/or improve lifetime characteristics in the organic light emitting device.

BRIEF DESCRIPTION OF DRAWINGS

FIG. 1 shows an example of an organic light emitting device comprising a substrate 1, an anode 2, a hole transport layer 3, a light emitting layer 4, an electron transport layer 5 and a cathode 6.

FIG. 2 shows an example of an organic light emitting device comprising a substrate 1, an anode 2, a hole injection layer 7, a hole transport layer 3, an electron blocking layer 8, a light emitting layer 4, a hole blocking layer 9, an electron transport layer 5, an electron injection layer 10 and a cathode 6.

DETAILED DESCRIPTION

Hereinafter, embodiments of the present disclosure will be described in more detail to facilitate understanding of the invention.

As used herein, the notation  means a bond linked to another substituent group.

As used herein, the term "substituted or unsubstituted" means being unsubstituted or substituted with one or more substituents selected from the group consisting of deuterium; a halogen group; a cyano group; a nitro group; a hydroxy group; a carbonyl group; an ester group; an imide group; an amino group; a phosphine oxide group; an alkoxy group; an aryloxy group; an alkylthioxy group; an arylthioxy group; an alkylsulfoxy group; an arylsulfoxy group; a silyl group; a boron group; an alkyl group; a cycloalkyl group; an alkenyl group; an aryl group; an aralkyl group; an aralkenyl group; an alkylaryl group; an alkylamine group; an aralkylamine group; a heteroarylamine group; an arylamine group; an arylphosphine group; and a heteroaryl group containing at least one of N, O and S atoms, or being unsubstituted or substituted with a substituent to which two or more substituents of the above-exemplified substituents are connected. For example, "a substituent in which two or more substituents are connected" may be a biphenyl group. Namely, a biphenyl group may be an aryl group, or it may also be interpreted as a substituent in which two phenyl groups are connected.

In the present disclosure, the carbon number of a carbonyl group is not particularly limited, but is preferably 1 to 40. Specifically, the carbonyl group may be a compound having the following structural formulas, but is not limited thereto.

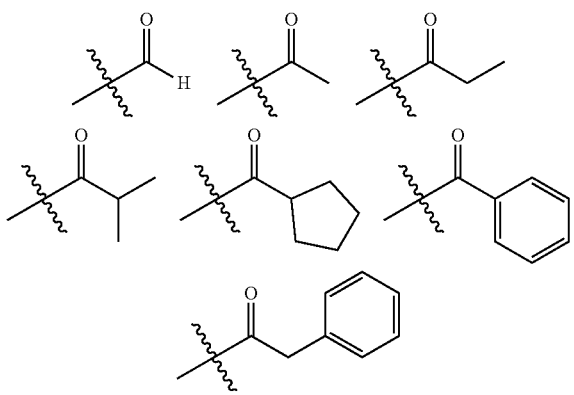

In the present disclosure, an ester group may have a structure in which oxygen of the ester group may be substituted by a straight-chain, branched-chain, or cyclic alkyl group having 1 to 25 carbon atoms, or an aryl group having 6 to 25 carbon atoms. Specifically, the ester group may be a compound having the following structural formulas, but is not limited thereto.

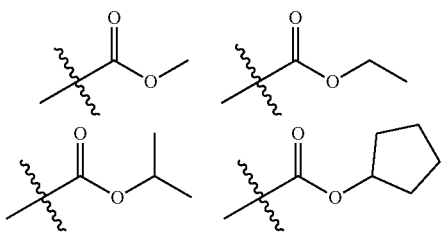

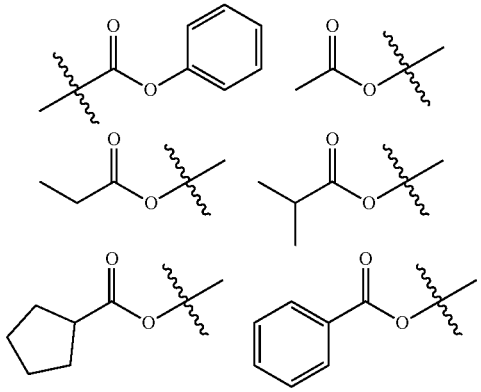

In the present disclosure, the carbon number of an imide group is not particularly limited, but is preferably 1 to 25. Specifically, the imide group may be a compound having the following structural formulas, but is not limited thereto.

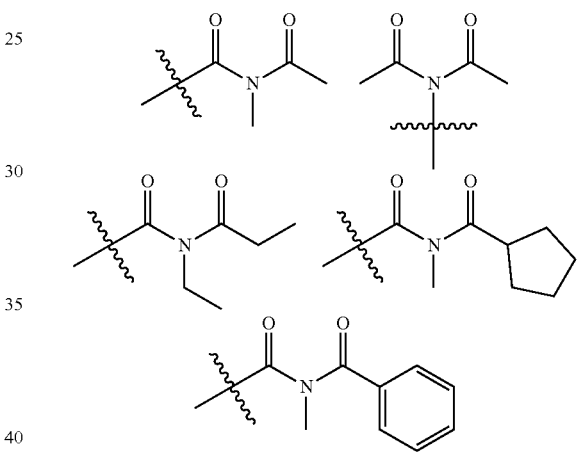

In the present disclosure, a silyl group specifically includes a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group and the like, but is not limited thereto.

In the present disclosure, a boron group specifically includes a trimethylboron group, a triethylboron group, a t-butyldimethylboron group, a triphenylboron group, and a phenylboron group, but is not limited thereto.

In the present disclosure, examples of a halogen group include fluorine, chlorine, bromine, or iodine.

In the present disclosure, the alkyl group may be straight-chain or branched-chain, and the carbon number thereof is not particularly limited, but is preferably 1 to 40. According to one embodiment, the carbon number of the alkyl group is 1 to 20. According to another embodiment, the carbon number of the alkyl group is 1 to 10. According to another embodiment, the carbon number of the alkyl group is 1 to 6. Specific examples of the alkyl group include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethylpropyl, isohexyl, 2-methylpentyl, 4-methylhexyl, 5-methylhexyl, and the like, but are not limited thereto.

In the present disclosure, the alkenyl group may be straight-chain or branched-chain, and the carbon number thereof is not particularly limited, but is preferably 2 to 40. According to one embodiment, the carbon number of the alkenyl group is 2 to 20. According to another embodiment, the carbon number of the alkenyl group is 2 to 10. According to still another embodiment, the carbon number of the alkenyl group is 2 to 6. Specific examples thereof include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, a stilbenyl group, a styrenyl group, and the like, but are not limited thereto.

In the present disclosure, a cycloalkyl group is not particularly limited, but the carbon number thereof is preferably 3 to 60. According to one embodiment, the carbon number of the cycloalkyl group is 3 to 30. According to another embodiment, the carbon number of the cycloalkyl group is 3 to 20. According to still another embodiment, the carbon number of the cycloalkyl group is 3 to 6. Specific examples thereof include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl, and the like, but are not limited thereto.

In the present disclosure, an aryl group is not particularly limited, but the carbon number thereof is preferably 6 to 60, and it may be a monocyclic aryl group or a polycyclic aryl group. According to one embodiment, the carbon number of the aryl group is 6 to 30. According to one embodiment, the carbon number of the aryl group is 6 to 20. The aryl group may be a phenyl group, a biphenyl group, a terphenyl group or the like as the monocyclic aryl group, but is not limited thereto. The polycyclic aryl group includes a naphthyl group, an anthracenyl group, a phenanthryl group, a pyrenyl group, a perylenyl group, a chrysenyl group, flurorenyl group or the like, but is not limited thereto.

In the present disclosure, the fluorenyl group may be substituted, and two substituents may be linked with each other to form a spiro structure. In the case where the fluorenyl group is substituted,

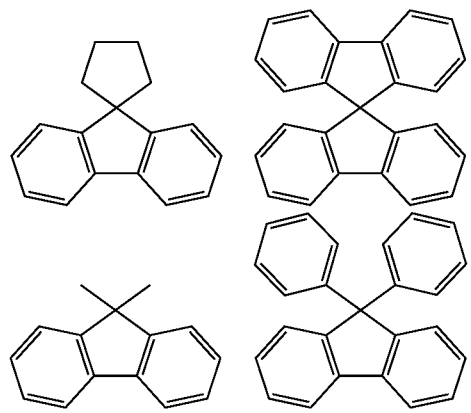

and the like can be formed. However, the structure is not limited thereto.

In the present disclosure, a heteroaryl group is a heteroaryl group containing one or more of O, N, Si and S as a heteroatom, and the carbon number thereof is not particularly limited, but is preferably 2 to 60. Examples of the heteroaryl group include a thiophene group, a furan group, a pyrrole group, an imidazole group, a thiazole group, an oxazol group, an oxadiazol group, a triazol group, a pyridyl group, a bipyridyl group, a pyrimidyl group, a triazine group, an acridyl group, a pyridazine group, a pyrazinyl group, a quinolinyl group, a quinazoline group, a quinoxalinyl group, a phthalazinyl group, a pyridopyrimidinyl group, a pyridopyrazinyl group, a pyrazinopyrazinyl group, an isoquinoline group, an indole group, a carbazole group, a benzoxazole group, a benzoimidazole group, a benzothiazol group, a benzocarbazole group, a benzothiophene group, a dibenzothiophene group, a benzofuranyl group, phenanthroline group, an isoxazolyl group, a thiadiazolyl group, a phenothiazinyl group, a dibenzofuranyl group, and the like, but are not limited thereto.

In the present disclosure, the aryl group in the aralkyl group, the aralkenyl group, the alkylaryl group and the arylamine group is the same as the aforementioned examples of the aryl group. In the present disclosure, the alkyl group in the aralkyl group, the alkylaryl group and the alkylamine group is the same as the aforementioned examples of the alkyl group. In the present disclosure, for the heteroaryl in the heteroarylamine group the aforementioned description of the heteroaryl group can be applied. In the present disclosure, the alkenyl group in the aralkenyl group is the same as the aforementioned examples of the alkenyl group. In the present disclosure, the aforementioned description of the aryl group may be applied except that the arylene is a divalent group. In the present disclosure, the aforementioned description of the heteroaryl group can be applied except that the heteroarylene is a divalent group. In the present disclosure, the aforementioned description of the aryl group or cycloalkyl group can be applied except that the hydrocarbon ring is not a monovalent group but formed by combining two substituent groups. In the present disclosure, the aforementioned description of the heteroaryl group can be applied, except that the heterocyclic group is not a monovalent group but formed by combining two substituent groups.

Meanwhile, one embodiment of the present disclosure provides a compound represented by Chemical Formula 1. The compound represented by Chemical Formula 1 includes a substituent of Chemical Formula 2 and a substituent of Chemical Formula 3 at the same time. In other words, at least one of the substituents $HAr_1$ to $HAr_4$ in Chemical Formula 1 is Chemical Formula 2, and at least one is Chemical Formula 3. Therefore, the sum of n1, n2, n3 and n4, which means the number of respective substituents $HAr_1$, $HAr_2$, $HAr_3$ and $HAr_4$, has a value of 2 or more. In this case, when n1+n2+n3+n4 is 2, it means that one of $HAr_1$ to $HAr_4$ is a substituent of Chemical Formula 2, and the other one is a substituent of Chemical Formula 3.

When the compound represented by Chemical Formula 1 includes two or more N atom-containing heteroaryl groups of Chemical Formula 2 and the cyano group of Chemical Formula 3 at the same time as described above, the action of attracting electrons of the cyano group and the action of transferring electrons of the heteroaryl group containing two or more N atoms are balanced with each other to control the electron transfer rate. Thereby, the organic light emitting device using the same exhibits excellent characteristics in terms of driving voltage, efficiency, and lifetime as compared with the organic light emitting device using a compound that does not include such substituents or contains only one substituent.

Specifically, depending on the definition of $R_a$ and $R_b$, the compound represented by Chemical Formula 1 is represented by the following Chemical Formula 1A when $R_a$ and $R_b$ are each hydrogen, and it is represented by the following Chemical Formula 1B when $R_a$ and $R_b$ are combined together to form a single bond:

Chemical Formula 1A

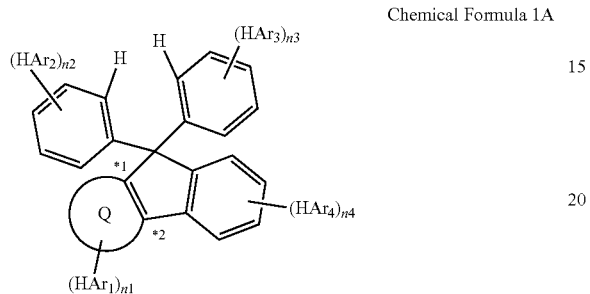

Chemical Formula 1B

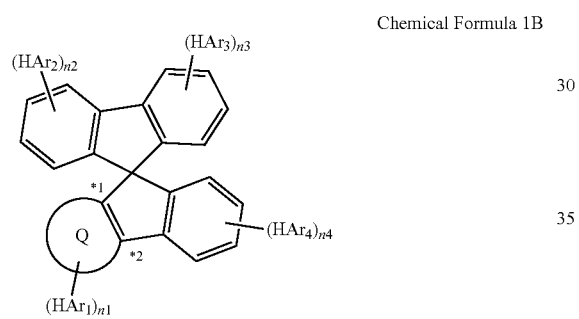

wherein in Chemical Formulas 1A and 1B,

Q is any one selected from the group consisting of:

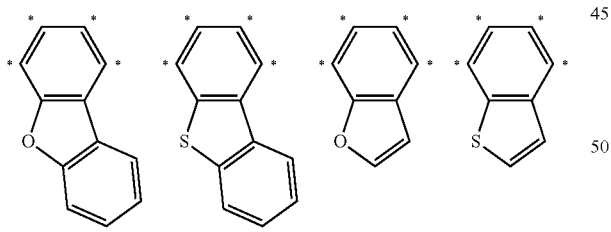

wherein, two adjacent carbon atoms of * are respectively condensed with carbon atoms of *1 and *2 of Chemical Formula 1A or 1B to form a ring, and $HAr_1$ to $HAr_4$ and n1 to n4 are the same as defined in Chemical Formula 1.

Also, depending on the bonding position of Q, the compound represented by Chemical Formula 1 is represented by any one of the following Chemical Formulas 1-1 to 1-6 when Q is dibenzofuran or dibenzothiophene, and it is represented by any one of the following Chemical Formulas 1-7 to 1-12 when Q is benzofuran or benzothiophene.

1-1

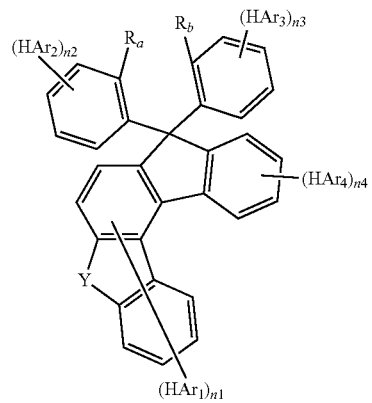

1-2

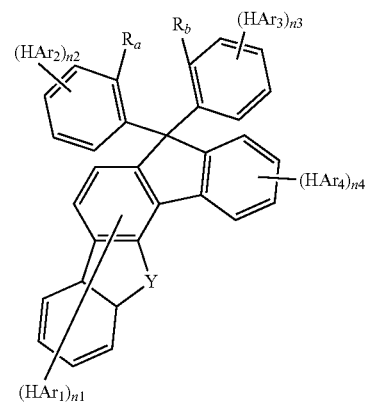

1-3

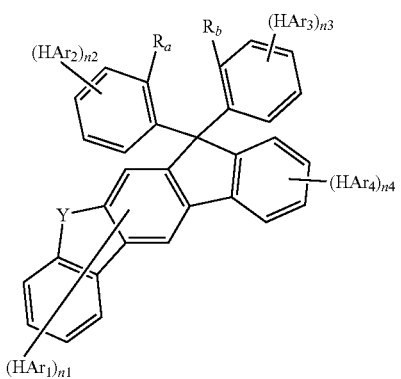

1-4

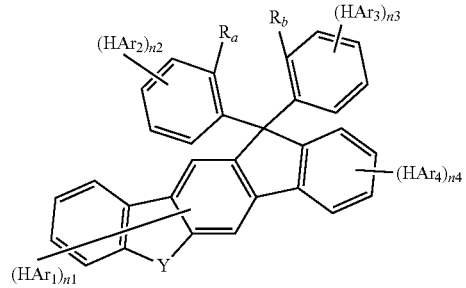

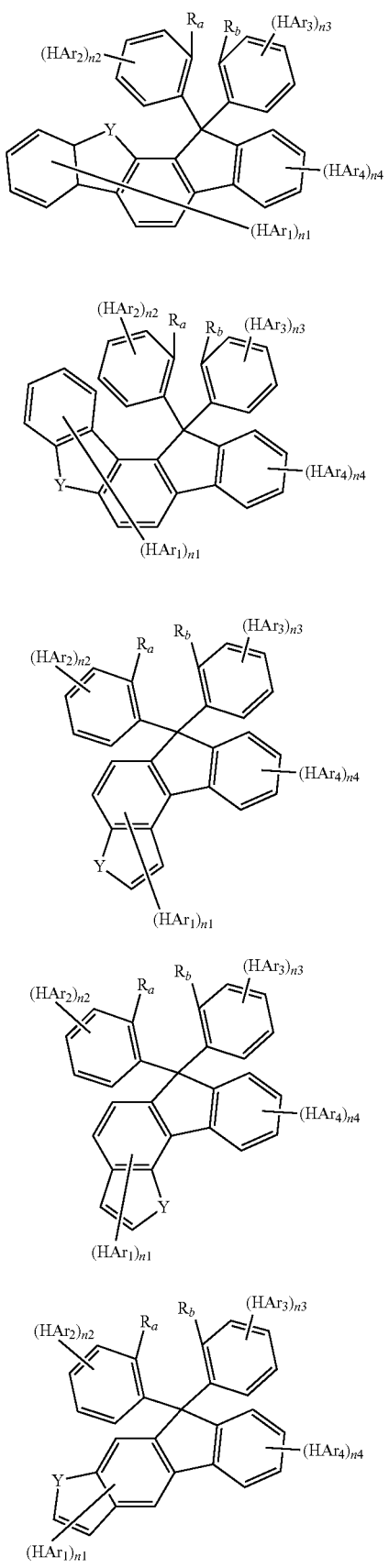
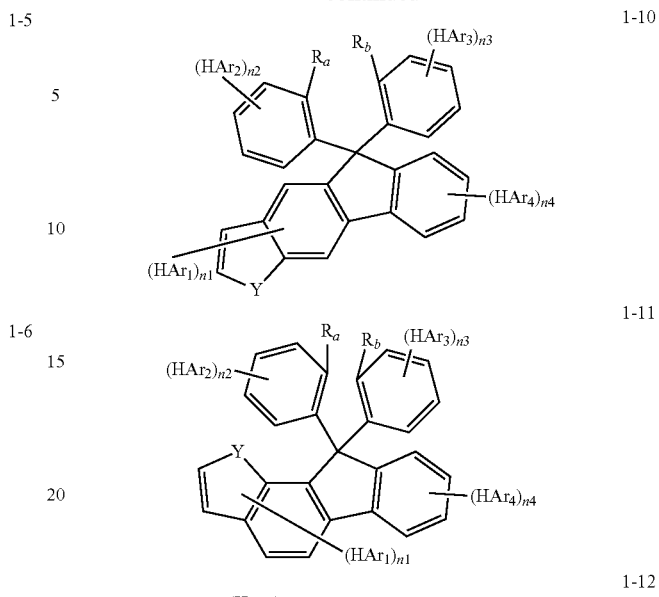
wherein in Chemical Formulas 1-1 to 1-12,
Y is O or S, and
$R_a$, $R_b$, $HAr_1$ to $HAr_4$ and n1 to n4 are the same as defined in Chemical Formula 1.
Preferably, the substituent of Chemical Formula 2 may be any one of the following Chemical Formulas 2-1 to 2-3:
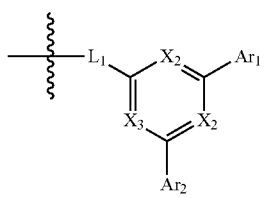
[Formula 2-1]
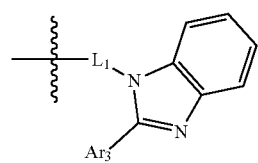
[Formula 2-2]
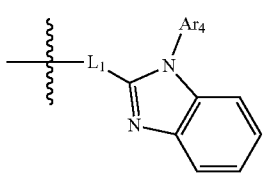
[Formula 2-3]
wherein in Chemical Formulas 2-1 to 2-3,
$X_1$ to $X_3$ are each independently N or CH, and at least two of $X_1$ to $X_3$ are N, $Ar_1$ to $Ar_4$ are each independently hydrogen; deuterium; a substituted or unsubstituted $C_{1-60}$ alkyl; a substituted or unsubstituted $C_{3-60}$ cycloalkyl; a substituted or unsubstituted $C_{6-60}$ aryl; or a substituted or unsubstituted $C_{2-60}$ heteroaryl containing one or more heteroatoms selected from the group consisting of N, O and S, and $L_1$ is the same as defined in Chemical Formula 1.

More preferably, in Chemical Formula 2-1, $X_1$ to $X_3$ are N.

More preferably, in Chemical Formulas 2-1 to 2-3, $Ar_1$ to $Ar_4$ are each independently $C_1$-10 alkyl, or $C_{6-20}$ aryl. Most preferably, in Chemical Formulas 2-1 to 2-3, $Ar_1$ and $Ar_2$ are phenyl, $Ar_3$ is ethyl, and $Ar_4$ is phenyl.

Preferably, in Chemical Formulas 2 and 3, $L_1$ and $L_2$ are each independently a single bond, or $C_{6-20}$ arylene, more preferably a single bond, or phenylene, most preferably a single bond, or 1,4-phenylene.

Preferably, the compound represented by Chemical Formula 1 is a compound represented by Chemical Formula 1-1 or 1-7.

Specifically, the compound represented by Chemical Formula 1 may be represented by any one of the following Chemical Formulas 4-1 to 4-4:

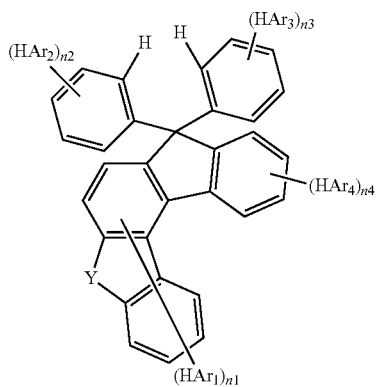

Chemical Formula 4-1

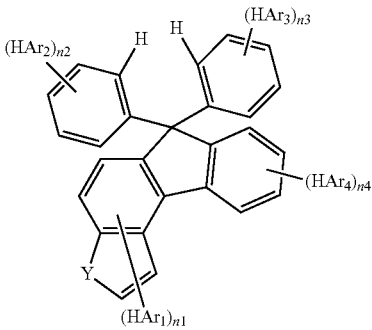

Chemical Formula 4-2

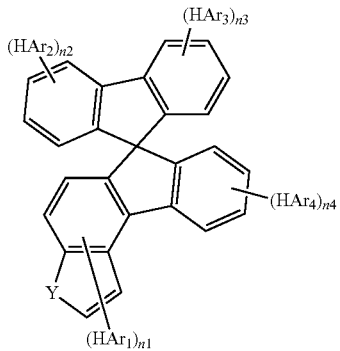

Chemical Formula 4-3

Chemical Formula 4-4

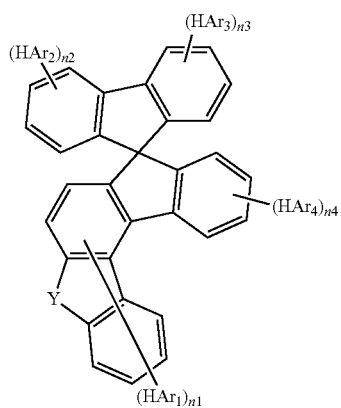

wherein in Chemical Formulas 4-1 to 4-4,

Y is O or S, n1 to n4 are each 0 or 1, n1+n2+n3+n4 is 2, one of $HAr_1$ to $HAr_4$ is Chemical Formula 2, and the other one is Chemical Formula 3.

Meanwhile, n1+n2+n3+n4 may be 2 or 3.

Specifically, n1 is 1, and n2, n3 and n4 are each 0 or 1.

More specifically, n1 and n2 are each 1, and n3 and n4 are each 0;

or n1 and n3 are each 1, and n2 and n4 are each 0; or n1 and n4 may be each 1, and n2 and n3 may be each 0.

For example, the compound represented by Chemical Formula 1 may be represented by the following Chemical Formula 5-1 or 5-2:

Chemical Formula 5-1

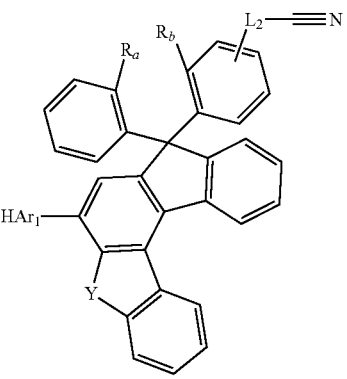

Chemical Formula 5-2

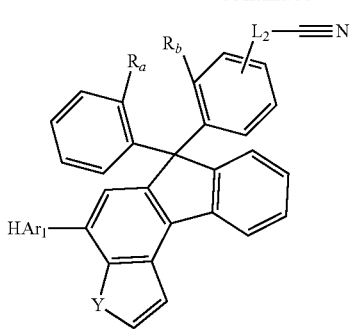

wherein in Chemical Formulas 5-1 and 5-2,
$R_a$ and $R_b$ are each hydrogen, or are combined together to form a single bond,
Y is O or S,
$HAr_1$ is Chemical Formula 2, and
$L_2$ is a single bond or 1,4-phenylene.
Alternatively, the compound represented by Chemical Formula 1 may be represented by the following Chemical Formula 5-3 or 5-4:

Chemical Formula 5-3

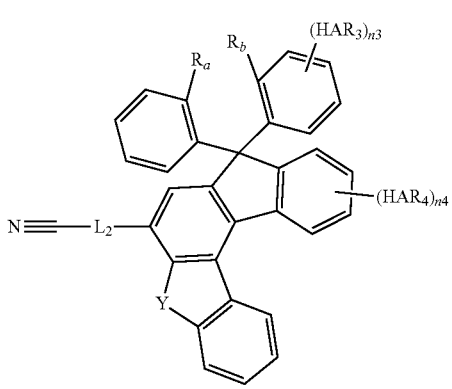

Chemical Formula 5-4

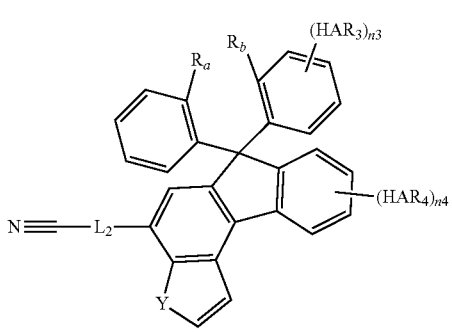

wherein in Chemical Formulas 5-3 and 5-4,
$R_a$ and $R_b$ are each hydrogen, or are combined together to form a single bond,
Y is O or S,
$L_2$ is a single bond or 1,4-phenylene.
n3 and n4 are each 0 or 1,
n3+n4 is 1, and
one of $HAr_3$ and $HAr_4$ is Chemical Formula 2.
Alternatively, the compound represented by Chemical Formula 1 may be represented by the following Chemical Formula 5-5 or 5-6:

Chemical Formula 5-5

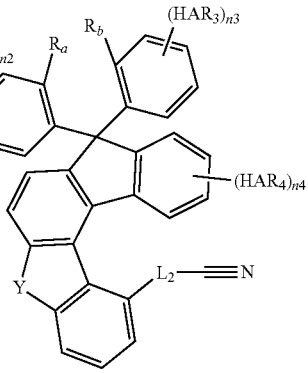

Chemical Formula 5-6

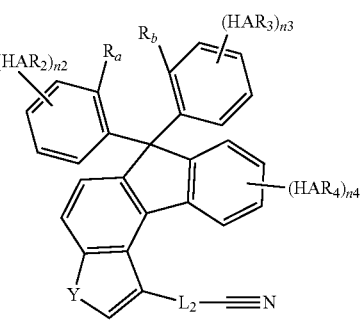

wherein in Chemical Formulas 5-5 and 5-6,
$R_a$ and $R_b$ are each hydrogen, or are combined together to form a single bond,
Y is O or S,
$L_2$ is a single bond or 1,4-phenylene.
n2 to n4 are each 0 or 1,
n2+n3+n4 is 1, and
one of $HAr_2$ to $HAr_4$ is Chemical Formula 2.
Alternatively, n1, n2 and n3 are each 1, and n4 is 0; or
n1, n2 and n4 are each 1, and n3 is 0; or
n1, n3 and n4 are each 1, and n2 is 0; or
n2, n3 and n4 are each 1, and n1 is 0; or
n1 is 2, n2 is 1, and n3 and n4 are each 0; or
n1 is 2, n3 is 1, and n2 and n4 are each 0; or
n1 is 2, n4 is 1, and n2 and n3 may each be 0.
For example, the compound may be represented by the following Chemical Formula 6-1 or 6-2:

Chemical Formula 6-1

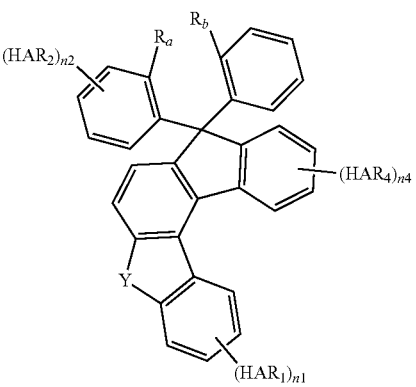

Chemical Formula 6-2

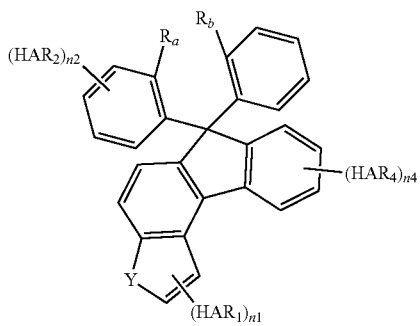

wherein in Chemical Formulas 6-1 and 6-2, $R_a$ and $R_b$ are each hydrogen, or are combined together to form a single bond, Y is O or S, n1, n2 and n4 are each 0, 1, or 2, n1+n2+n4 is 2, one of $HAr_1$, $HAr_2$, and $HAr_4$ is Chemical Formula 2, and another one is Chemical Formula 3, and the rest is Chemical Formula 2 or 3.

Alternatively, the compound may be represented by the following Chemical Formula 6-3 or 6-4:

Chemical Formula 6-3

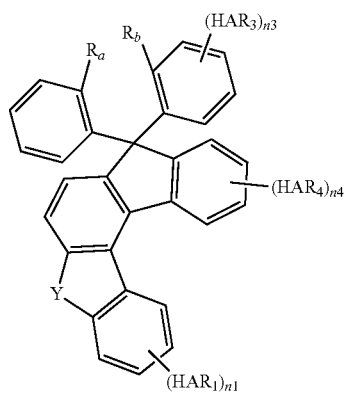

Chemical Formula 6-4

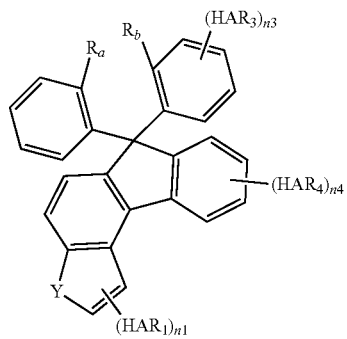

wherein in Chemical Formulas 6-3 and 6-4, $R_a$ and $R_b$ are each hydrogen, or are combined together to form a single bond, Y is O or S, n1, n3 and n4 are each 0, 1, or 2, n1+n3+n4 is 2, and one of $HAr_1$, $HAr_3$, and $HAr_4$ is Chemical Formula 2, and another one is Chemical Formula 3, and the rest is Chemical Formula 2 or 3.

Specifically, for example, the compound may be any one selected from the group consisting of the following compounds:

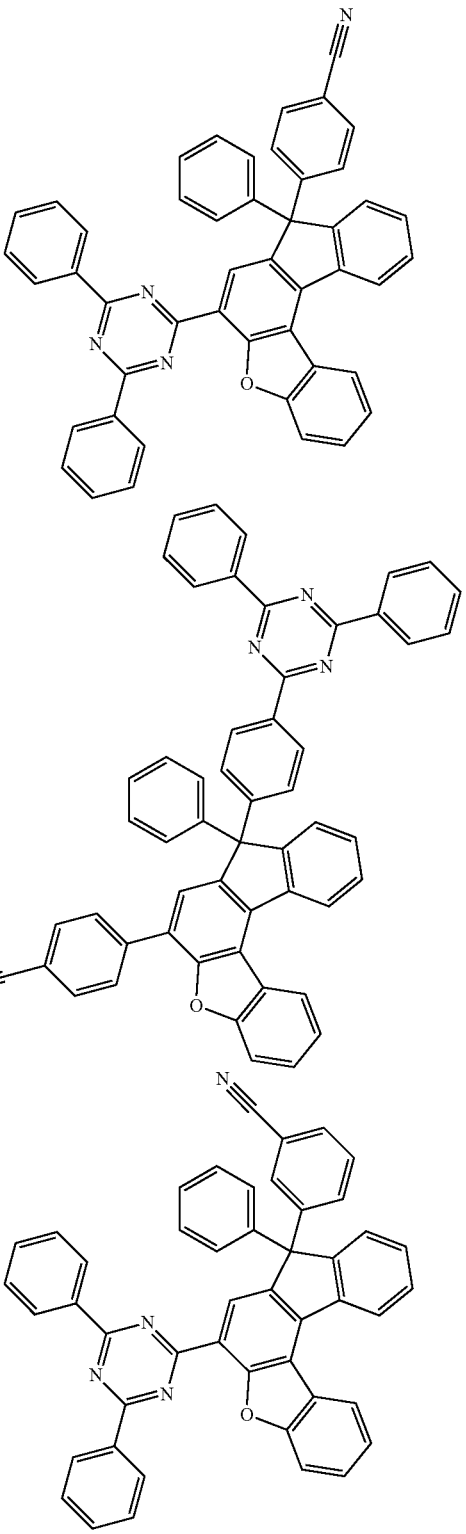

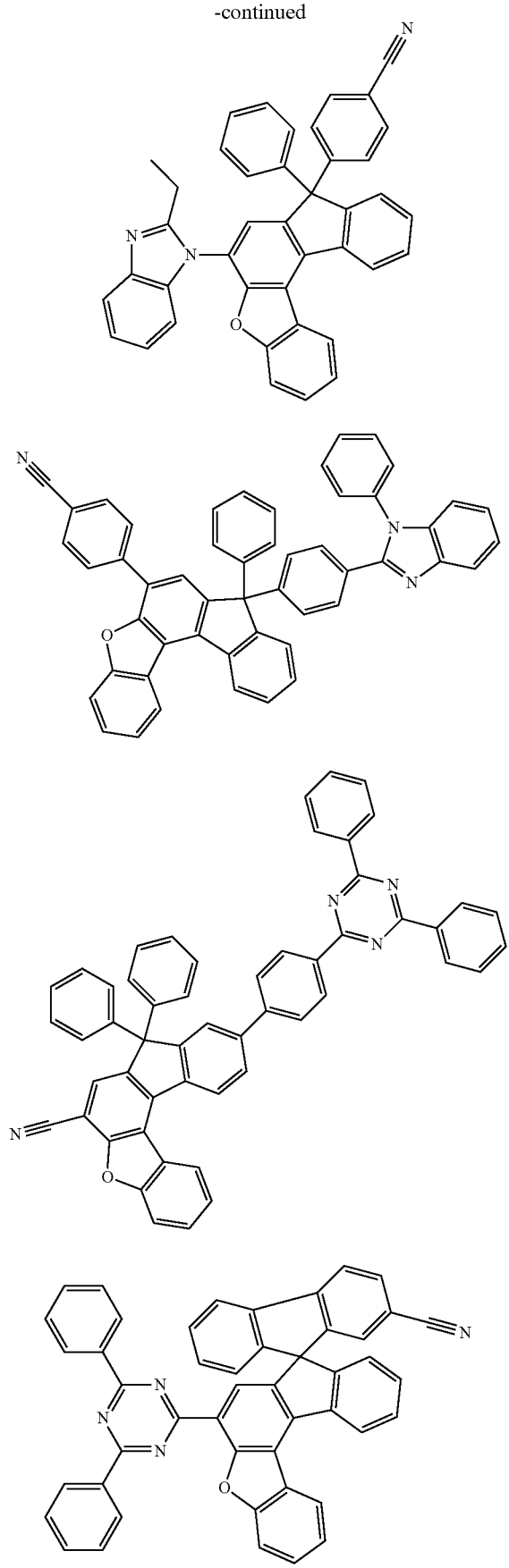
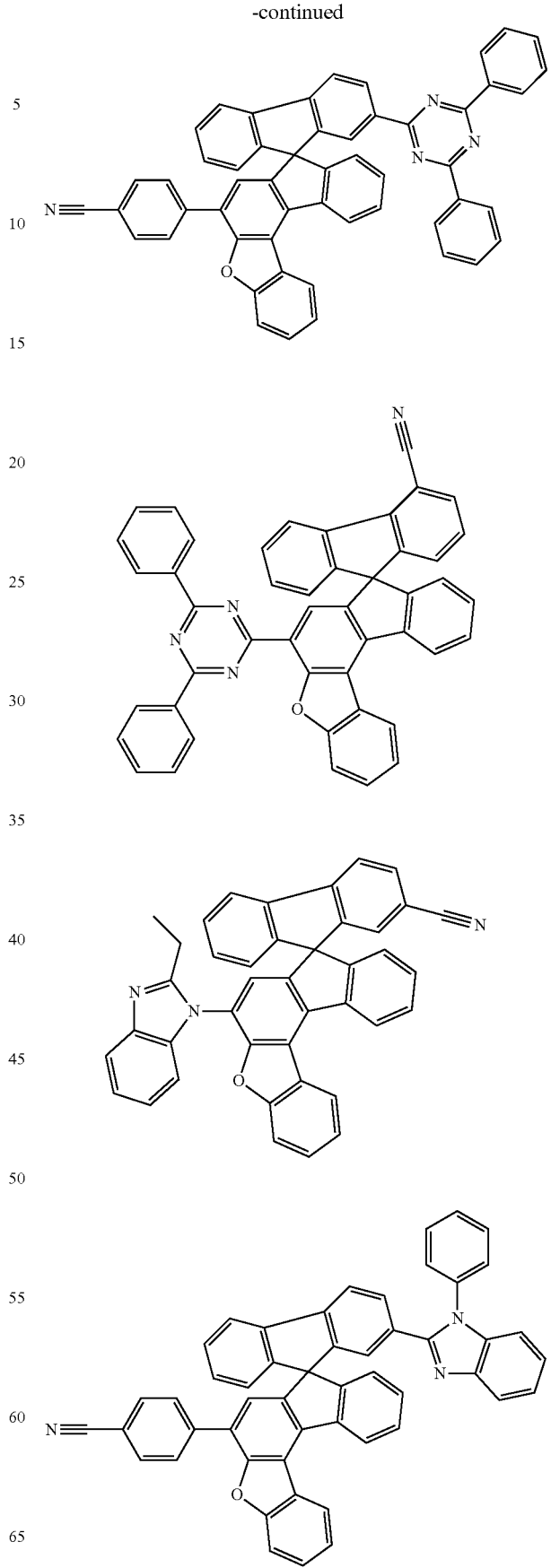

-continued
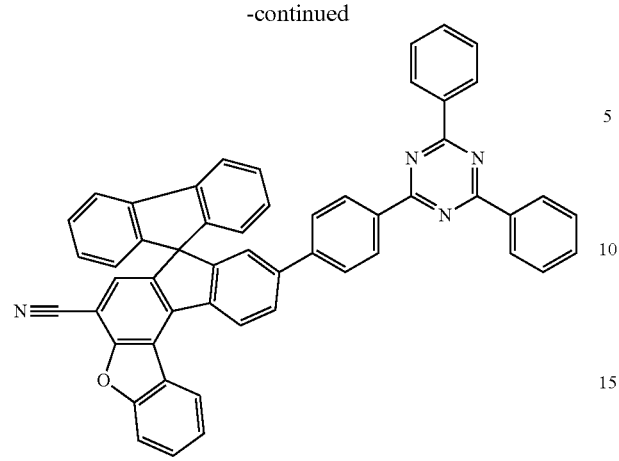
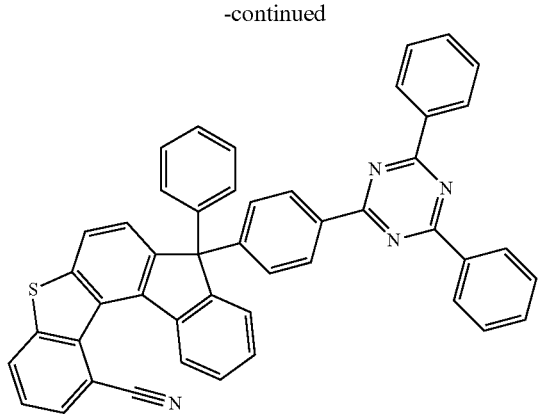
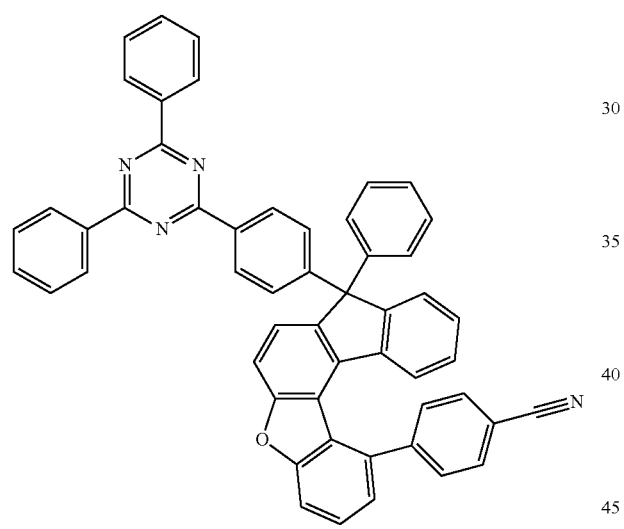
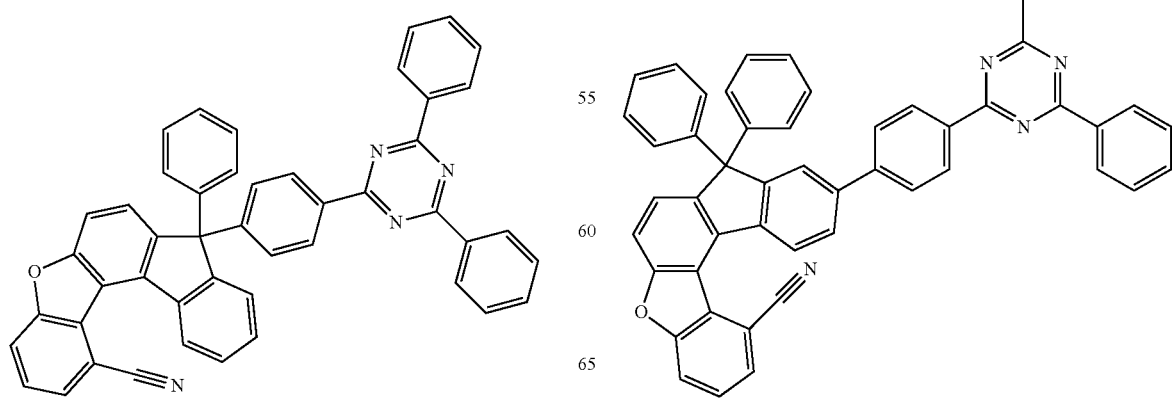

21
-continued
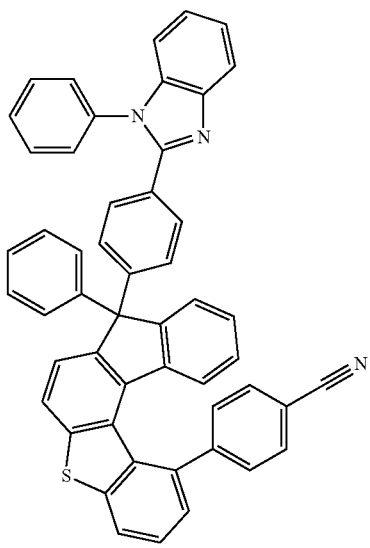
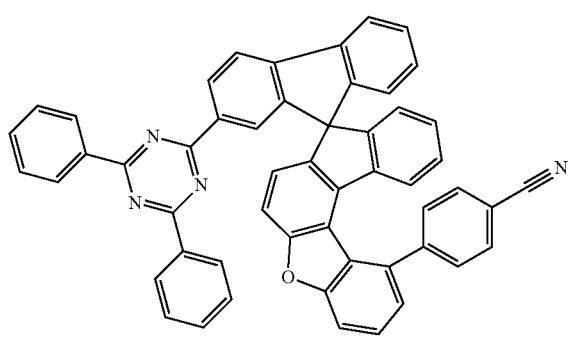
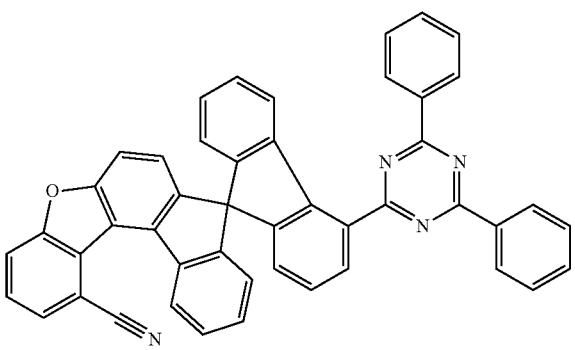
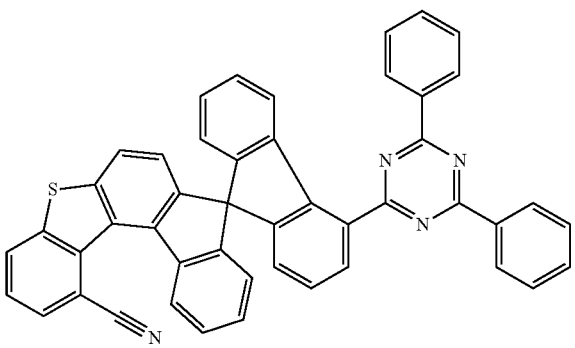
22
-continued
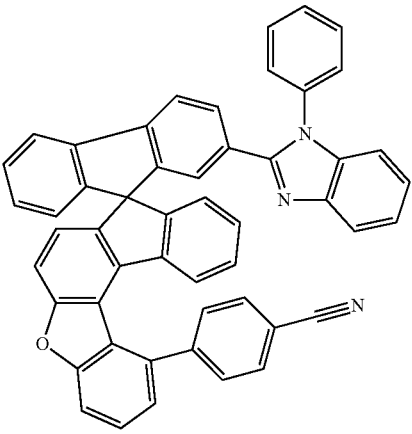
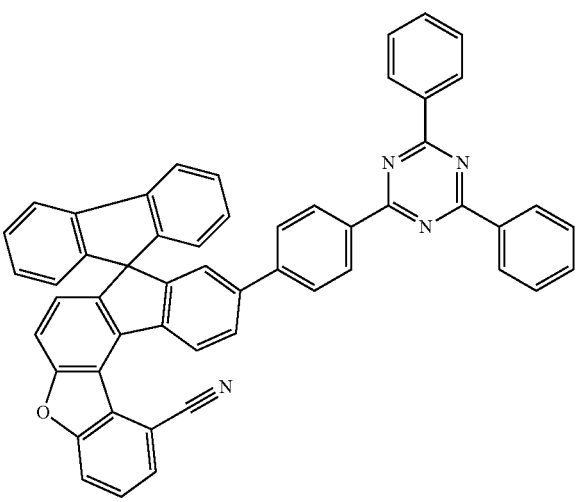
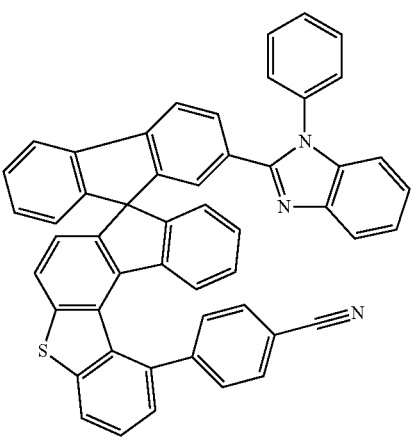

23
-continued
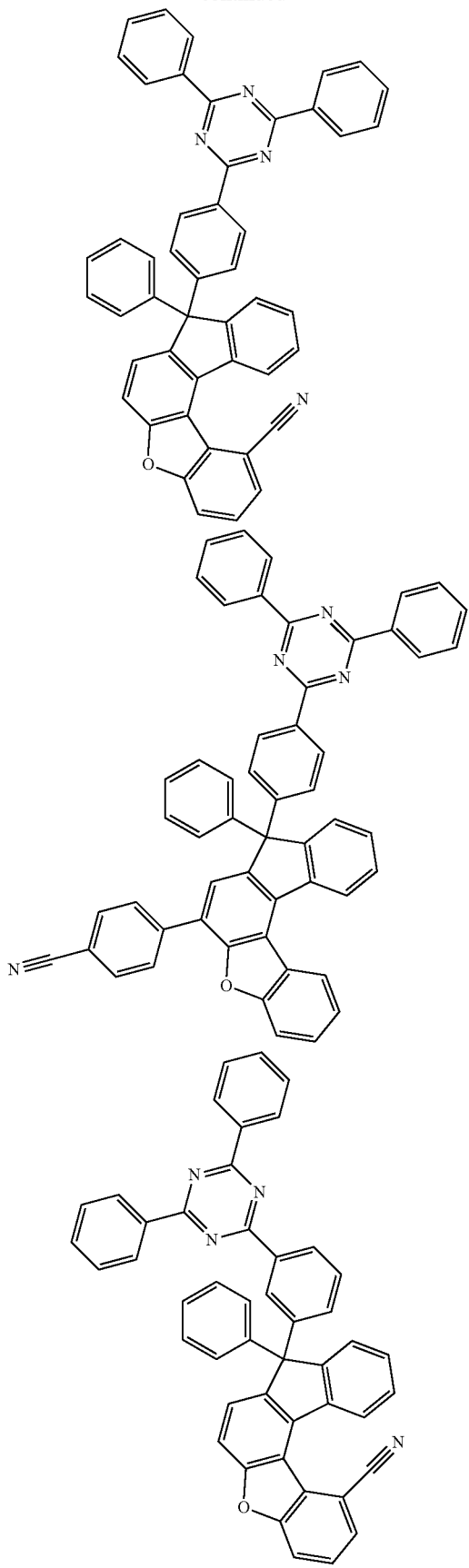
24
-continued
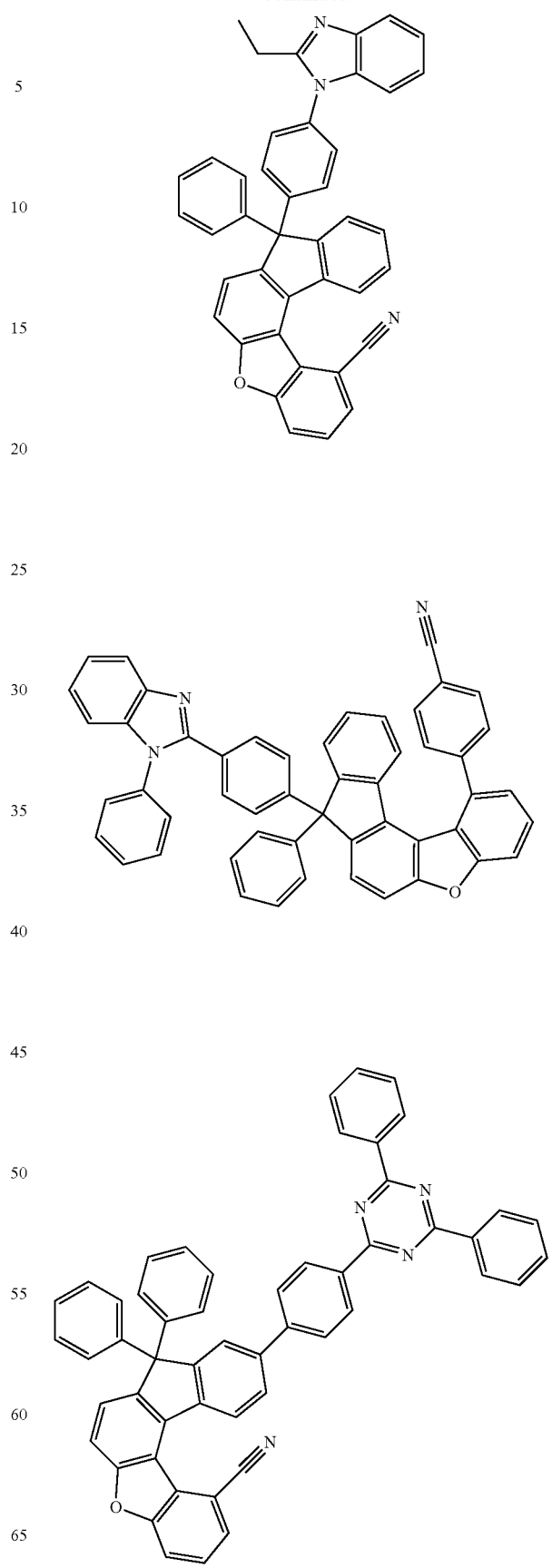

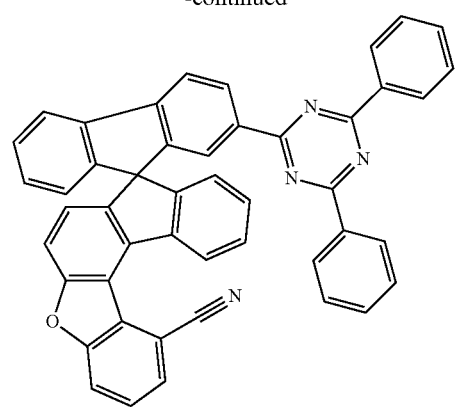
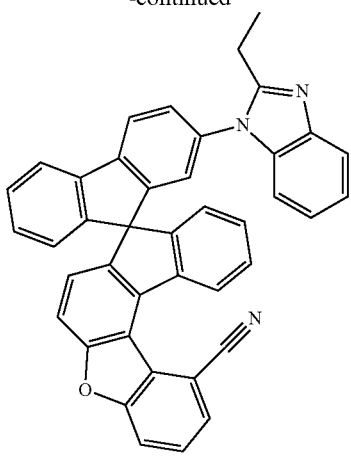
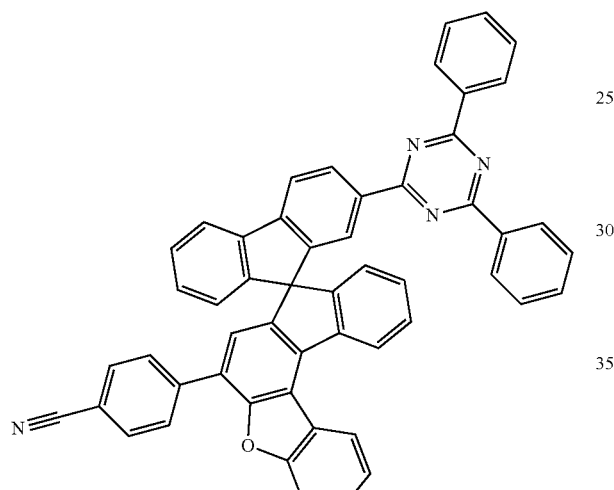
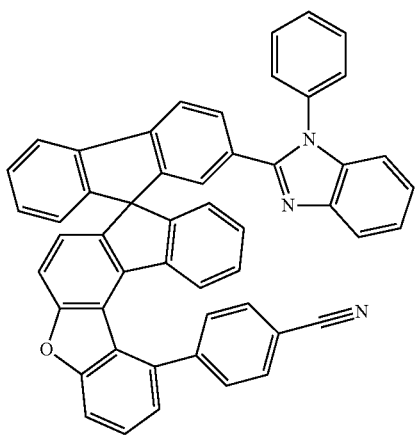
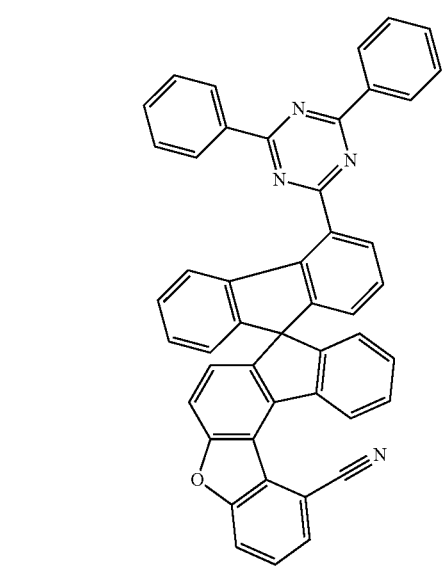
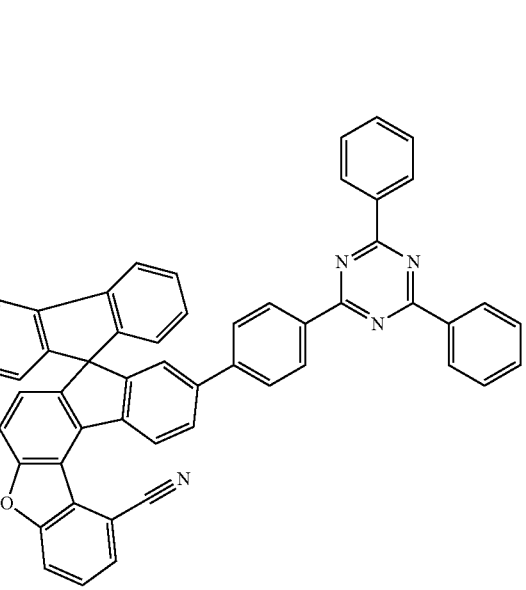

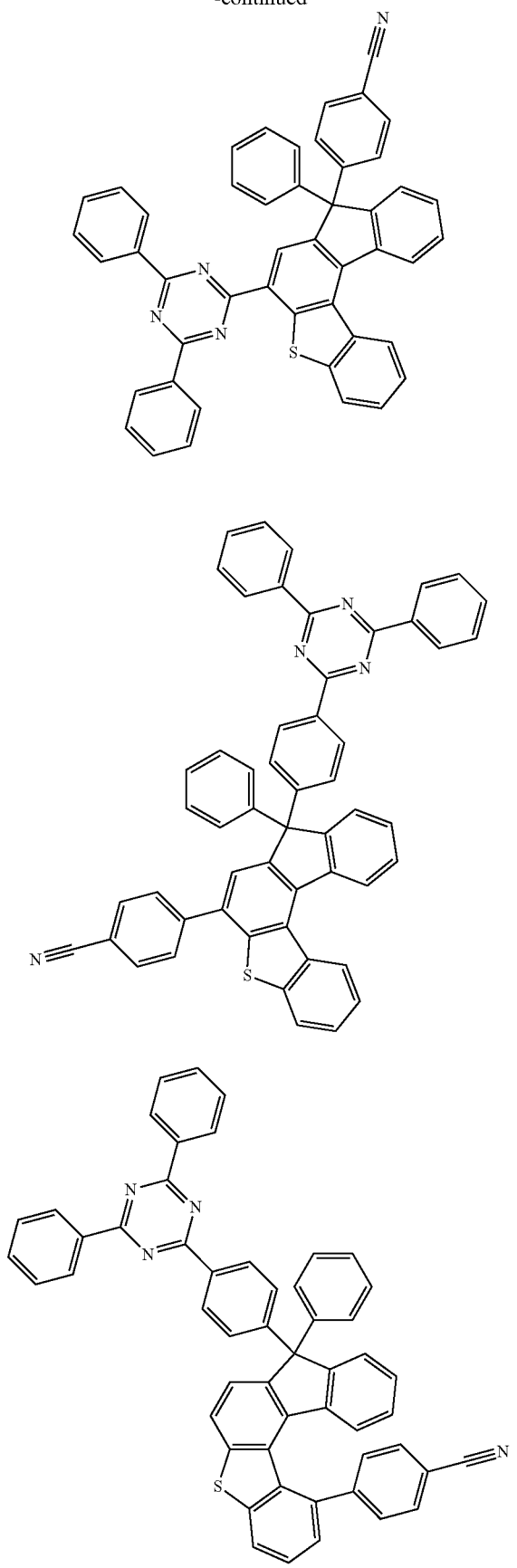
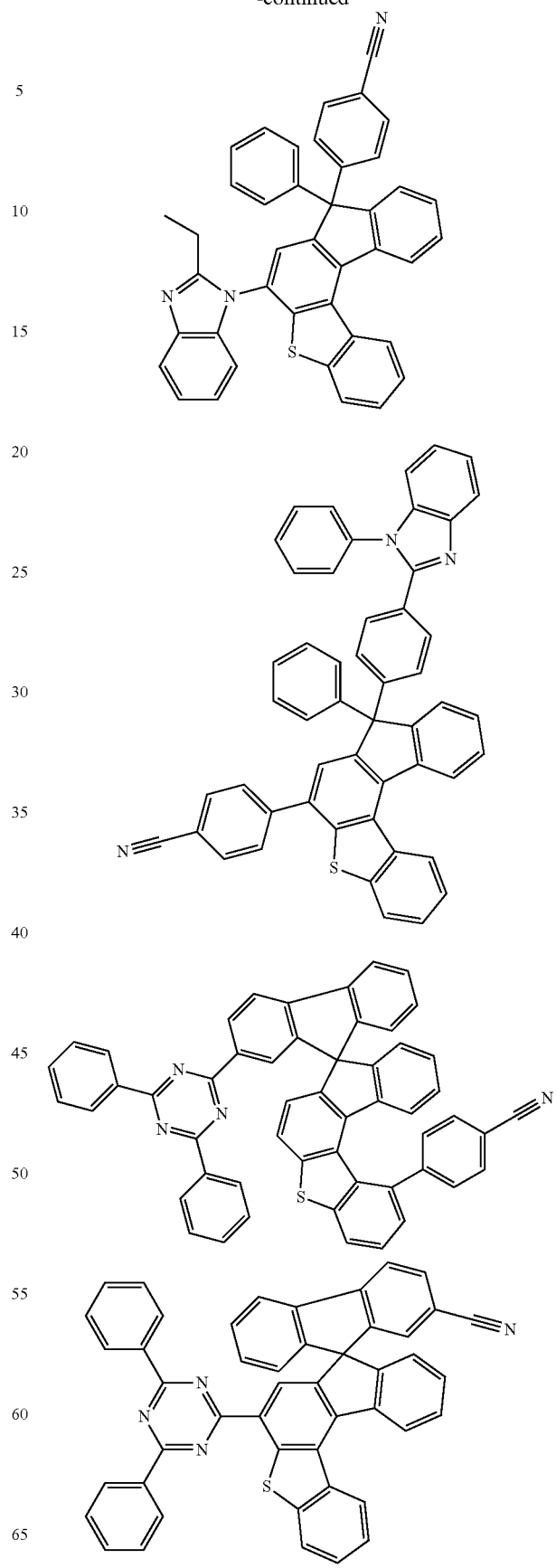

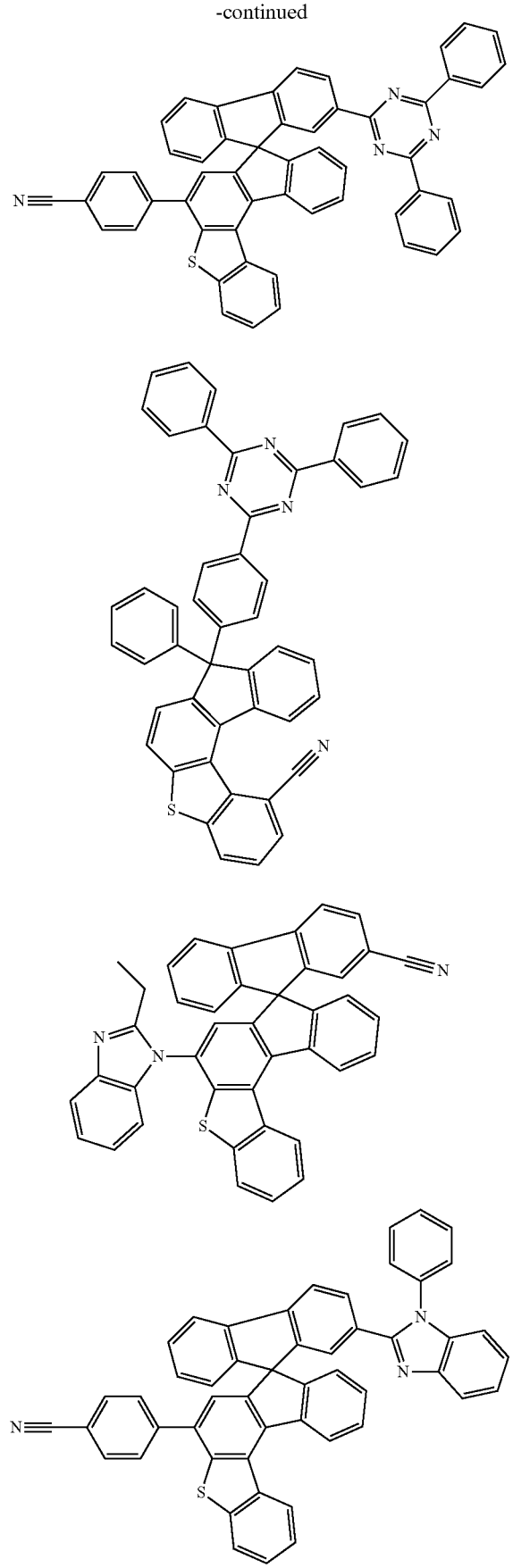
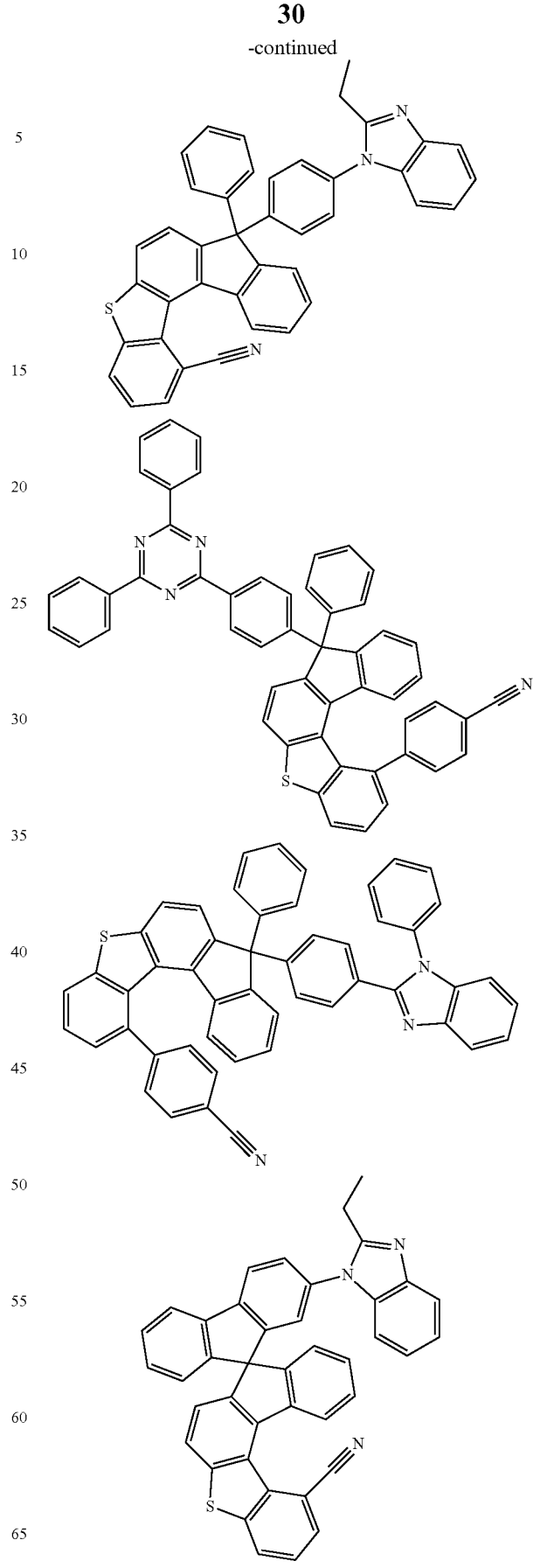

31
-continued
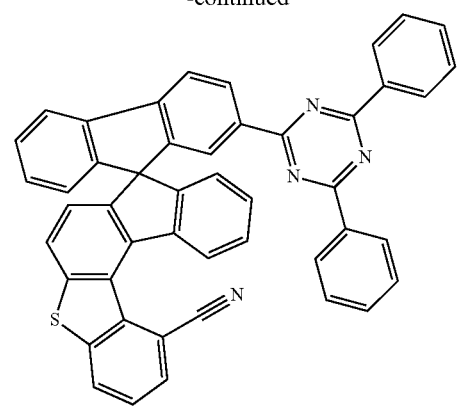
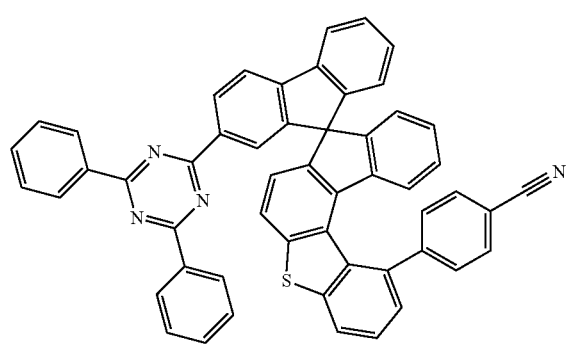
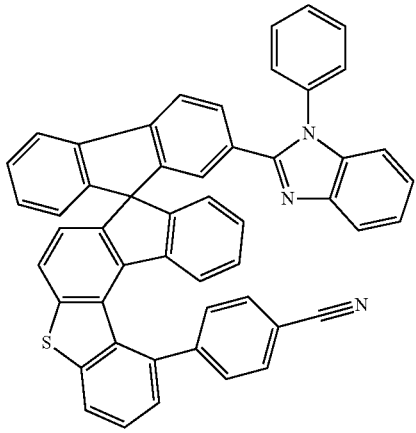
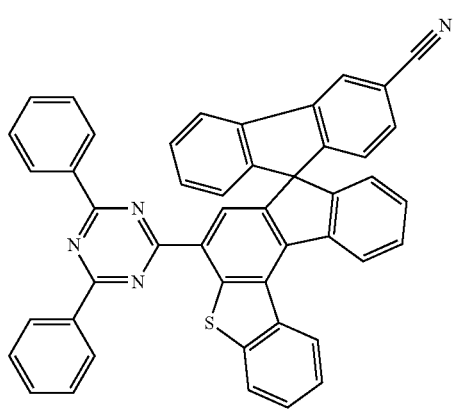
32
-continued
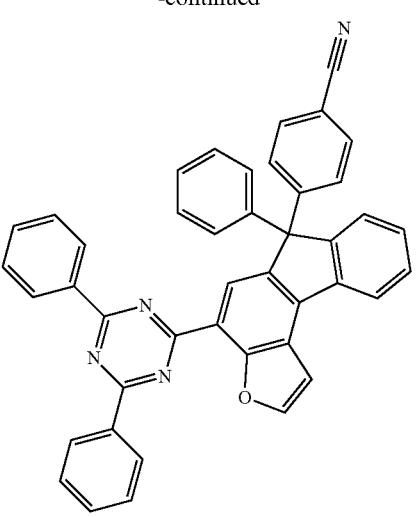
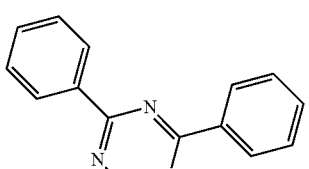
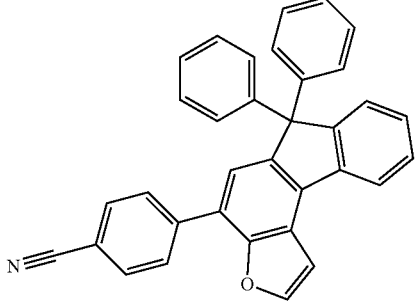
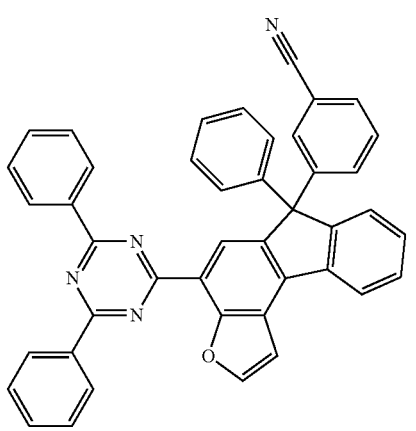

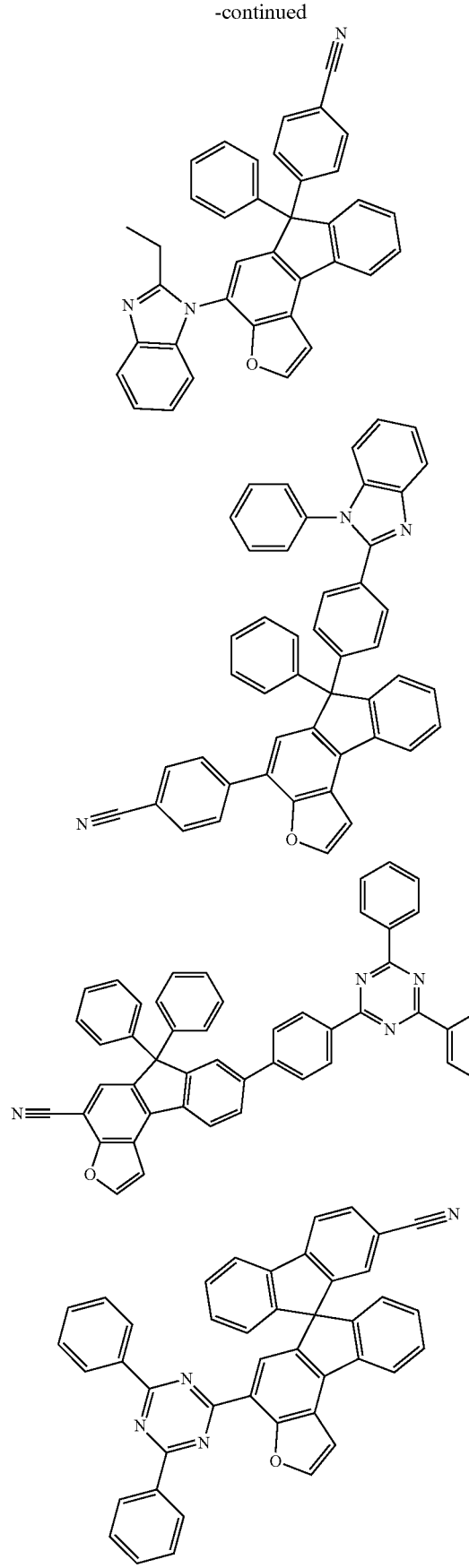
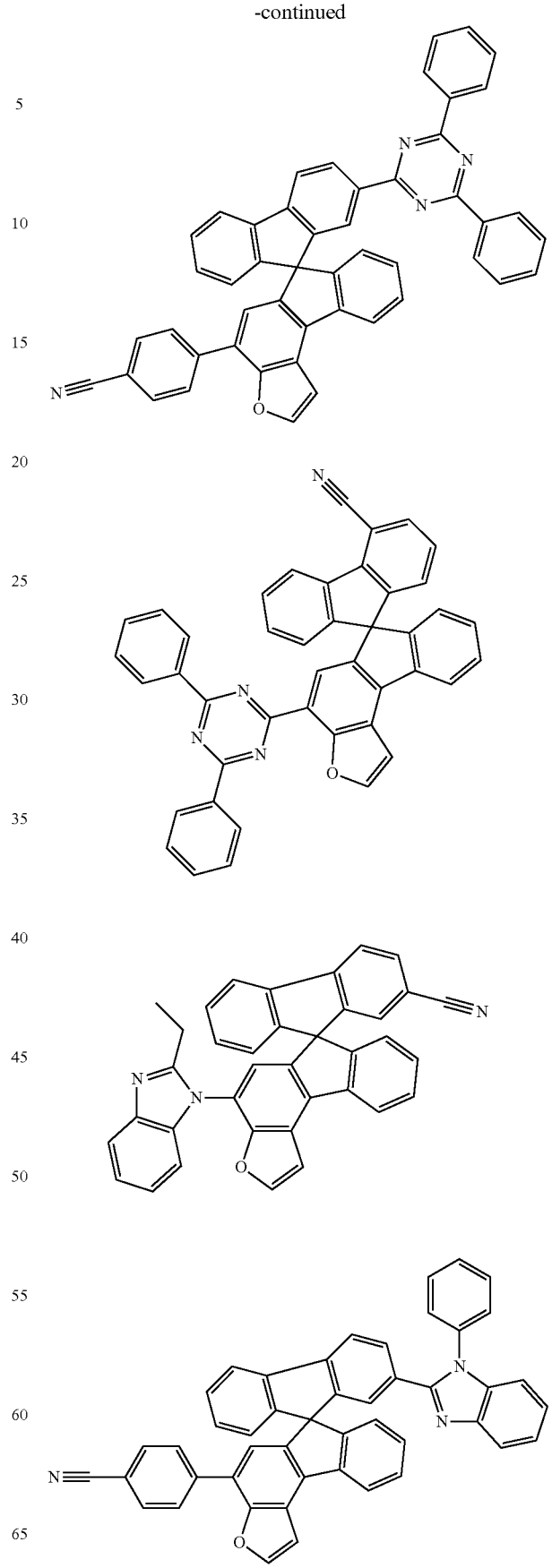

35
-continued
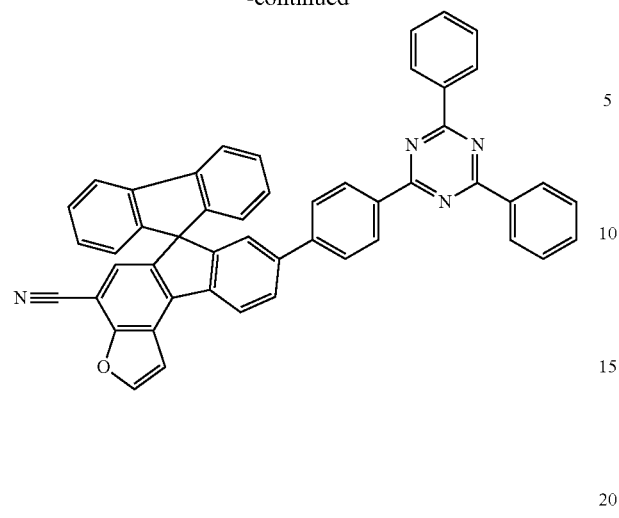
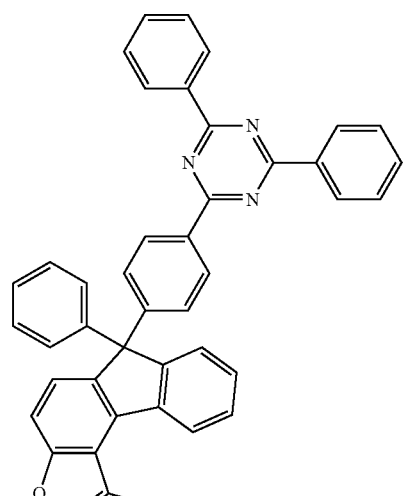
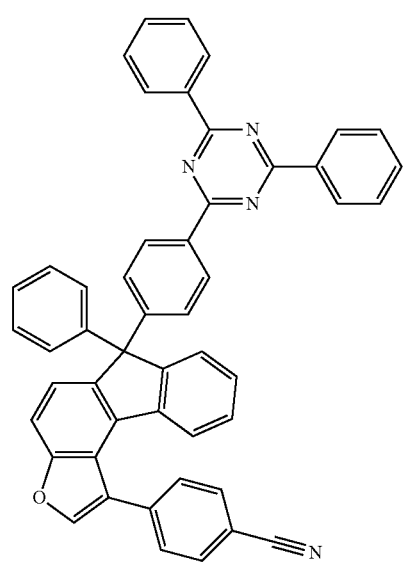
36
-continued
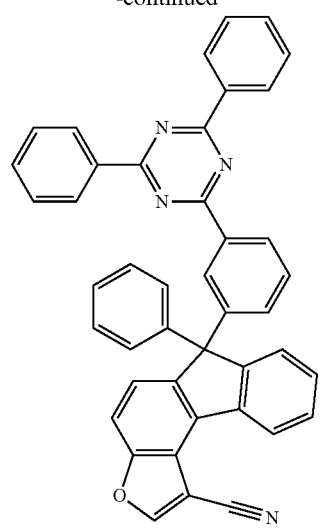
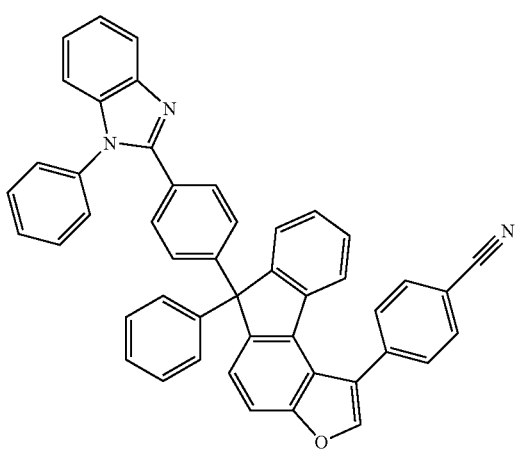

37
-continued
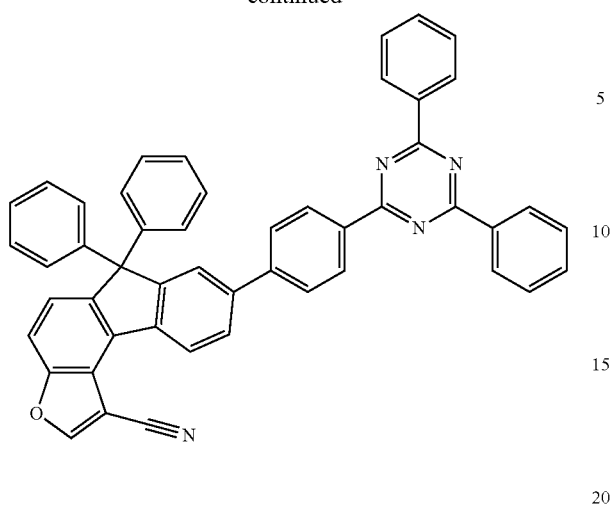
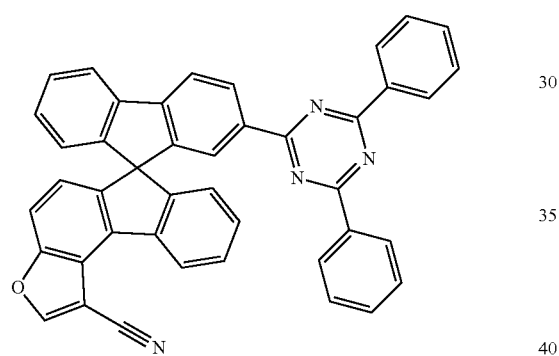
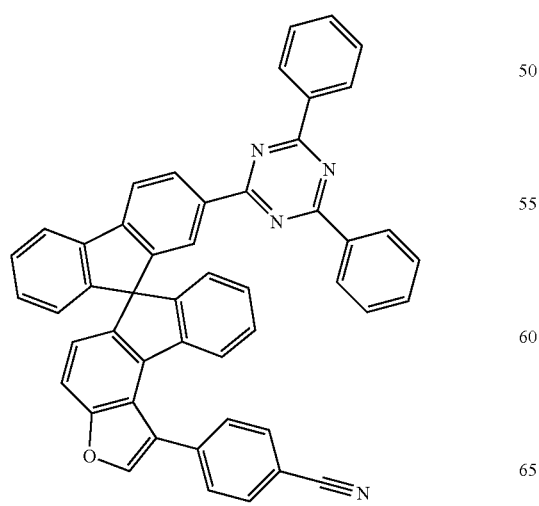
38
-continued
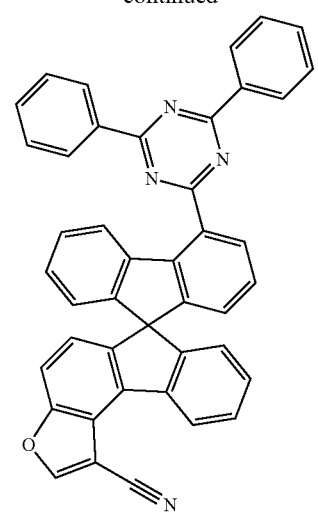
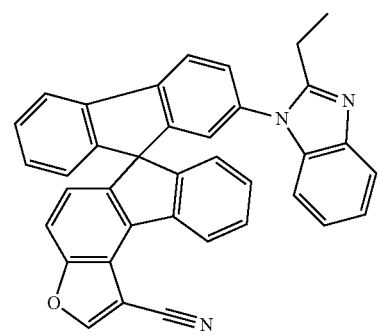
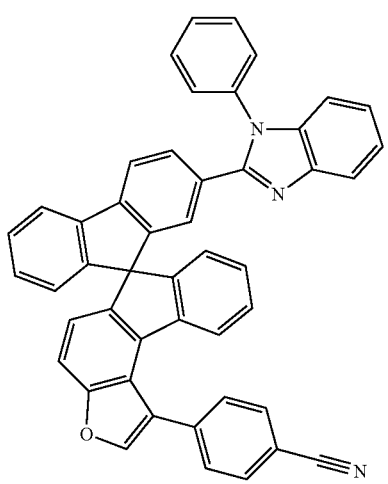

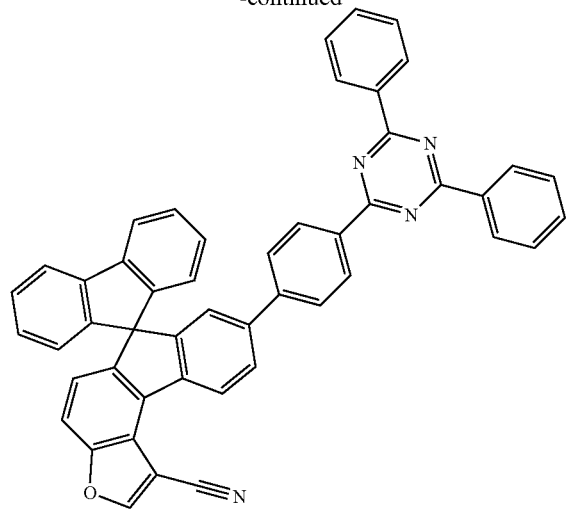
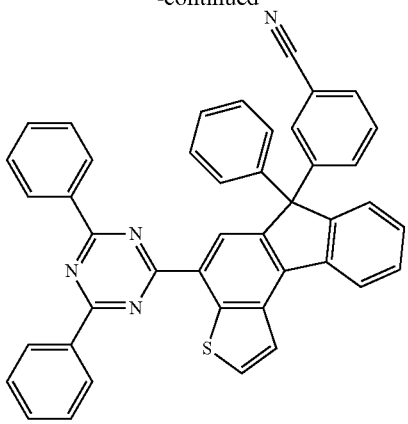
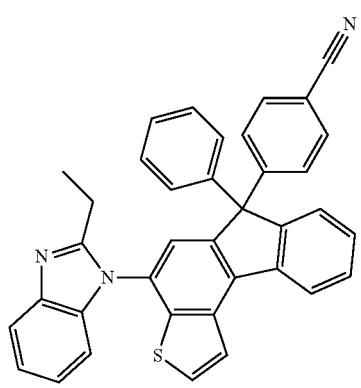
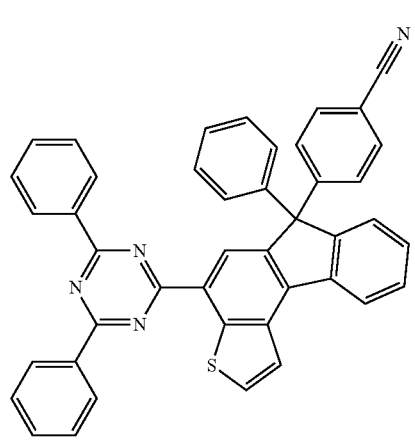
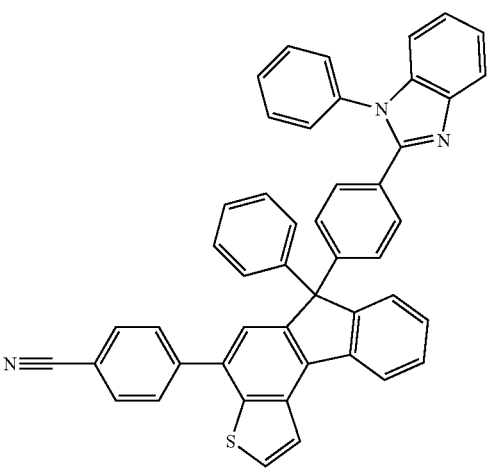
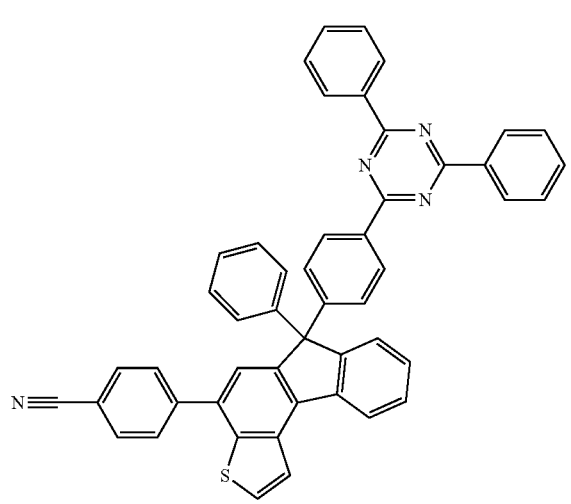

41
-continued
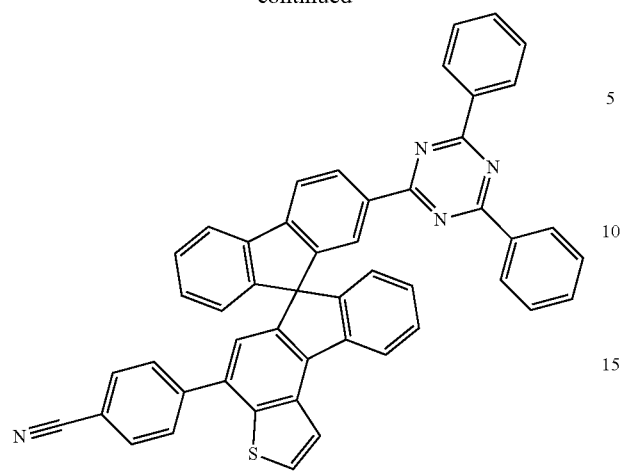
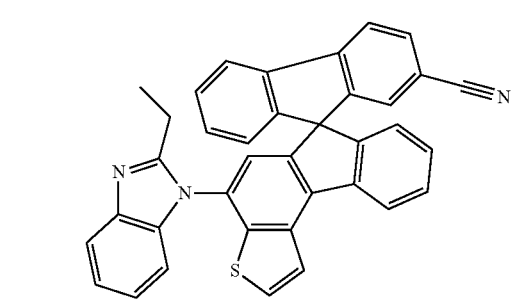
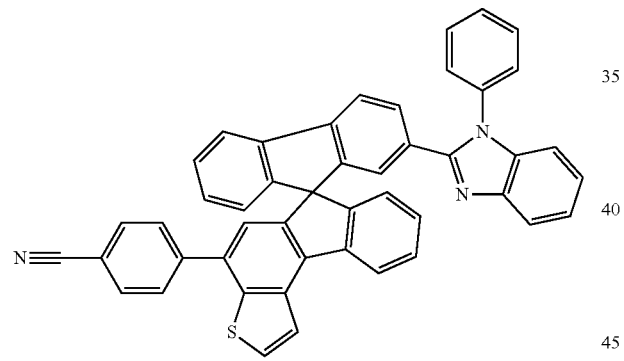
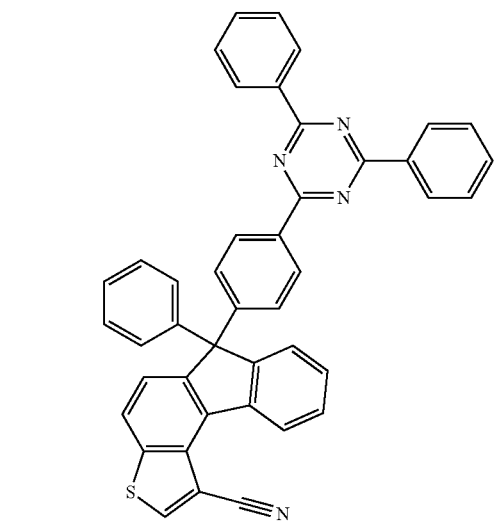
42
-continued
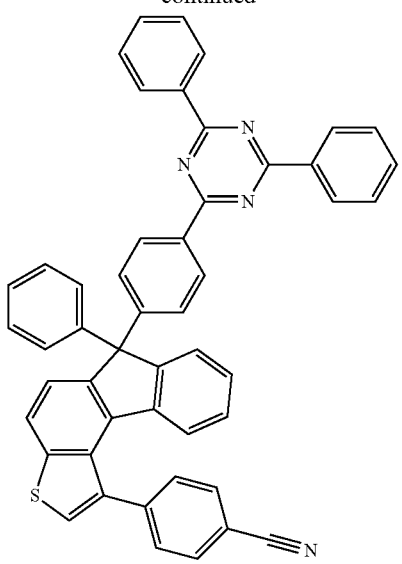
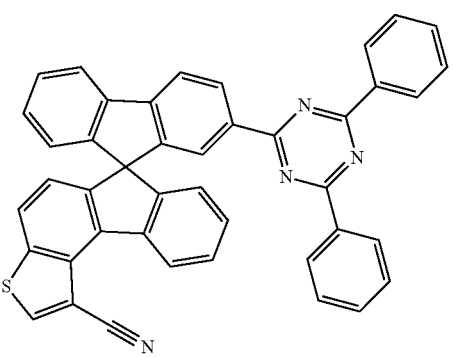
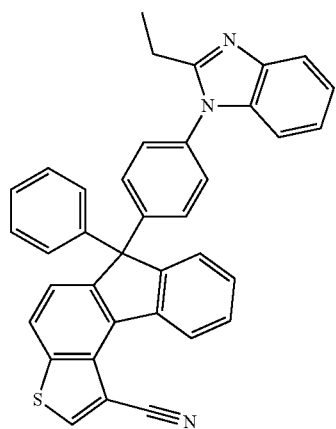

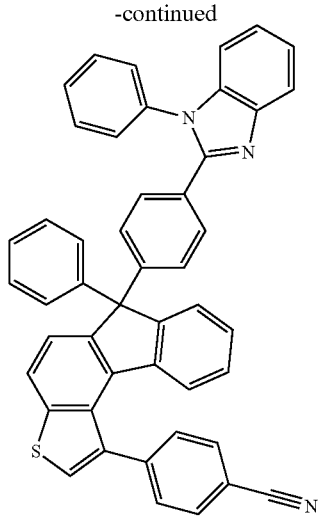
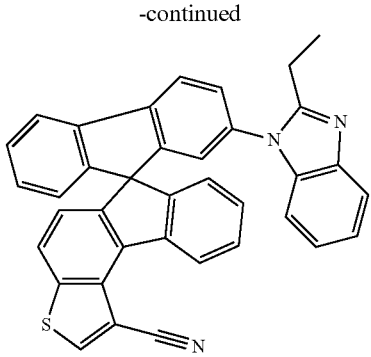

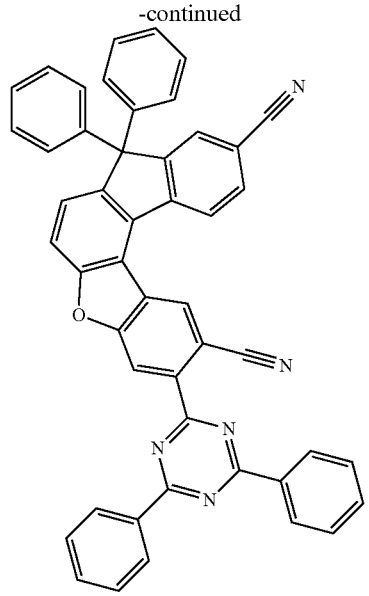
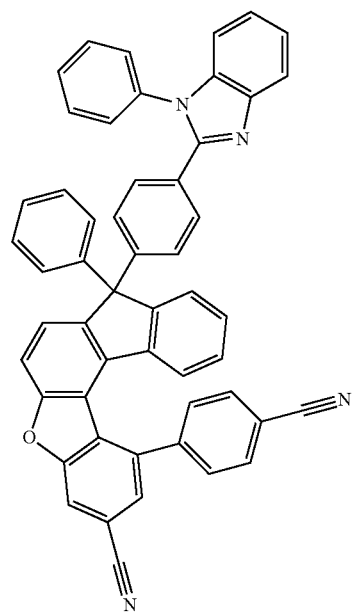
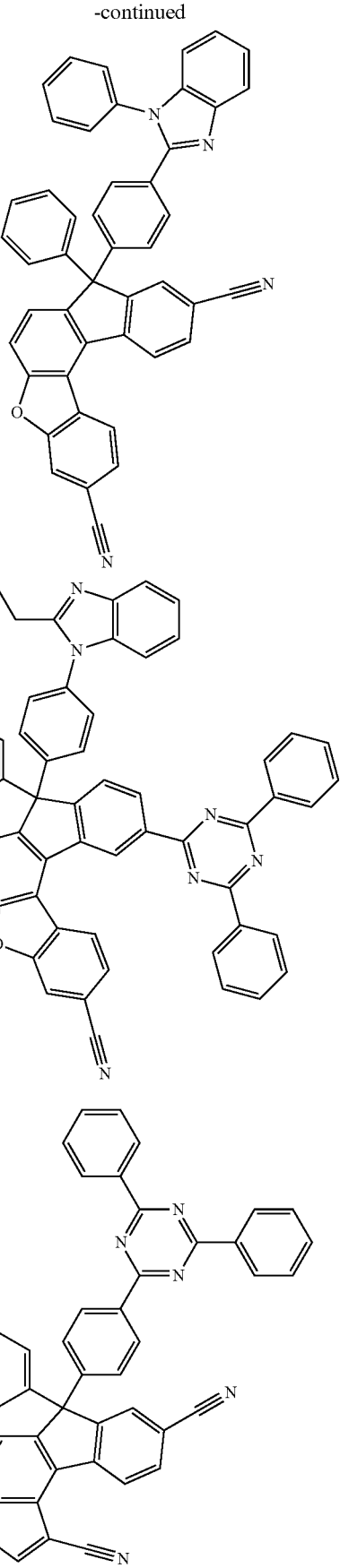

47
-continued
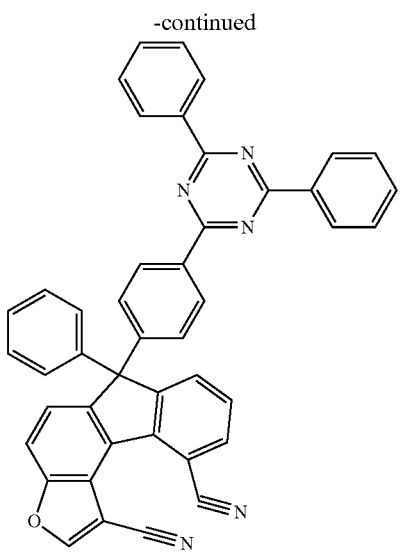
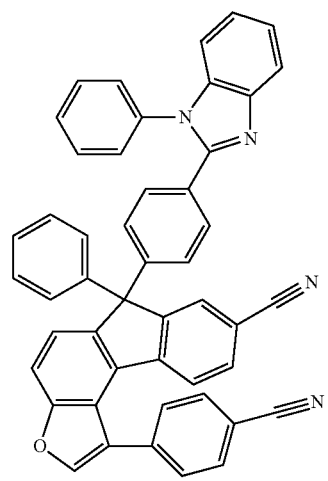
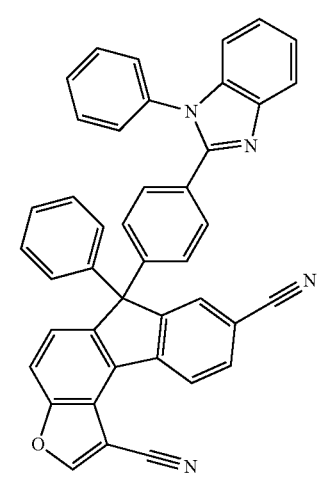 [SMILES: N#Cc1ccc2c(c1)C(c1ccccc1)(c1ccc(-c3nc4ccccc4n3-c3ccccc3)cc1)c1ccc3occ(C#N)c3c1-2]
48
-continued
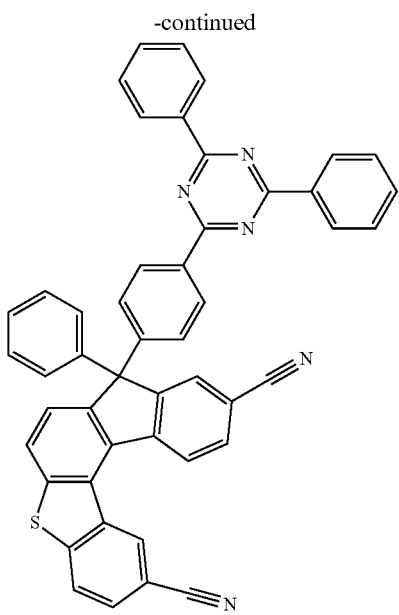
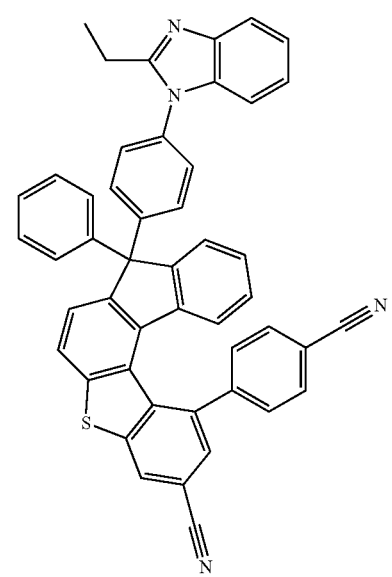

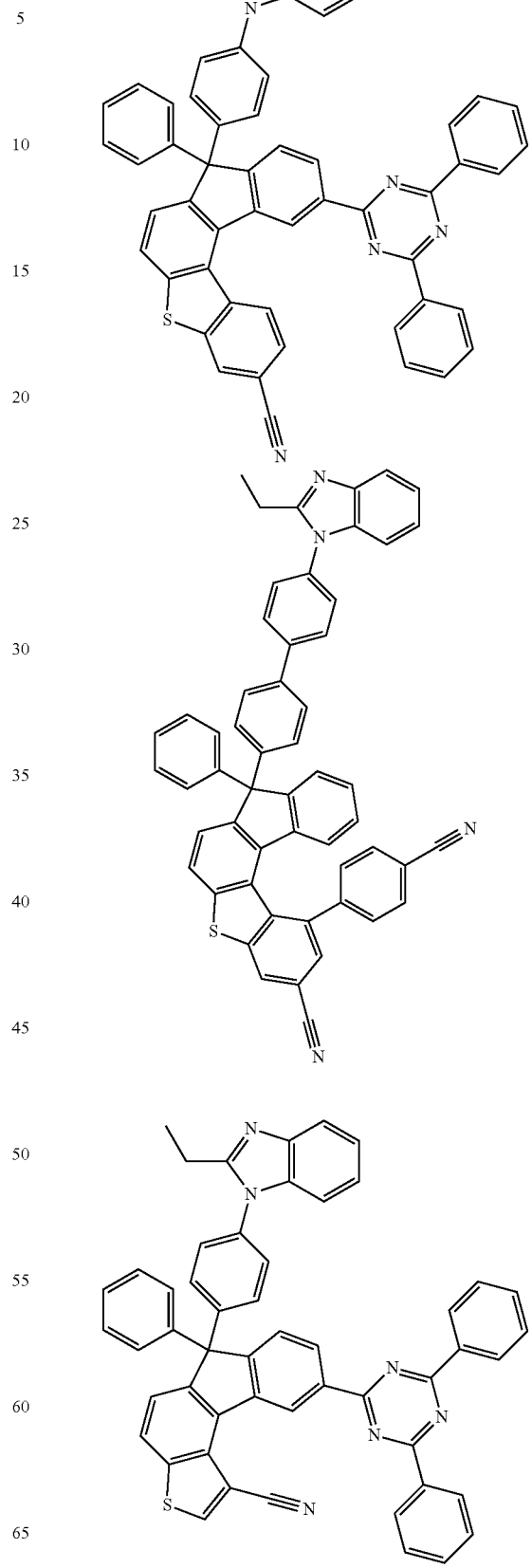

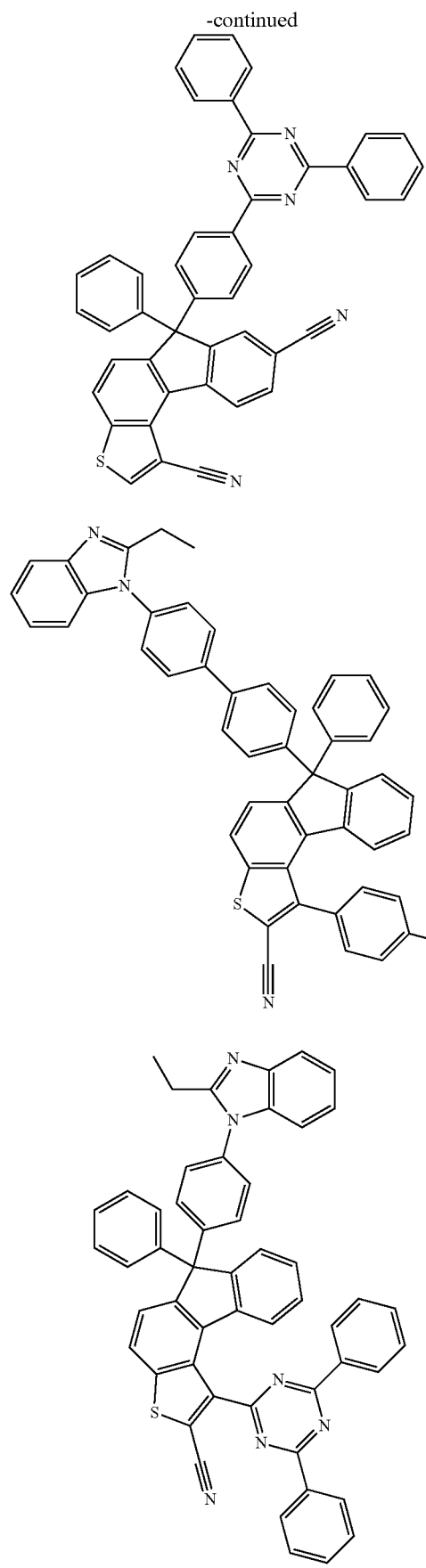
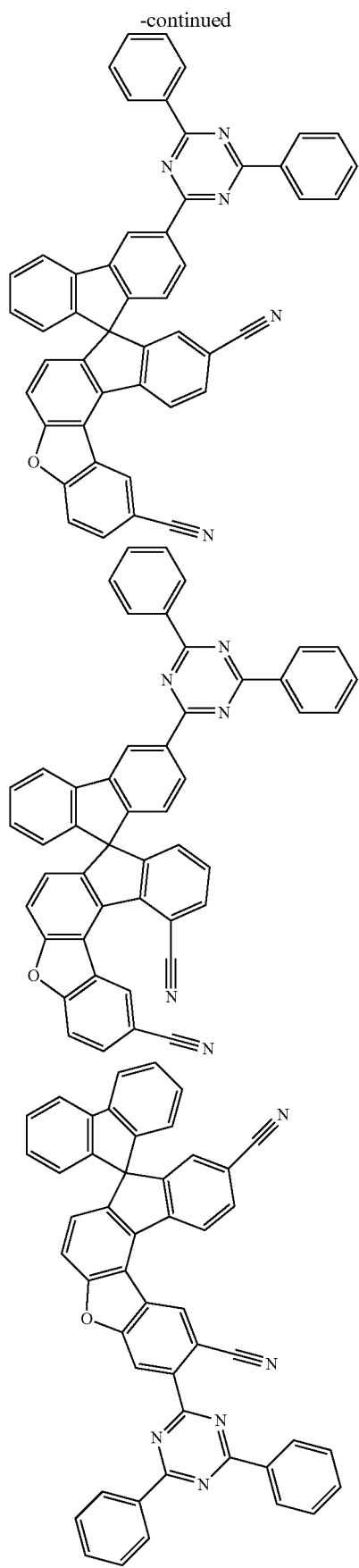

53
-continued
54
-continued
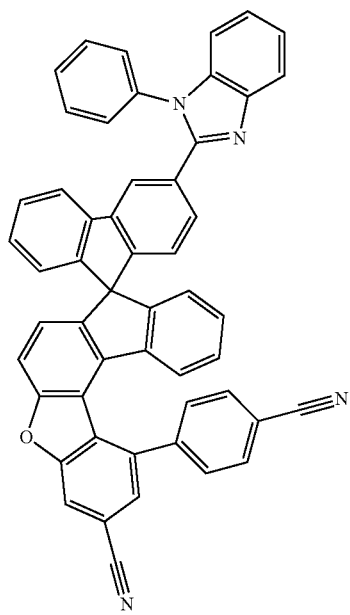
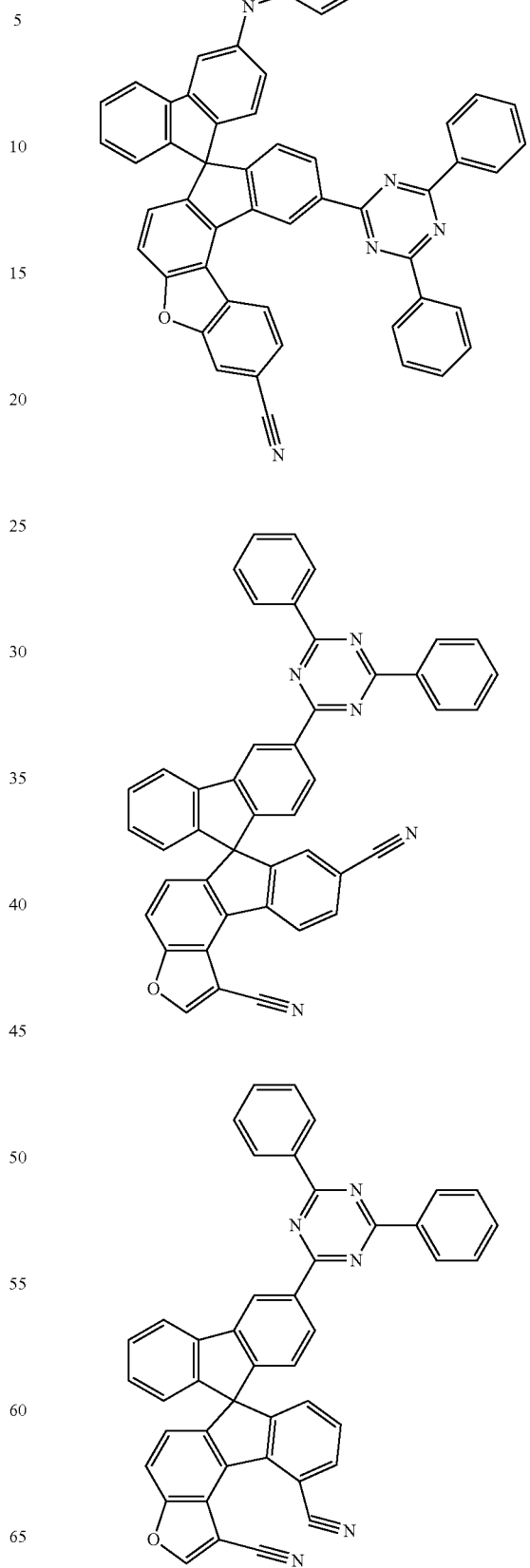
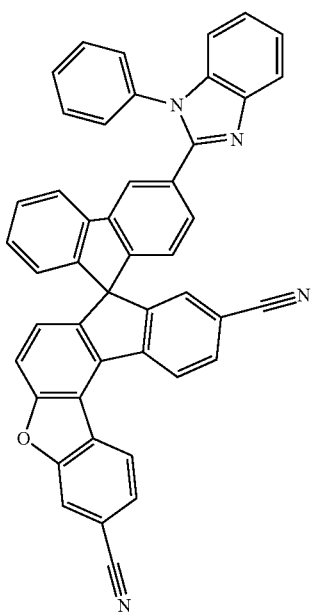

55
-continued
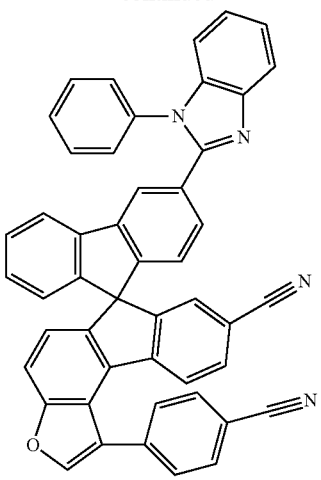
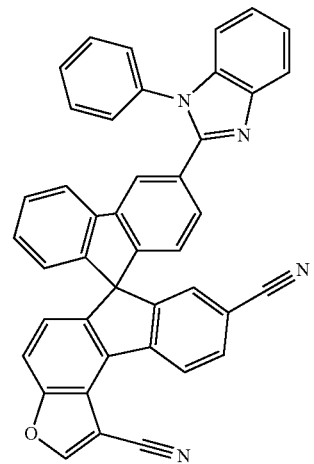 [SMILES: N#Cc1ccc2c(c1)C1(c3ccccc3-c3cc(-c4nc5ccccc5n4-c4ccccc4)ccc31)c1ccc3occ(C#N)c3c1-2]
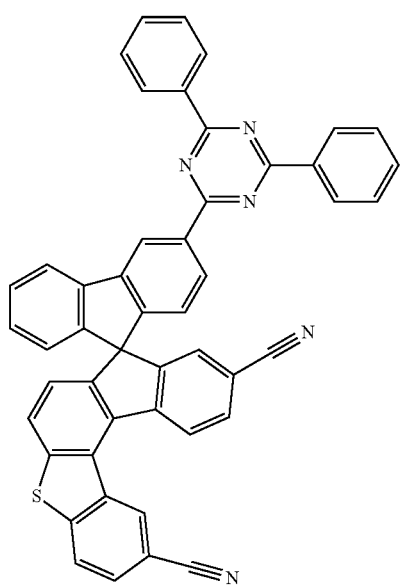
56
-continued
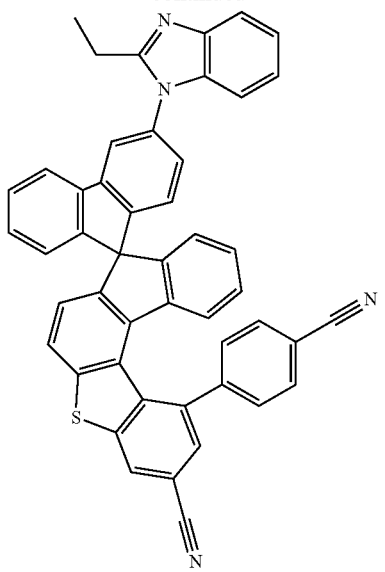
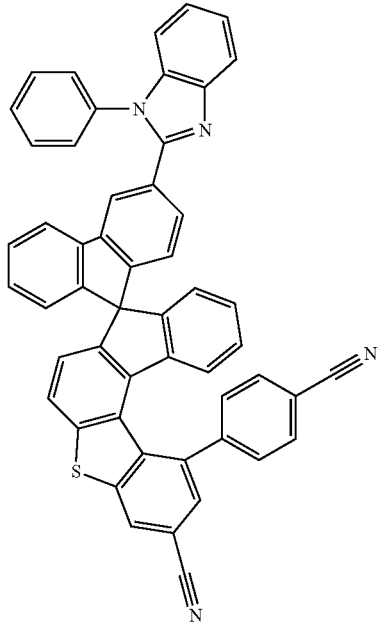

57
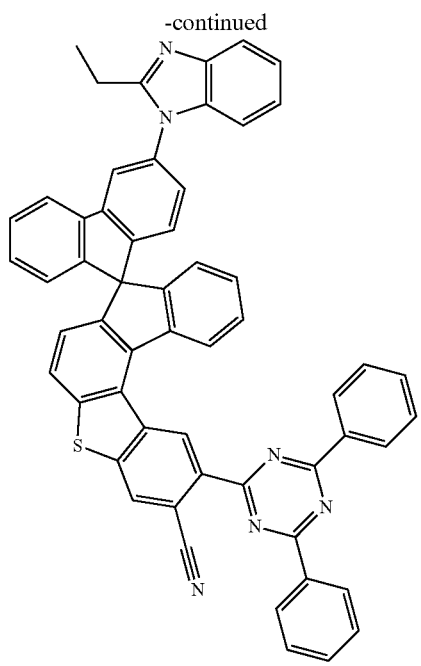
58
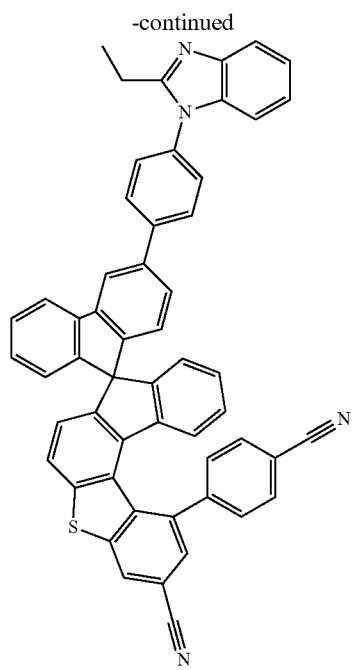
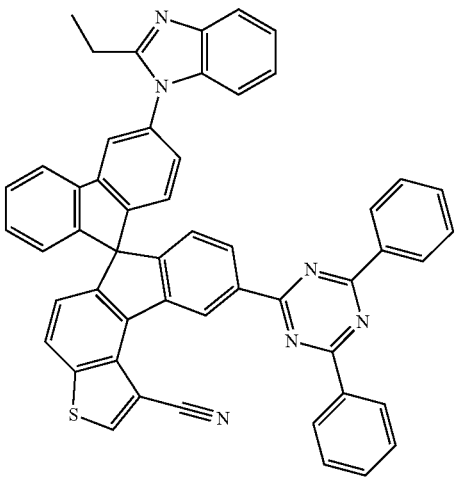
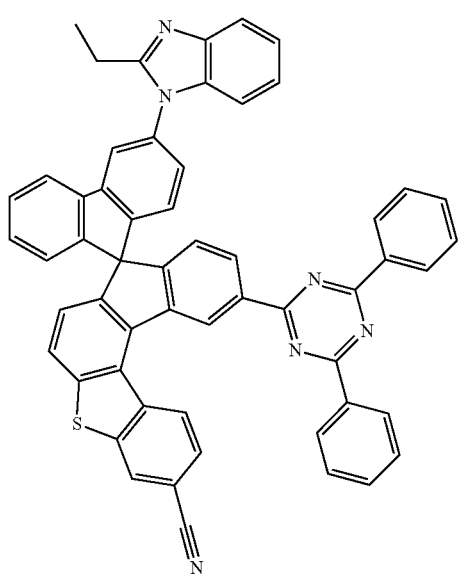
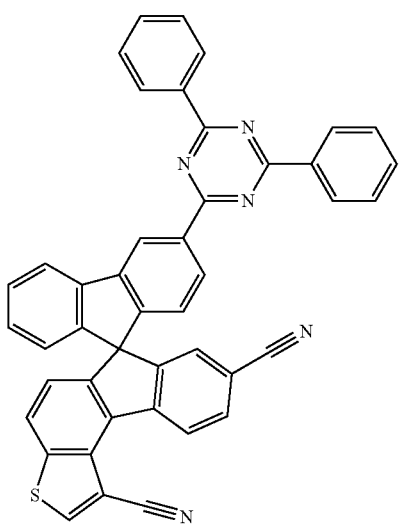

59
-continued
60
-continued
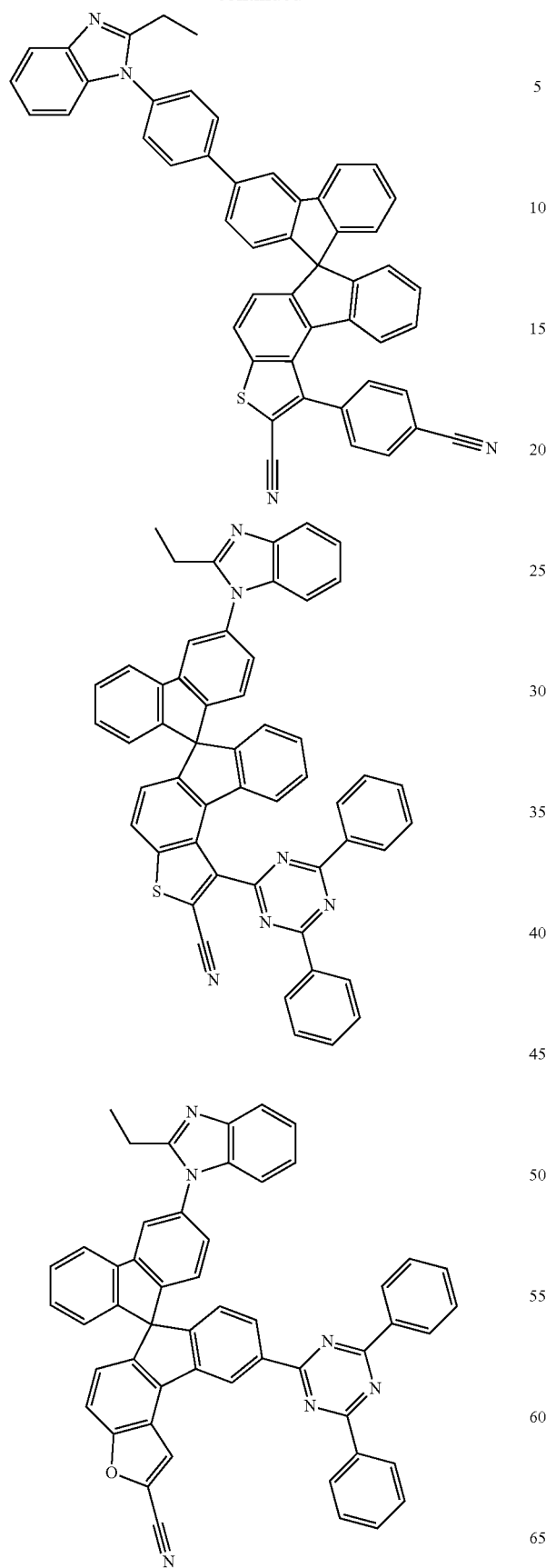

61
-continued
62
-continued
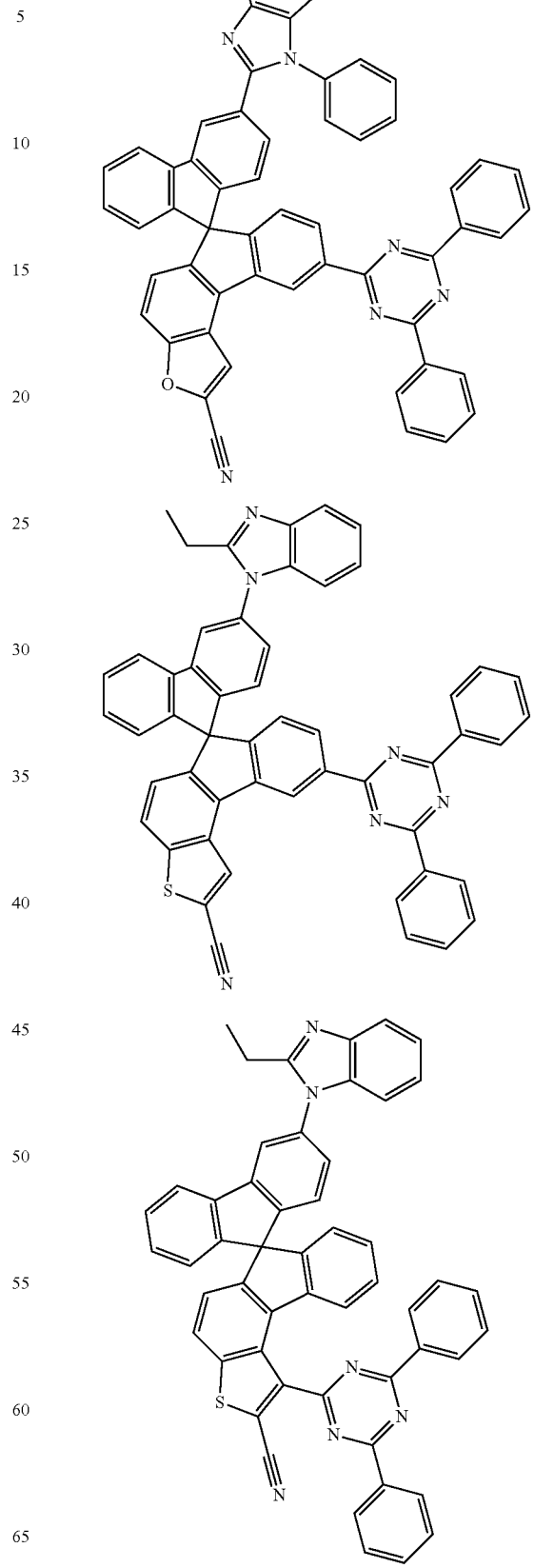

63
-continued
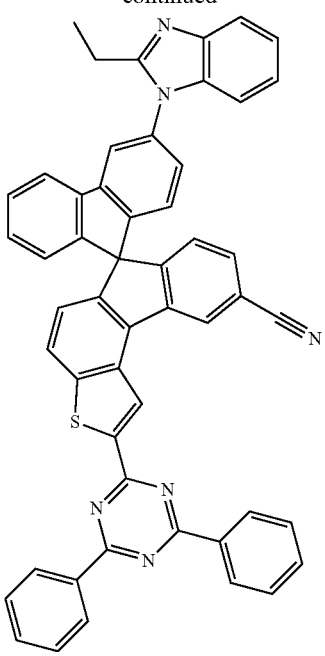
64
-continued
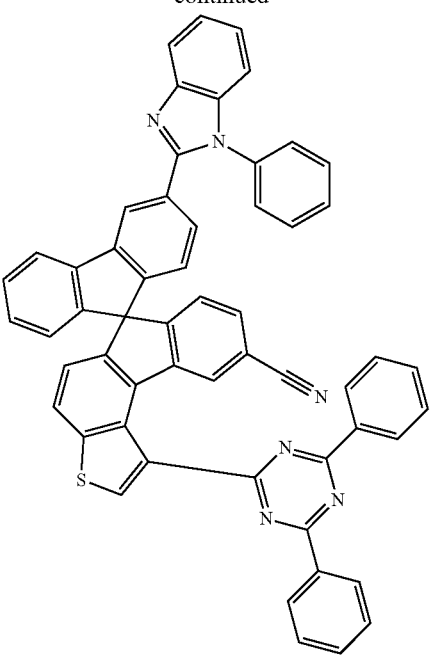
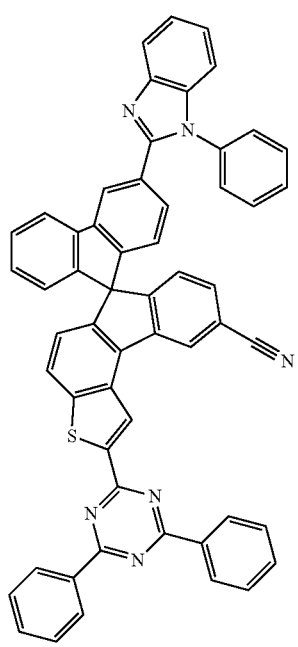
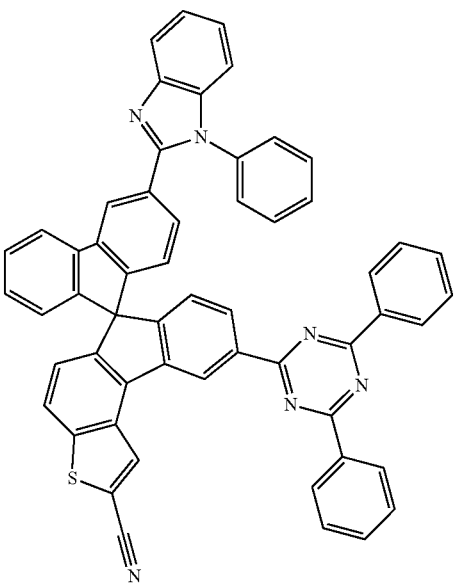
Meanwhile, as an example, when $HAr_1$ is Chemical Formula 2 and $HAr_3$ is Chemical Formula 3, the above-mentioned compound represented by Chemical Formula 1 can be prepared by the method as shown in the following Reaction Scheme 1-1 or 1-2. The preparation method may be more specifically described in the Preparation Examples described hereinafter.

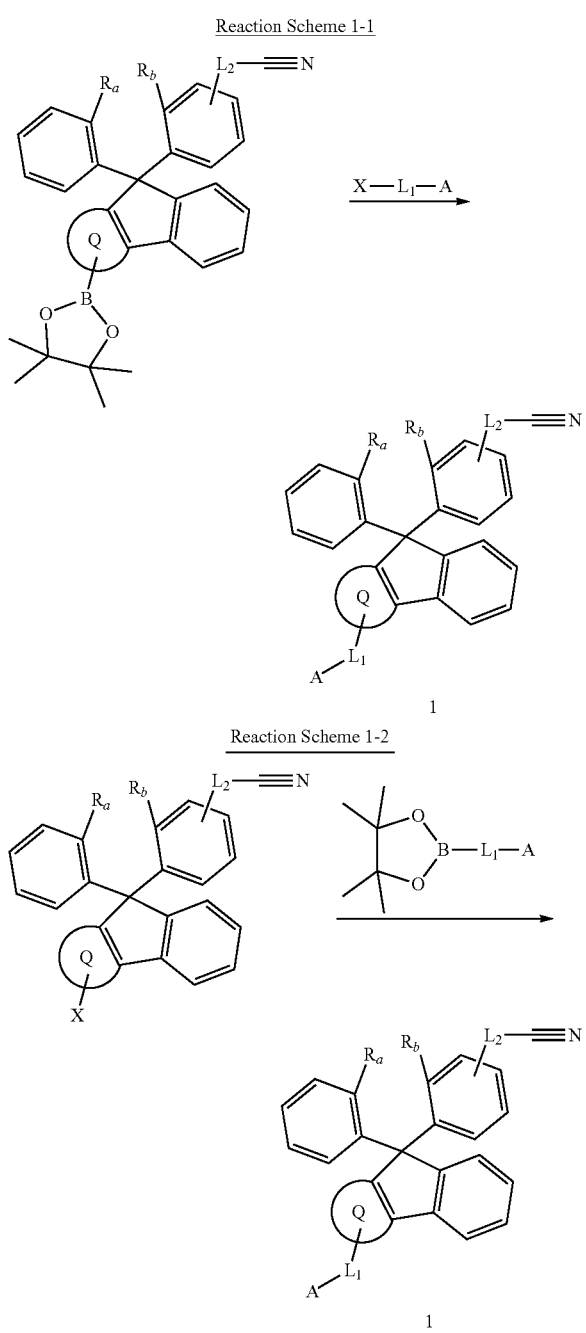

Reaction Scheme 1-1

Reaction Scheme 1-2 in the above Reaction Schemes 1-1 and 1-2, X is halogen, and the remaining substituents are the same as defined in Chemical Formula 1. The above reaction is a Suzuki coupling reaction, which is preferably carried out in the presence of a palladium catalyst and a base, and a reactive group for the Suzuki coupling reaction can be modified as known in the art. The above preparation method will be more specifically described in the Preparation Examples described hereinafter.

Meanwhile, according to another aspect of the present disclosure, there is provided an organic light emitting device comprising the above-mentioned compound represented by Chemical Formula 1. As an example, there is provided an organic light emitting device comprising: a first electrode; a second electrode that is provided to face the first electrode; and one or more organic material layers that are provided between the first electrode and the second electrode, wherein at least one layer of the organic material layers includes the compound represented by Chemical Formula 1.

The organic material layer of the organic light emitting device of the present disclosure may have a single-layer structure, or it may have a multilayered structure in which two or more organic material layers are stacked. For example, the organic light emitting device of the present disclosure may have a structure comprising a hole injection layer, a hole transport layer, a light emitting layer, an electron transport layer, an electron injection layer and the like as the organic material layer. However, the structure of the organic light emitting device is not limited thereto, and it may include a smaller number of organic layers.

Preferably, the organic material layer may include a hole transport layer, a light emitting layer and an electron transport layer, wherein the electron transport layer includes the compound represented by Chemical Formula 1.

Also, preferably, the organic material layer may include a hole injection layer, a hole transport layer, a light emitting layer, an electron transport layer and an electron injection layer, wherein the electron transport layer includes the compound represented by Chemical Formula 1.

The organic material layer of the organic light emitting device of the present disclosure may have a single-layer structure, or it may have a multilayered structure in which two or more organic material layers are stacked. For example, the organic light emitting device of the present disclosure may have a structure further comprising a hole injection layer and a hole transport layer provided between the first electrode and the light emitting layer, and an electron transport layer and an electron injection layer provided between the light emitting layer and the second electrode, in addition to the light emitting layer. However, the structure of the organic light emitting device is not limited thereto, and it may include a smaller number of organic layers or a larger number of organic layers.

Further, the organic light emitting device according to the present disclosure may be a normal type organic light emitting device in which an anode, one or more organic material layers and a cathode are sequentially stacked on a substrate. Further, the organic light emitting device according to the present disclosure may be an inverted type organic light emitting device in which a cathode, one or more organic material layers and an anode are sequentially stacked on a substrate. For example, the structure of an organic light emitting device according to an embodiment of the present disclosure is illustrated in FIGS. 1 and 2.

FIG. 1 shows an example of an organic light emitting device comprising a substrate 1, an anode 2, a hole transport layer 3, a light emitting layer 4, an electron transport layer 5 and a cathode 6. In such a structure, the compound represented by Chemical Formula 1 may be included in the electron transport layer 5.

FIG. 2 shows an example of an organic light emitting device comprising a substrate 1, an anode 2, a hole injection layer 7, a hole transport layer 3, an electron blocking layer 8, a light emitting layer 4, a hole blocking layer 9, an electron transport layer 5, an electron injection layer 10 and a cathode 6. In such a structure, the compound represented by Chemical Formula 1 may be included in the electron transport layer 5.

The organic light emitting device according to the present disclosure may be manufactured by materials and methods known in the art, except that one or more layers of the organic material layers include the compound represented by Chemical Formula 1. Moreover, when the organic light emitting device includes a plurality of organic material layers, the organic material layers may be formed of the same material or different materials.

For example, the organic light emitting device according to the present disclosure can be manufactured by sequentially stacking a first electrode, an organic material layer and a second electrode on a substrate. In this case, the organic light emitting device may be manufactured by depositing a metal, metal oxides having conductivity, or an alloy thereof on the substrate using a PVD (physical vapor deposition) method such as a sputtering method or an e-beam evaporation method to form an anode, forming organic material layers including the hole injection layer, the hole transport layer, the light emitting layer and the electron transport layer thereon, and then depositing a material that can be used as the cathode thereon. In addition to such a method, the organic light emitting device may be manufactured by sequentially depositing a cathode material, an organic material layer and an anode material on a substrate.

Further, the compound represented by Chemical Formula 1 may be formed into an organic layer by a solution coating method as well as a vacuum deposition method at the time of manufacturing an organic light emitting device. Herein, the solution coating method means a spin coating, a dip coating, a doctor blading, an inkjet printing, a screen printing, a spray method, a roll coating, or the like, but is not limited thereto.

In addition to such a method, the organic light emitting device may be manufactured by sequentially depositing a cathode material, an organic material layer and an anode material on a substrate (International Publication WO2003/012890). However, the manufacturing method is not limited thereto.

As an example, the first electrode is an anode, and the second electrode is a cathode, or alternatively, the first electrode is a cathode and the second electrode is an anode.

As the anode material, generally, a material having a large work function is preferably used so that holes can be smoothly injected into the organic material layer. Specific examples of the anode material include metals such as vanadium, chrome, copper, zinc, and gold, or an alloy thereof; metal oxides such as zinc oxides, indium oxides, indium tin oxides (ITO), and indium zinc oxides (IZO); a combination of metals and oxides, such as ZnO:Al or $SnO_2$:Sb; conductive polymers such as poly(3-methylthiophene), poly[3,4-(ethylene-1,2-dioxy)thiophene](PEDOT), polypyrrole, and polyaniline, and the like, but are not limited thereto.

As the cathode material, generally, a material having a small work function is preferably used so that electrons can be easily injected into the organic material layer. Specific examples of the cathode material include metals such as magnesium, calcium, sodium, potassium, titanium, indium, yttrium, lithium, gadolinium, aluminum, silver, tin, and lead, or an alloy thereof; a multilayered structure material such as LiF/Al or $LiO_2$/Al, and the like, but are not limited thereto.

The hole injection layer is a layer for injecting holes from the electrode, and the hole injection material is preferably a compound which has a capability of transporting the holes, thus has a hole injecting effect in the anode and an excellent hole-injecting effect to the light emitting layer or the light emitting material, prevents excitons produced in the light emitting layer from moving to an electron injection layer or the electron injection material, and is excellent in the ability to form a thin film. It is preferable that a HOMO (highest occupied molecular orbital) of the hole injection material is between the work function of the anode material and a HOMO of a peripheral organic material layer. Specific examples of the hole injection material include metal porphyrine, oligothiophene, an arylamine-based organic material, a hexanitrilehexaazatriphenylene-based organic material, a quinacridone-based organic material, a perylene-based organic material, anthraquinone, polyaniline and polythiophene-based conductive polymer, and the like, but are not limited thereto.

The hole transport layer is a layer that receives holes from a hole injection layer and transports the holes to the light emitting layer. The hole transport material is suitably a material having large mobility to the holes, which may receive holes from the anode or the hole injection layer and transfer the holes to the light emitting layer. Specific examples thereof include an arylamine-based organic material, a conductive polymer, a block copolymer in which a conjugate portion and a non-conjugate portion are present together, and the like, but are not limited thereto.

The electron blocking layer refers to a layer that is located between the hole transport layer and the light emitting layer and is mainly disposed in contact with the light emitting layer to prevent excessive movement of electron and increase the probability of hole-electron bonding, thereby serving to improve the efficiency of an organic light emitting device. The electron blocking layer comprises an electron blocking material, and examples of such electron blocking materials include arylamine-based organic materials and the like, but are not limited thereto.

The light emitting layer is preferably a layer which may receive holes and electrons transported from a hole transport layer and an electron transport layer, respectively, and combine the holes and the electrons to emit light in a visible ray region, and has good quantum efficiency to fluorescence or phosphorescence. Specifically, the light emitting layer may include a host material and a dopant material.

The host material may be a fused aromatic ring derivative, a heterocycle-containing compound or the like. Specific examples of the fused aromatic ring derivatives include anthracene derivatives, pyrene derivatives, naphthalene derivatives, pentacene derivatives, phenanthrene compounds, fluoranthene compounds, and the like. Examples of the heterocyclic-containing compounds include carbazole derivatives, dibenzofuran derivatives, ladder-type furan compounds, pyrimidine derivatives, and the like, but are not limited thereto.

The dopant material includes an aromatic amine derivative, a styrylamine compound, a boron complex, a fluoranthene compound, a metal complex, and the like. Specifically, the aromatic amine derivative is a substituted or unsubstituted fused aromatic ring derivative having an arylamino group, and examples thereof include pyrene, anthracene, chrysene, periflanthene and the like, which have an arylamino group. The styrylamine compound is a compound where at least one arylvinyl group is substituted in substituted or unsubstituted arylamine, in which one or two or more substituent groups selected from the group consisting of an aryl group, a silyl group, an alkyl group, a cycloalkyl group, and an arylamino group are substituted or unsubstituted. Specific examples thereof include styrylamine, styryldiamine, styryltriamine, styryltetramine, and the like, but are not limited thereto. Further, the metal complex includes an iridium complex, a platinum complex, and the like, but is not limited thereto.

The hole blocking layer refers to a layer that is located between the light emitting layer and the electron transport layer and is mainly disposed in contact with the light emitting layer to prevent holes from moving to the electron transport layer and increase the probability of hole-electron bonding, thereby serving to improve the efficiency of an organic light emitting device. The hole blocking layer comprises a hole blocking material, and examples of such hole blocking materials include triazole derivatives; oxadiazole derivatives; phenanthroline derivatives; and the like, but are not limited thereto.

The electron transport layer is a layer which receives electrons from an electron injection layer and transports the electrons to a light emitting layer, and an electron transport material used is a compound of Chemical Formula 1 which is a material which can receive electrons well from a cathode and transfer the electrons to a light emitting layer and has large mobility for electrons. Additionally, it may further include: an Al complex of 8-hydroxyquinoline; a complex including Alq$_3$; an organic radical compound; a hydroxyflavone-metal complex, and the like. The electron transport layer may be used with any desired cathode material, as used according to the related art. In particular, appropriate examples of the cathode material are a typical material which has a low work function, followed by an aluminum layer or a silver layer. Specific examples thereof include cesium, barium, calcium, ytterbium, and samarium, in each case followed by an aluminum layer or a silver layer.

The electron injection layer is a layer which injects electrons from an electrode, and is preferably a compound which has a capability of transporting electrons, has an effect of injecting electrons from a cathode and an excellent effect of injecting electrons into a light emitting layer or a light emitting material, prevents excitons produced from the light emitting layer from moving to a hole injection layer, and is also excellent in the ability to form a thin film. Specific examples thereof include LiF, NaF, NaCl, CsF, Li$_2$O, BaO, fluorenone, anthraquinodimethane, diphenoquinone, thiopyran dioxide, oxazole, oxadiazole, triazole, imidazole, perylenetetracarboxylic acid, fluorenylidene methane, anthrone, and the like, and derivatives thereof, a metal complex compound, a nitrogen-containing 5-membered ring derivative, and the like, but are not limited thereto.

Examples of the metal complex compound include 8-hydroxyquinolinato lithium, bis(8-hydroxyquinolinato)zinc, bis(8-hydroxyquinolinato)copper, bis(8-hydroxyquinolinato)manganese, tris(8-hydroxyquinolinato)aluminum, tris(2-methyl-8-hydroxyquinolinato)aluminum, tris(8-hydroxyquinolinato)gallium, bis(10-hydroxybenzo[h]quinolinato)beryllium, bis(10-hydroxybenzo[h]quinolinato)zinc, bis(2-methyl-8-quinolinato)chlorogallium, bis(2-methyl-8-quinolinato)(o-cresolato)gallium, bis(2-methyl-8-quinolinato)(1-naphtholato)aluminum, bis(2-methyl-8-quinolinato)(2-naphtholato)gallium, and the like, but are not limited thereto.

The organic light emitting device according to the present disclosure may be a front side emission type, a backside emission type, or a double-sided emission type according to the used material.

In addition, the compound represented by Chemical Formula 1 may be included in an organic solar cell or an organic transistor in addition to an organic light emitting device.

The preparation of the compound represented by Chemical Formula 1 and the organic light emitting device containing the same will be described in detail in the following examples. However, these examples are presented for illustrative purposes only, and are not intended to limit the scope of the present disclosure.

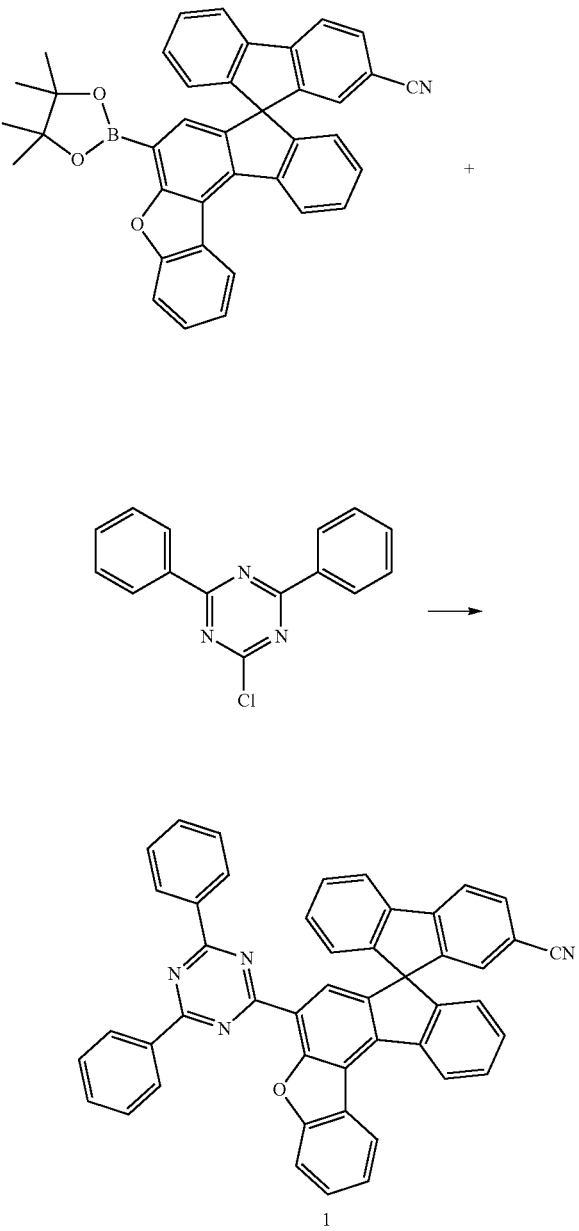

Preparation Example 1: Synthesis of Compound 1

After 6'-(4,4,5,5-tetramethyl-1,3,2-dioxaborolan-2-yl) spiro[fluorene-9,8'-fluoreno[3,4-b]benzofuran]-2-carbonitrile (10.0 g, 17.9 mmol) and 2-chloro-4,6-diphenyl-1,3,5-triazine (5.0 g, 18.8 mmol) were completely dissolved in 100 ml of tetrahydrofuran, potassium carbonate (7.4 g, 53.7 mmol) dissolved in 43 ml of water was added and tetrakis-triphenyl-phosphine palladium (620 mg, 0.537 mmol) was added thereto, followed by heating and stirring for 7 hours. The reaction temperature was lowered to a room temperature, the reaction was completed, and then the potassium carbonate solution was removed to filter a white solid. The filtered white solid was washed with tetrahydrofuran and ethyl acetate two times, respectively, to prepare Compound 1 (9.5 g, yield: 80%).

MS[M+H]$^+$=662

Preparation Example 2: Synthesis of Compound 2

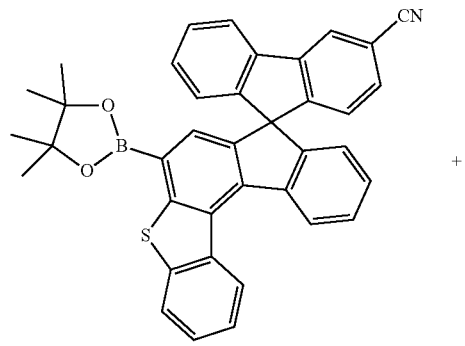

+

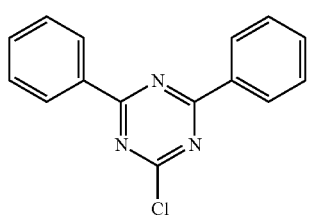

→

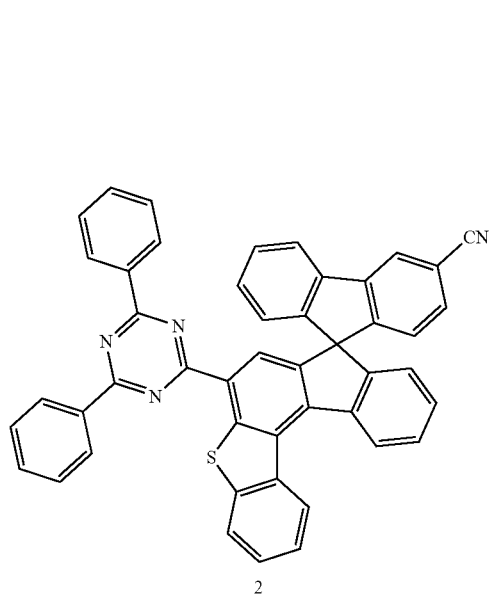

2

Compound 2 (10.3 g, yield: 85%) was prepared in the same manner as in Preparation Example 1, except that 6-(4,4,5,5-tetramethyl-1,3,2-dioxaborolan-2-yl)spiro[benzo[b]fluoreno[4,3-d]thiophen-8,9'-fluorene]-3'-carbonitrile was used instead of 6'-(4,4,5,5-tetramethyl-1,3,2-dioxaborolan-2-yl)spiro[fluorene-9,8'-fluoreno[3,4-b]benzofuran]-2-carbonitrile in Preparation Example 1.

MS[M+H]$^+$=678

Preparation Example 3: Synthesis of Compound 3

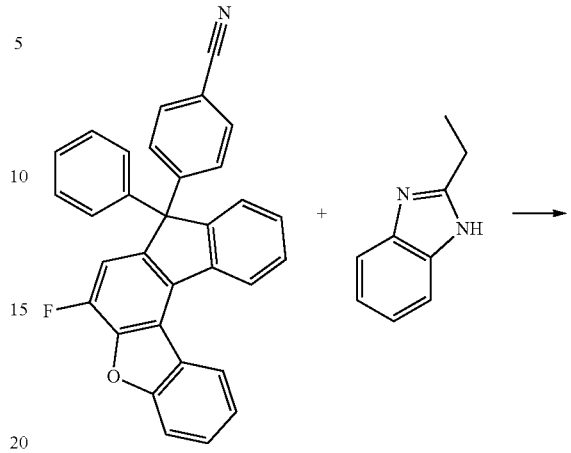

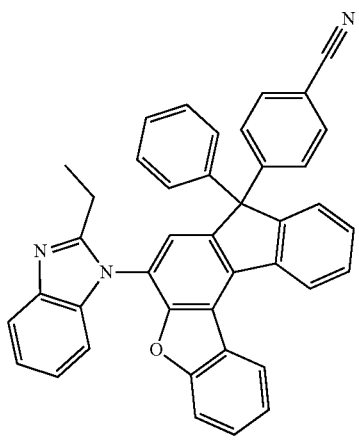

3

4-(6-fluoro-8-phenyl-8H-fluoreno[3,4-b]benzofuran-8-yl)benzonitrile (10.0 g, 22.1 mmol), 2-ethyl-1H-benzo[d]imidazole (3.2 g, 22.1 mmol) and cesium carbonate (14.4 g, 44.2 mmol) were added to dimethylacetamide (130 ml), and then the mixture was heated and stirred at 120° C. or higher for 10 hours. The reaction temperature was lowered to a room temperature, the reaction was completed, and then water was added and filtered to obtain a solid, thereby preparing Compound 3 (10.2 g, yield: 80%).

MS[M+H]$^+$=577

Preparation Example 4: Synthesis of Compound 4

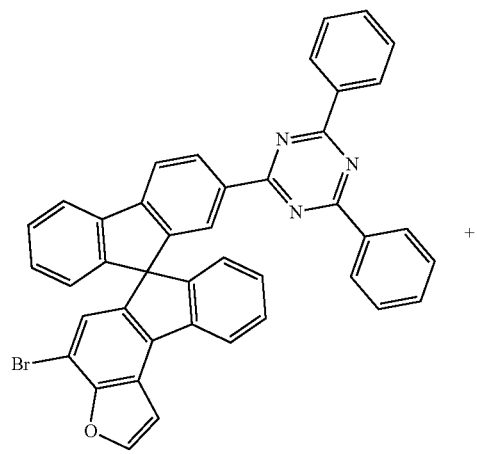

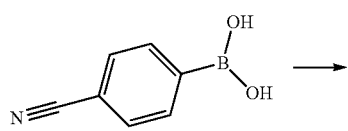

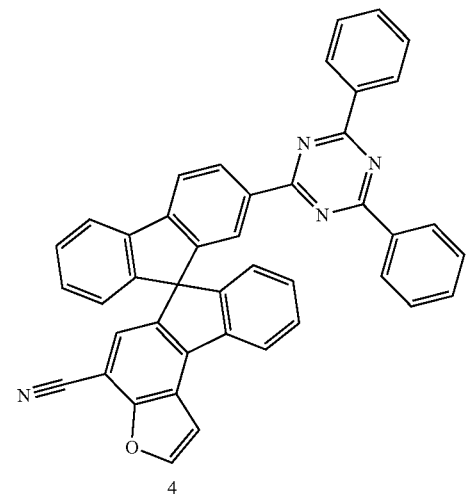
4

Compound 4 (8.6 g, yield: 70%) was prepared in the same manner as in Preparation Example 1, except that 2-(4'-bromospiro[fluorene-9,6'-fluoreno[3,4-b]furan]-2-yl)-4,6-diphenyl-1,3,5-triazine was used instead of 6'-(4,4,5,5-tetramethyl-1,3,2-dioxaborolan-2-yl)spiro[fluorine-9,8'-fluoreno[3,4-b]benzofuran]-2-carbonitrile in Preparation Example 1, and (4-cyanophenyl)boronic acid was used instead of 2-chloro-4,6-diphenyl-1,3,5-triazine.

MS[M+H]⁺=688

Preparation Example 5: Synthesis of Compound 5

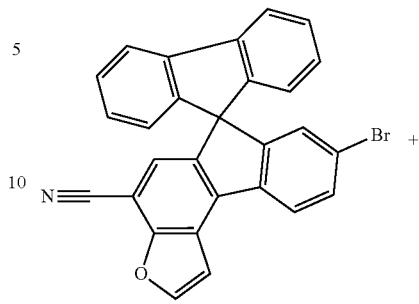

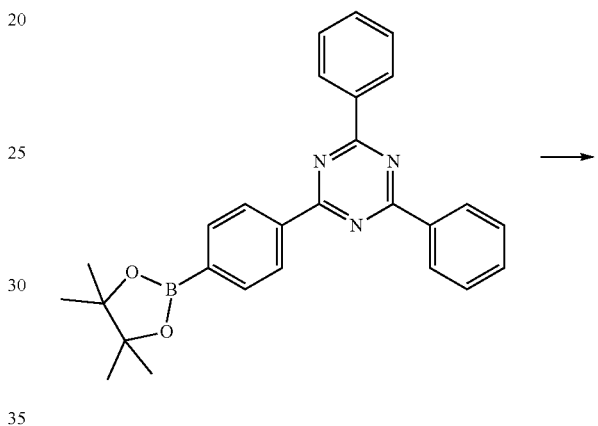

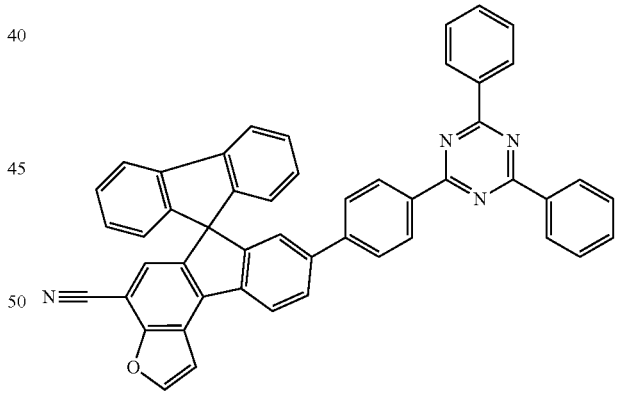
5

Compound 5 (10.7 g, yield: 87%) was prepared in the same manner as in Preparation Example 1, except that 8'-bromospiro[fluorene-9,6'-fluoreno[3,4-b]furan]-4'-carbonitrile was used instead of 6'-(4,4,5,5-tetramethyl-1,3,2-dioxaborolan-2-yl)spiro[fluorine-9,8'-fluoreno[3,4-b]benzofuran]-2-carbonitrile in Preparation Example 1, and 2,4-diphenyl-6-(4-(4,4,5,5-tetramethyl-1,3,2-dioxaboran-2-yl)phenyl)-1,3,5-triazine was used instead of 2-chloro-4,6-diphenyl-1,3,5-triazine.

MS[M+H]⁺=688

Preparation Example 6: Synthesis of Compound 6

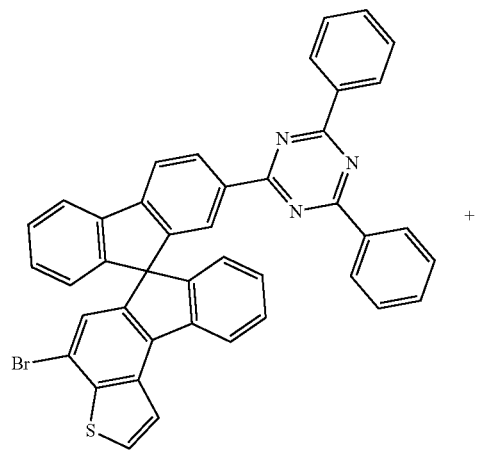

+

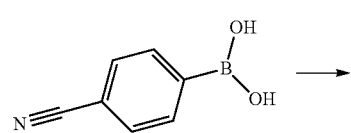

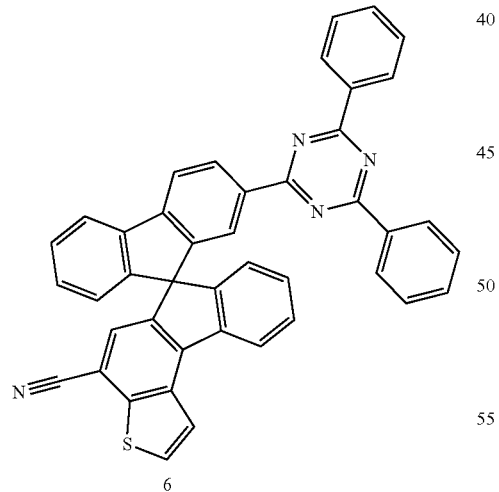

6

Compound 6 (9.7 g, yield: 77%) was prepared in the same manner as in Preparation Example 4, except that 2-(4'-bromospiro[fluorene-9,6'-fluoreno[3,4-b]thiophen]-2-yl)-4,6-diphenyl-1,3,5-triazine was used instead of 2-(4'-bromo-spiro[fluorene-9,6'-fluoreno[3,4-b]furan]-2-yl)-4,6-diphenyl-1,3,5-triazine in Preparation Example 4.

MS[M+H]$^+$=704

Preparation Example 7: Synthesis of Compound 7

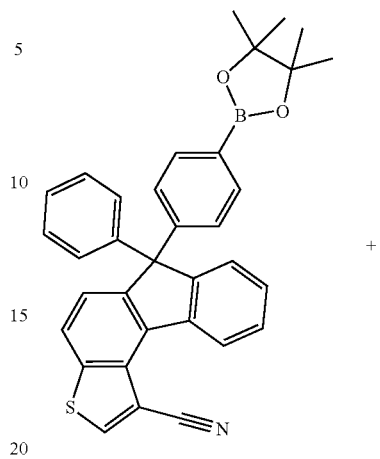

+

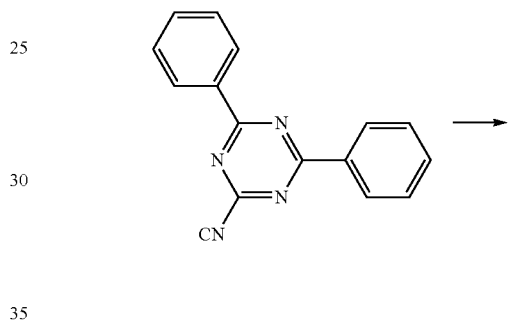

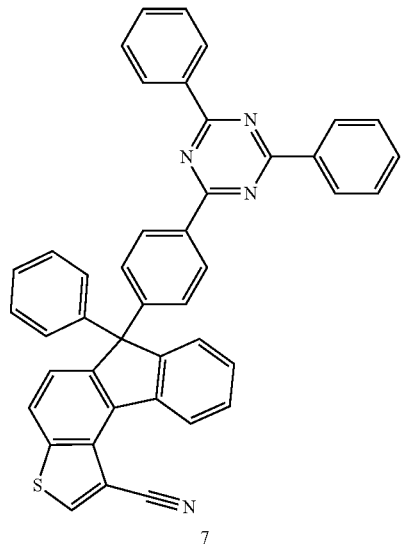

7

Compound 7 (10.1 g, yield: 89%) was prepared in the same manner as in Preparation Example 1, except that 6-phenyl-6-(4-(4,4,5,5-tetramethyl-1,3,2-dioxaboran-2-yl)phenyl)-6H-fluoreno[3,4-b]thiophene-1-carbonitrile was used instead of 6'-(4,4,5,5-tetramethyl-1,3,2-dioxaborolan-2-yl)spiro[fluorine-9,8'-fluoreno[3,4-b]benzofuran]-2-carbonitrile in Preparation Example 1.

MS[M+H]$^+$=630

Preparation Example 8: Synthesis of Compound 8

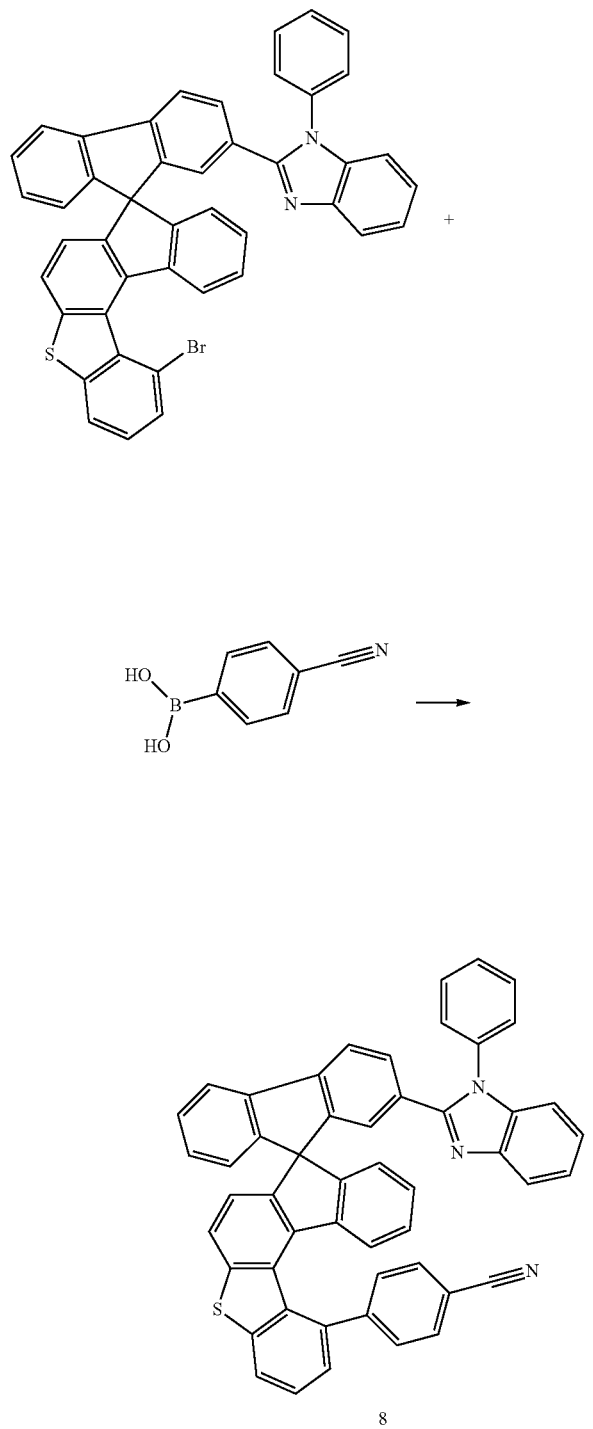

8

Preparation Example 9: Synthesis of Compound 9

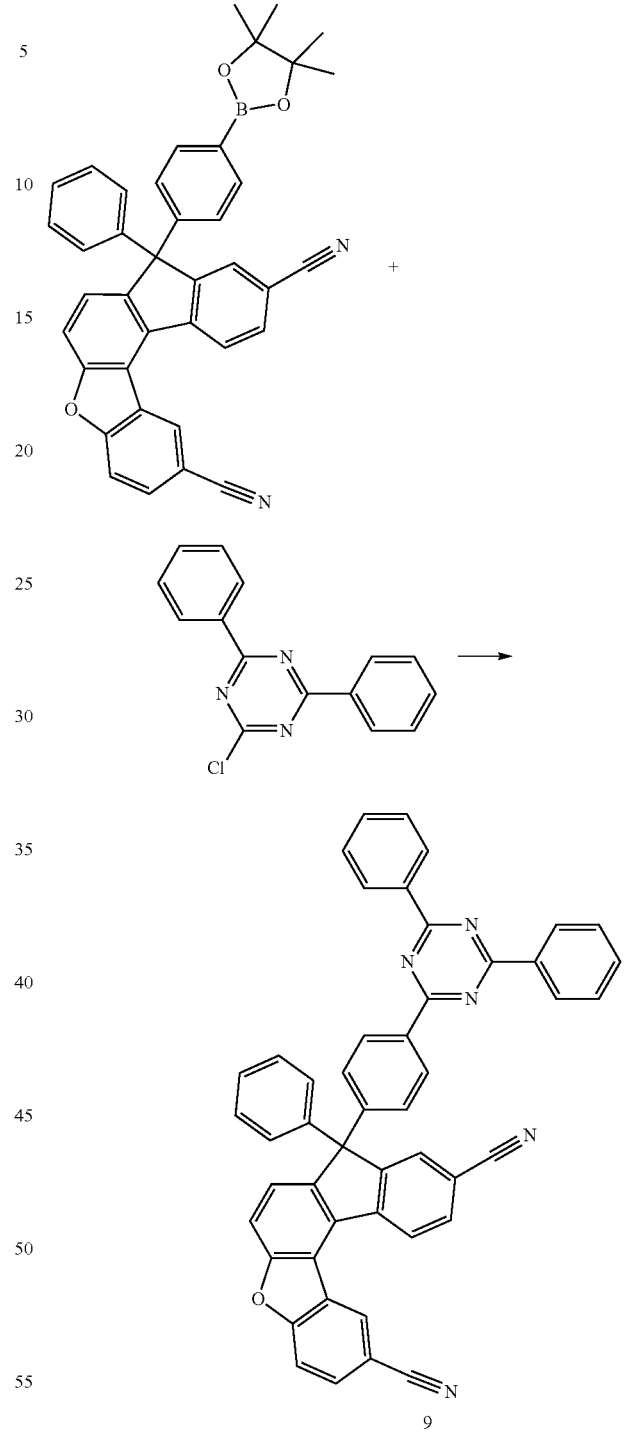

9

Compound 8 (10.5 g, yield: 82%) was prepared in the same manner as in Preparation Example 4, except that 2-(1-bromospiro[benzo[b]fluoreno[4,3-d]thiophen-8,9'-fluorene]-2'-yl)-1-phenyl-1H-benzo[d]Imidazole was used instead of 2-(4'-bromospiro[fluorene-9,6'-fluoreno[3,4-b]furan]-2-yl)-4,6-diphenyl-1,3,5-triazine in Preparation Example 4.

MS[M+H]$^+$=715

Compound 9 was prepared in the same manner as in Preparation Example 1, except that 8-phenyl-8-(4-(4,4,5,5-tetramethyl-1,3,2-dioxaborolan-2-yl)phenyl)-8H-fluoreno[3,4-b]benzofuran-2,10-dicarbonitrile was used instead of 6'-(4,4,5,5-tetramethyl-1,3,2-dioxaborolan-2-yl)spiro[fluorine-9,8'-fluoreno[3,4-b]benzofuran]-2-carbonitrile in Preparation Example 1.

MS[M+H]$^+$=689

Preparation Example 10: Synthesis of Compound 10

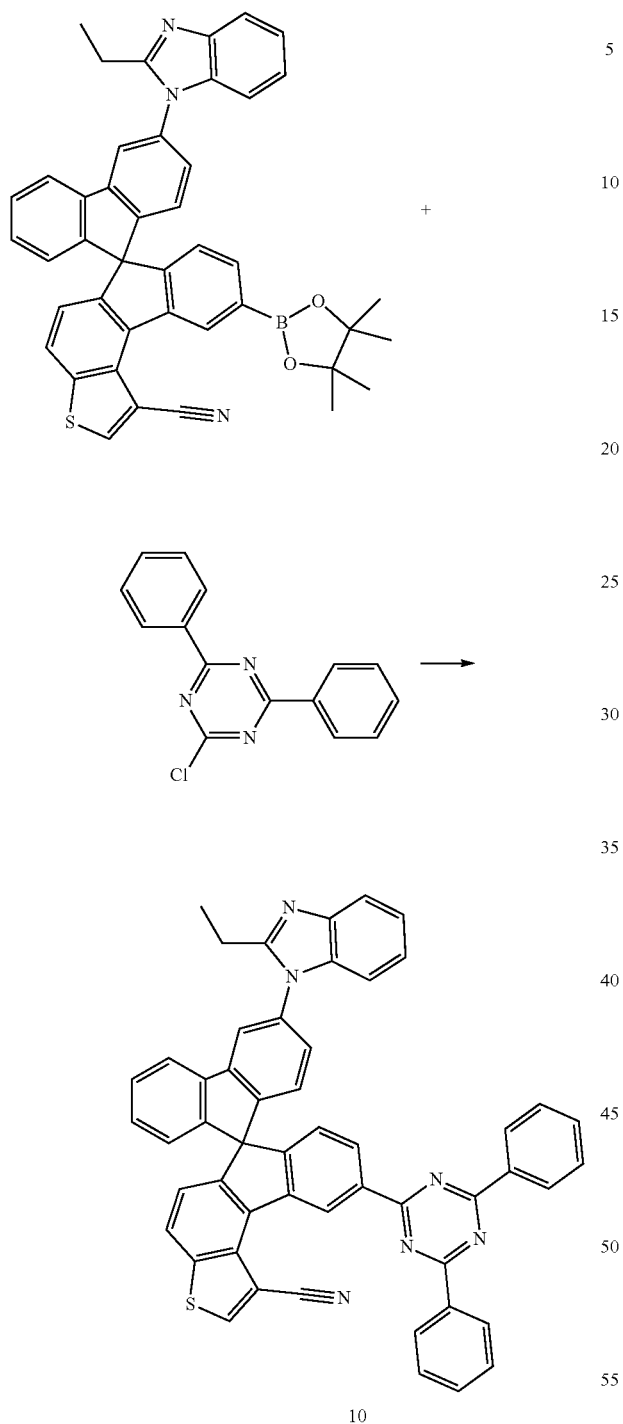

10

Compound 10 was prepared in the same manner as in Preparation Example 1, except that 3-(2-ethyl-1H-benzo[imidazol-1-yl)-9'-(4,4,5,5-tetramethyl-1,3,2-dioxaborolan-2-yl)spiro[fluorene-9,6'-fluoreno[3,4-b]thiophene]-1'-carbonitrile was used instead of 6'-(4,4,5,5-tetramethyl-1,3,2-dioxaborolan-2-yl)spiro[fluorine-9,8'-fluoreno[3,4-b]benzofuran]-2-carbonitrile in Preparation Example 1.

MS[M+H]$^+$=773

Preparation Example 11: Synthesis of Compound 11

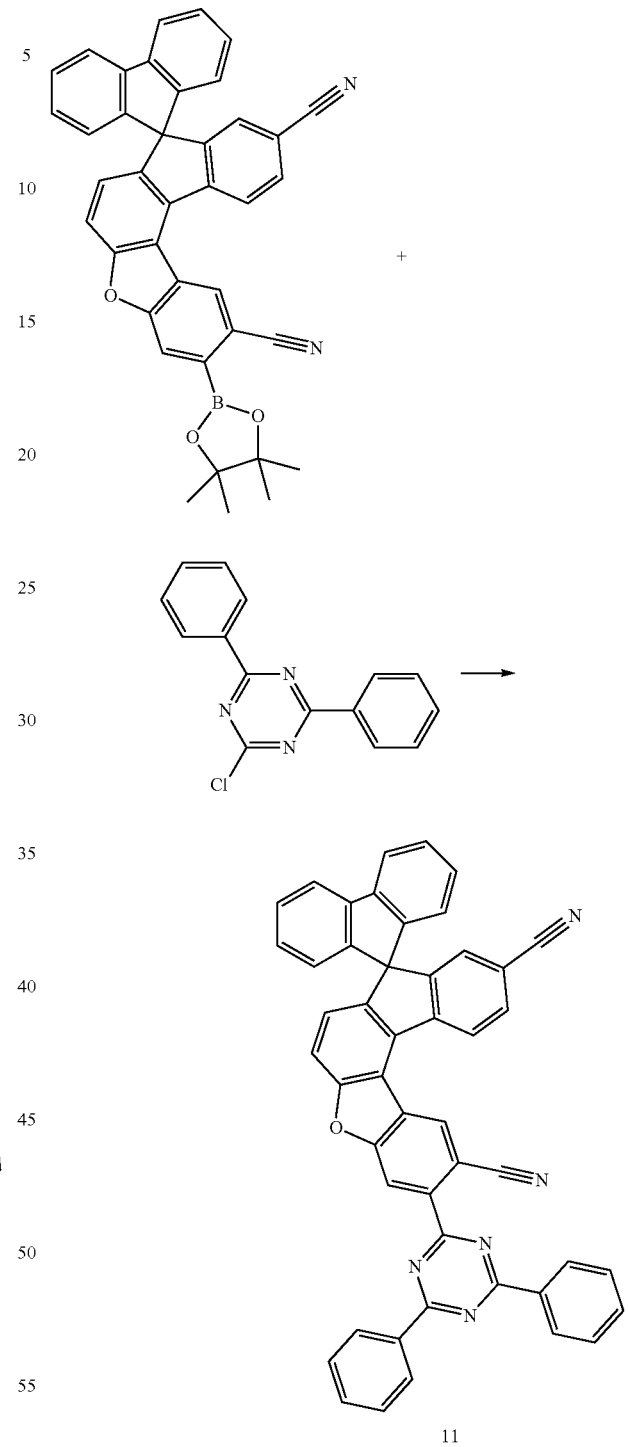

11

Compound 11 was prepared in the same manner as in Preparation Example 1, except that 3'-(4,4,5,5-tetramethyl-1,3,2-dioxaborolan-2-yl)spiro[fluorene-9,8'-fluoreno[3,4-b]benzofuran]-2',10'-dicarbonitrile was used instead of 6'-(4,4,5,5-tetramethyl-1,3,2-dioxaborolan-2-yl)spiro[fluorine-9,8'-fluoreno[3,4-b]benzofuran]-2-carbonitrile in Preparation Example 1.

MS[M+H]$^+$=687

Preparation Example 12: Synthesis of Compound 12

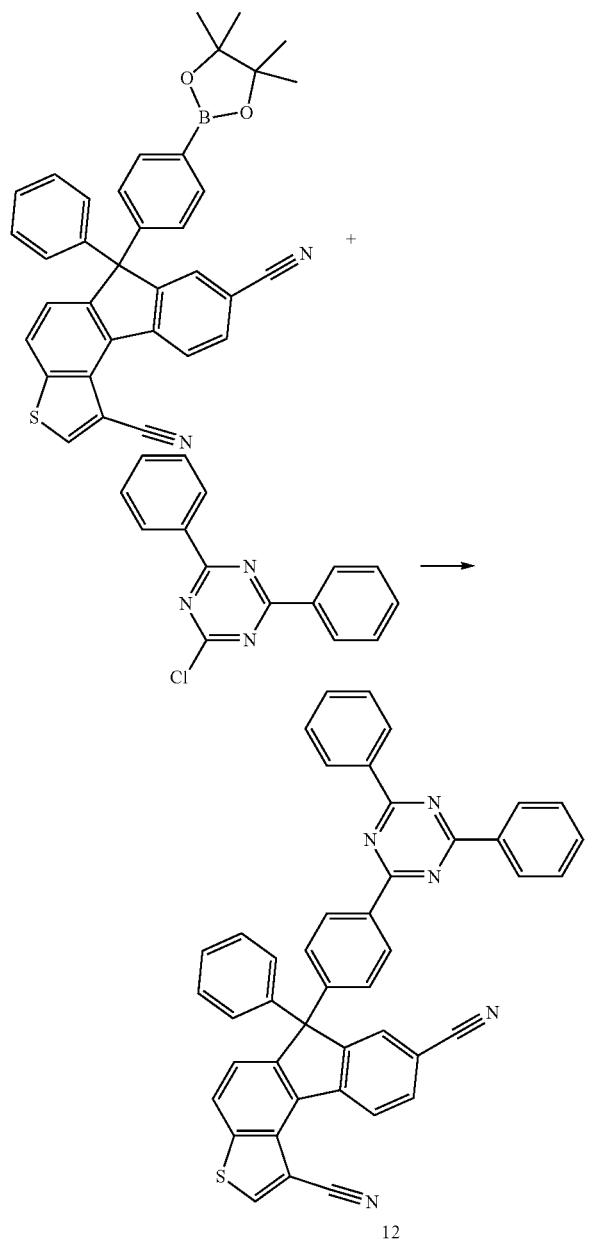

12

Compound 12 was prepared in the same manner as in Preparation Example 1, except that 6-phenyl-6-(4-(4,4,5,5-tetramethyl-1,3,2-dioxaborolan-2-yl)phenyl)-6H-fluoreno[3,4-b]thiophene-1,8-dicarbonitrile was used instead of 6'-(4,4,5,5-tetramethyl-1,3,2-dioxaborolan-2-yl)spiro[fluorine-9,8'-fluoreno[3,4-b]benzofuran]-2-carbonitrile in Preparation Example 1.

MS[M+H]$^+$=655

Example 1-1

A glass substrate on which ITO (indium tin oxide) was coated as a thin film to a thickness of 1,000 Å was put into distilled water in which a detergent was dissolved, and ultrasonically cleaned. At this time, a product manufactured by Fischer Co. was used as the detergent, and as the distilled water, distilled water filtered twice using a filter manufactured by Millipore Co. was used. After the ITO was cleaned for 30 minutes, ultrasonic cleaning was repeated twice using distilled water for 10 minutes. After the cleaning with distilled water was completed, the substrate was ultrasonically cleaned with solvents of isopropyl alcohol, acetone, and methanol, dried, and then transferred to a plasma cleaner. In addition, the substrate was cleaned for 5 minutes using oxygen plasma and then transferred to a vacuum depositor.

On the ITO transparent electrode which is the anode thus prepared, the following compound HI1 and the following compound HI2 were thermally vacuum deposited at a ratio of 98:2 (molar ratio) to have a thickness of 100 Å, thereby forming a hole injection layer. A compound represented by the following Formula HT1 (1150 Å) was vacuum-deposited on the hole injection layer to form a hole transport layer. Then, the following compound EB1 was vacuum-deposited to a thickness of 50 Å on the hole transport layer to form an electron blocking layer.

Then, a compound represented by the following Formula BH and a compound represented by the following Formula BD were vacuum-deposited at a weight ratio of 50:1 on the electron blocking layer to a thickness of 200 Å to form a light emitting layer.

A compound represented by the following Formula HB1 was vacuum-deposited to a thickness of 50 Å on the light emitting layer to form a hole blocking layer. Then, Compound 1 prepared in Preparation Example 1 and a compound of LiQ were vacuum-deposited at a weight ratio of 1:1 on the hole blocking layer to form an electron transport layer with a thickness of 30 Å. Lithium fluoride (LiF) and aluminum were sequentially deposited to have a thickness of 12 Å and 1,000 Å, respectively, on the electron transport layer, thereby forming a cathode.

In the above-mentioned process, the vapor deposition rate of the organic material was maintained at 0.4 to 0.7 Å/sec, the deposition rate of lithium fluoride of the cathode was maintained at 0.3 Å/sec, the deposition rate of aluminum was maintained at 2 Å/sec, and the degree of vacuum during the deposition was maintained at $2 \times 10^{-7}$ to $5 \times 10^{-6}$ torr, thereby manufacturing an organic light emitting device.

The structures of the compounds used in Examples are as follows.

HI1

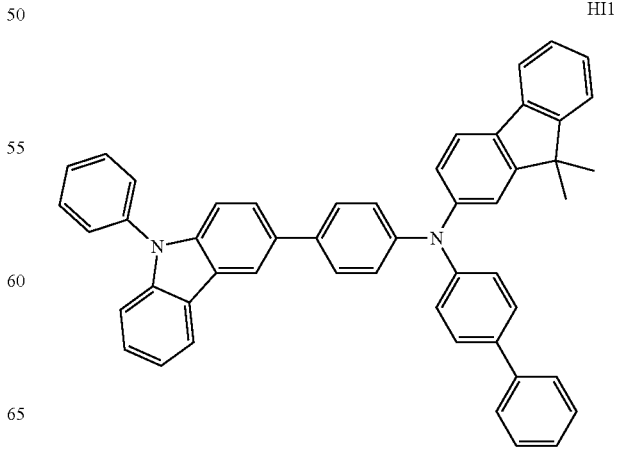

HI2
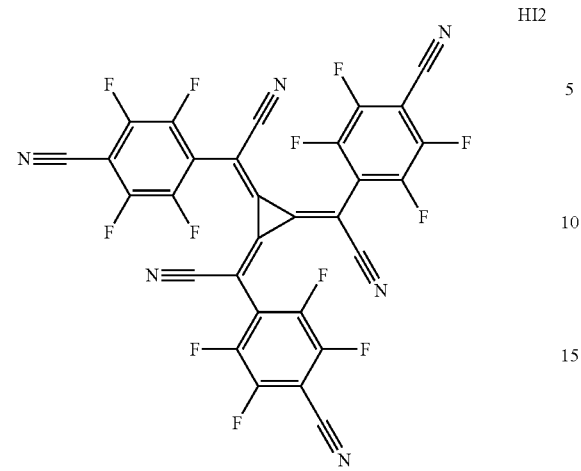
BH
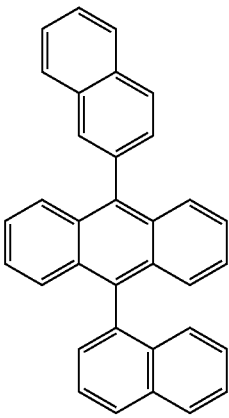
BD
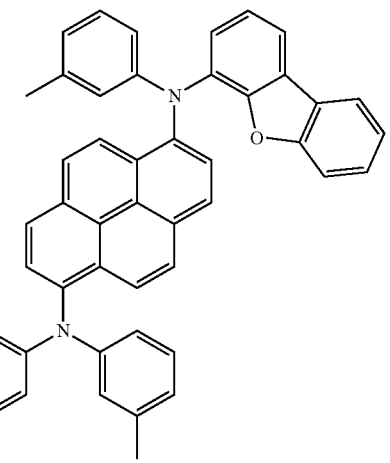
HT1
HB1
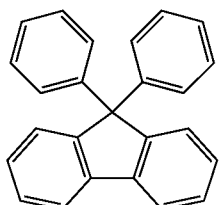
EB1
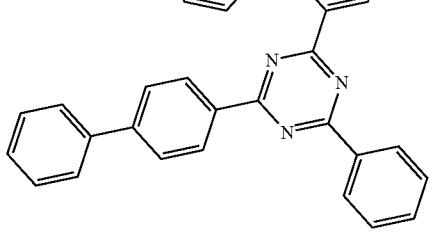
LiQ

Example 1-2 to Example 1-9
An organic light emitting device was manufactured in the same manner as in Example 1-1, except that Compounds shown in Table 1 below were used instead of the compound of Preparation Example 1.
The structures of the compounds used in Example 1-1 to Example 1-9 are as follows.
1
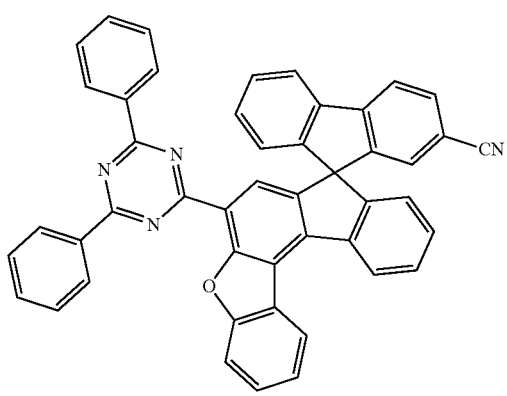
2
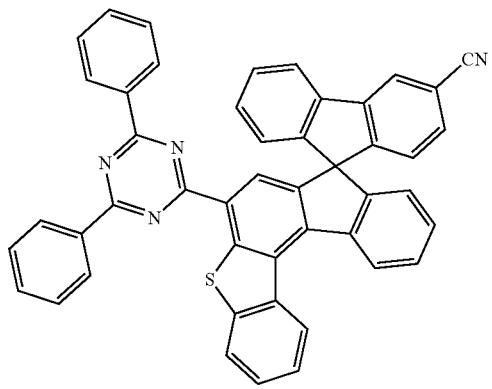
3
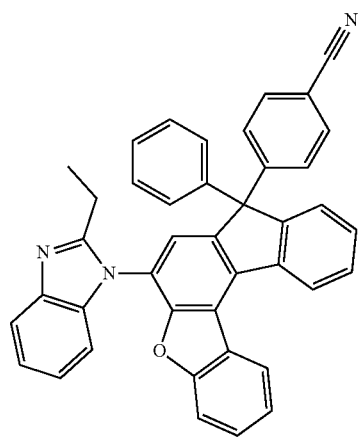
4
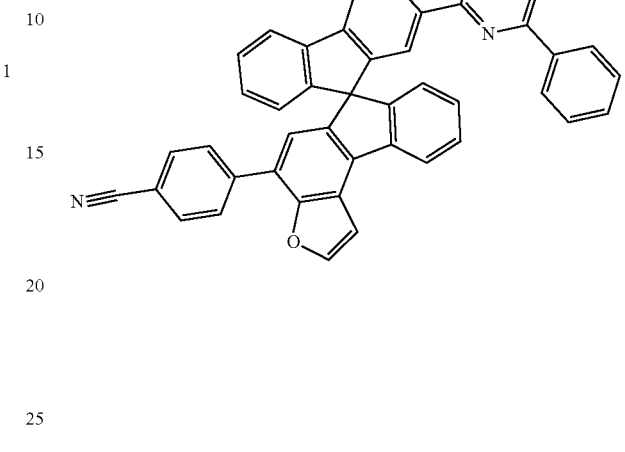
5
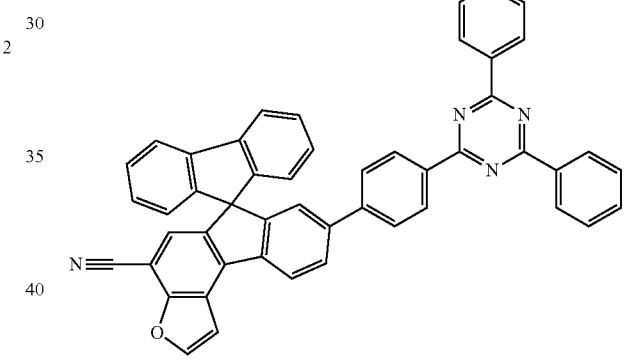
6
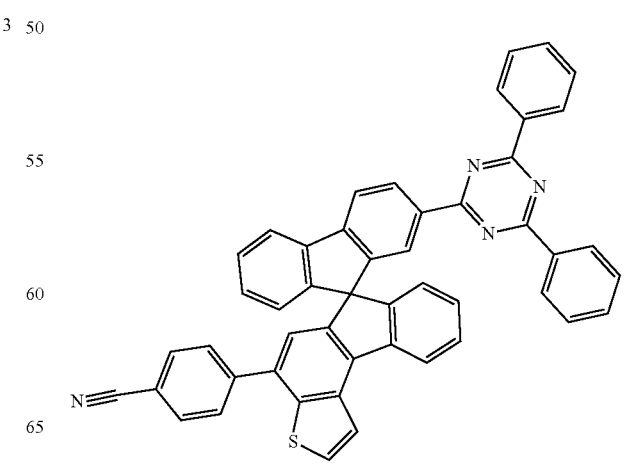

9
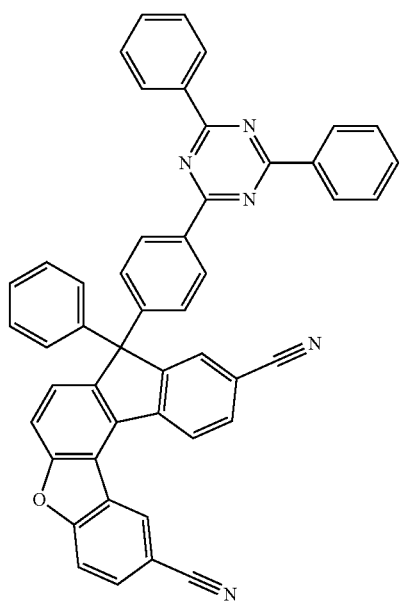
11
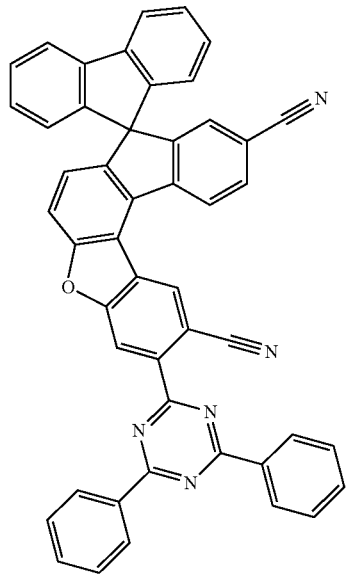
Comparative Examples 1-1 to 1-7
An organic light emitting device was manufactured in the same manner as in Example 1-1, except that Compounds shown in Table 1 below were used instead of the compound of Preparation Example 1. The structures of the compounds ET1, ET2, ET3, ET4, ET5, ET6 and ET7 used in Table 1 below are as follows.
ET1
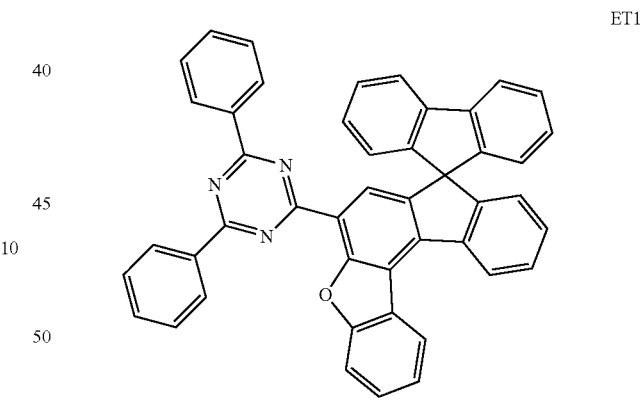
10
ET2
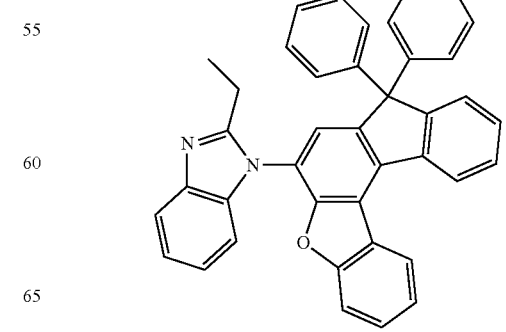
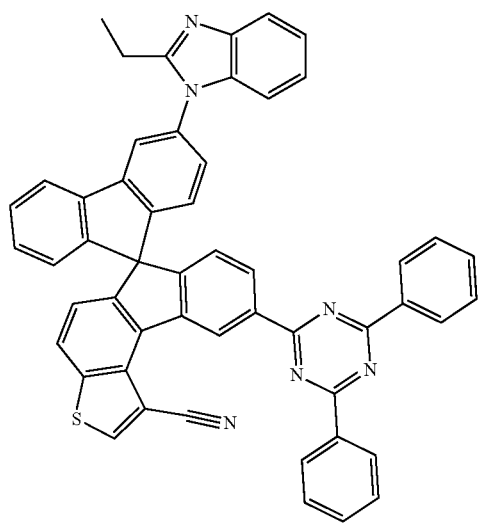

ET3

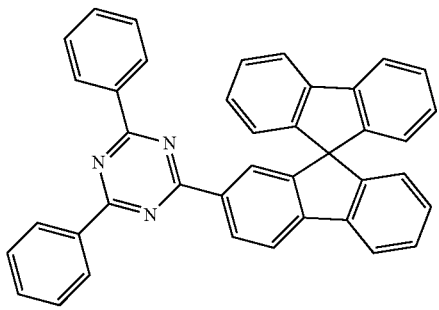

ET4

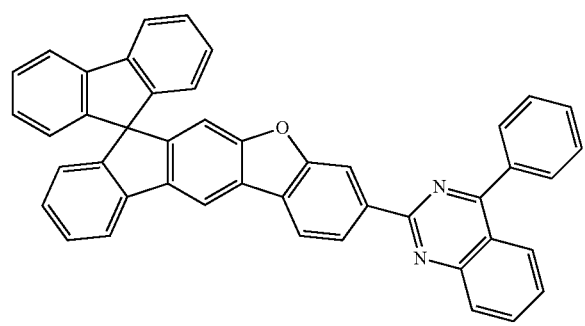

ET5

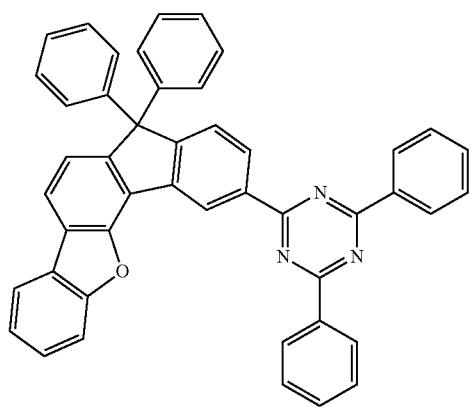

ET6

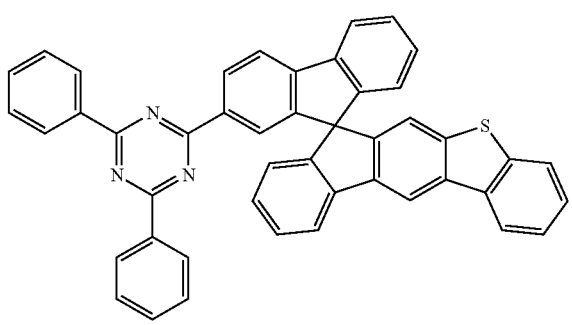

ET7

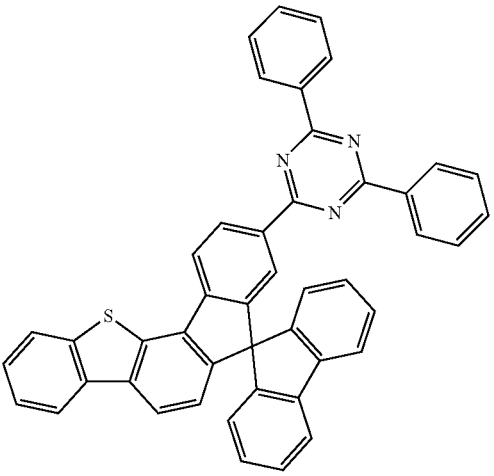

The voltage, efficiency, color coordinate, and lifetime were measured by applying a current to the organic light emitting devices manufactured in Examples 1-1 to 1-9 and Comparative Examples 1-1 to 1-7, and the results are shown in Table below. T95 means the time required for the luminance to be reduced to 95% of the initial luminance (1600 nit).

TABLE 1

| | Compound (Electron transport layer) | Voltage (V @20 mA/cm$^2$) | Efficiency (cd/A @20 mA/cm$^2$) | Color index (x, y) | T95 (hr) |
|---|---|---|---|---|---|
| Example 1-1 | Compound 1 | 4.18 | 6.24 | (0.141, 0.046) | 275 |
| Example 1-2 | Compound 2 | 4.26 | 6.21 | (0.142, 0.045) | 255 |
| Example 1-3 | Compound 3 | 4.78 | 6.58 | (0.143, 0.047) | 244 |
| Example 1-4 | Compound 4 | 4.24 | 6.91 | (0.143, 0.046) | 254 |
| Example 1-5 | Compound 5 | 4.12 | 6.54 | (0.144, 0.044) | 270 |
| Example 1-6 | Compound 6 | 4.11 | 6.43 | (0.141, 0.047) | 234 |
| Example 1-7 | Compound 9 | 4.42 | 6.45 | (0.142, 0.046) | 221 |
| Example 1-8 | Compound 10 | 4.31 | 6.12 | (0.141, 0.047) | 236 |
| Example 1-9 | Compound 11 | 4.29 | 6.27 | (0.141, 0.046) | 242 |
| Comparative Example 1-1 | Compound ET1 | 4.43 | 5.66 | (0.145, 0.049) | 194 |
| Comparative Example 1-2 | Compound ET2 | 4.98 | 5.42 | (0.148, 0.051) | 142 |
| Comparative Example 1-3 | Compound ET3 | 5.53 | 5.19 | (0.146, 0.053) | 98 |
| Comparative Example 1-4 | Compound ET4 | 4.69 | 5.74 | (0.146, 0.052) | 167 |
| Comparative Example 1-5 | Compound ET5 | 4.92 | 5.89 | (0.145, 0.050) | 159 |
| Comparative Example 1-6 | Compound ET6 | 5.11 | 6.11 | (0.145, 0.052) | 117 |
| Comparative Example 1-7 | Compound ET7 | 4.58 | 5.61 | (0.146, 0.051) | 148 |

As shown in Table 1, the organic light emitting device manufactured by using the compound of the present disclosure as the electron transport layer exhibited excellent characteristics in terms of efficiency, driving voltage and stability of the organic light emitting device.

In particular, it was confirmed that the organic light emitting devices of Examples employing the compound represented by the Chemical Formula 1 exhibited equal or lower driving voltage, higher efficiency and significantly improved life characteristics, as compared with not only the organic light-emitting device of Comparative Examples 1-3 employing the existing spirobifluorene core compound but also the organic light emitting devices of Comparative Example 1-1, Comparative Example 1-2 and Comparative Example 1-4 and Comparative Example 1-7 employing compounds having no cyano group even if they have the same or similar cores.

DESCRIPTION OF REFERENCE NUMBERS

1: substrate
2: anode
3: hole transport layer
4: light emitting layer
5: electron transport layer
6: cathode
7: hole injection layer
8: electron blocking layer
9: hole blocking layer
10: electron injection layer

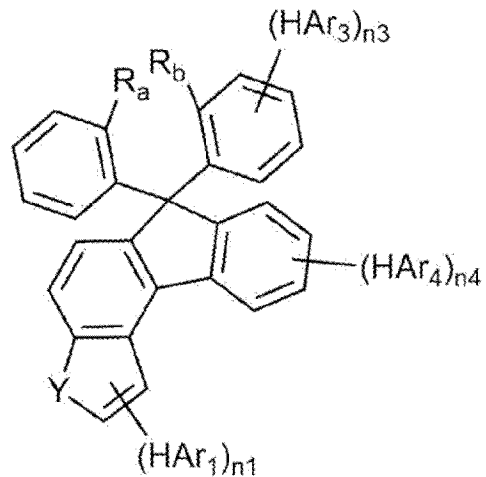

The invention claimed is:
1. A compound of Chemical Formula 1:

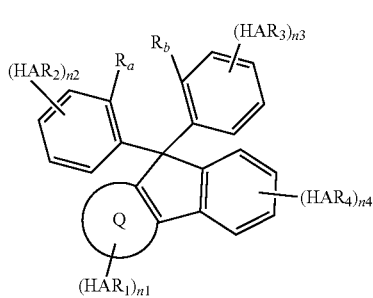

[Chemical Formula 1]

wherein in Chemical Formula 1:

Q is dibenzofuran, dibenzothiophene, benzofuran, or benzothiophene ring;

$R_a$ and $R_b$ are each hydrogen, or are combined together to form a single bond;

one of $HAr_1$ to $HAr_4$ is one of the following Chemical Formulae 2-1 to 2-3, another one is the following Chemical Formula 3, and the remaining are one of the following Chemical Formulae 2-1 to 2-3 or 3:

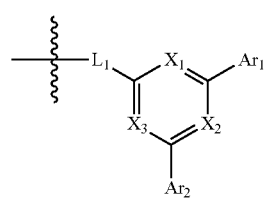

[Formula 2-1]

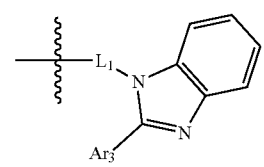

[Formula 2-2]

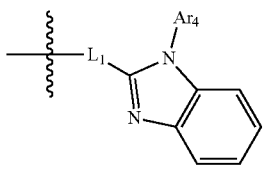

[Formula 2-3]

wherein in Chemical Formulae 2-1 to 2-3:

$X_1$ to $X_3$ are each independently N or CH, and at least two of $X_1$ to $X_3$ are N;

$Ar_1$ to $Ar_4$ are each independently hydrogen, deuterium, a substituted or unsubstituted $C_{1-60}$ alkyl, a substituted or unsubstituted $C_{3-60}$ cycloalkyl, a substituted or unsubstituted $C_{6-60}$ aryl, or a substituted or unsubstituted $C_{2-60}$ heteroaryl containing one or more heteroatoms selected from the group consisting of N, O and S; and $L_1$ is a single bond or an unsubstituted $C_{6-60}$ arylene;

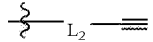

[Chemical Formula 3]

wherein in Chemical Formula 3:

$L_2$ is a single bond or an unsubstituted $C_{6-60}$ arylene;

n1 to n4 are each an integer of 0 to 2, and n1+n2+n3+n4 is an integer of 2 to 8.

2. The compound of claim 1, wherein $X_1$ to $X_3$ are N.

3. The compound of claim 1, wherein $Ar_1$ and $Ar_2$ are phenyl, $Ar_3$ is ethyl, and $Ar_4$ is phenyl.

4. The compound of claim 1, wherein $L_1$ and $L_2$ are a single bond or phenylene.

5. The compound of claim 1, wherein the compound is any one of Chemical Formulae 4-1 to 4-4:

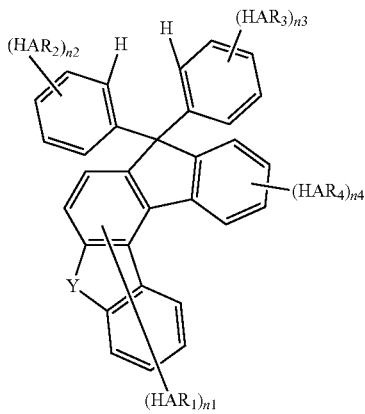

[Chemical Formula 4-1]

[Chemical Formula 4-2]

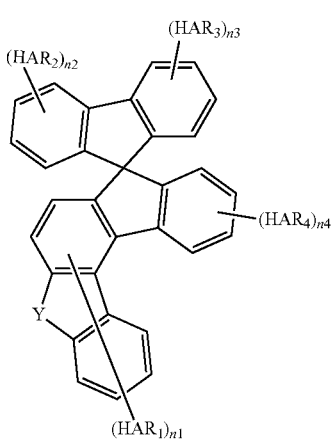

[Chemical Formula 5-1]

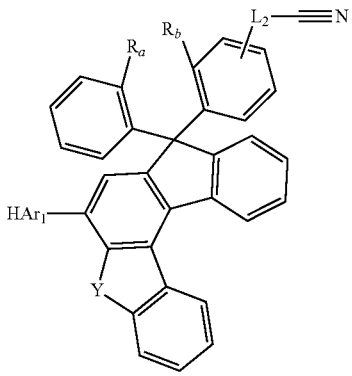

[Chemical Formula 4-3]

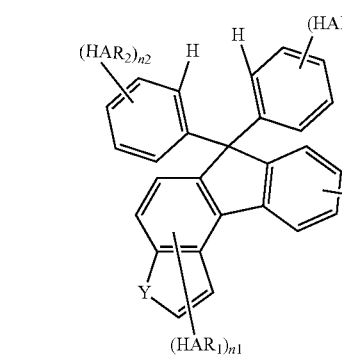

Chemical Formula 5-2

[Chemical Formula 4-4]

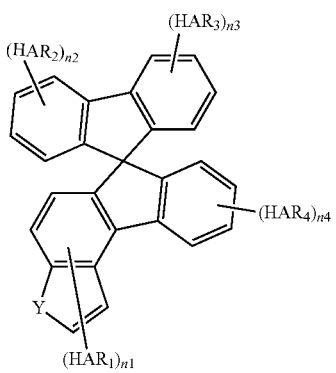

wherein in Chemical Formulas 5-1 and 5-2:

$R_a$ and $R_b$ are each hydrogen, or are combined together to form a single bond;

Y is O or S;

$HAr_1$ is any one of Chemical Formulae 2-1 to 2-3; and $L_2$ is a single bond or 1,4-phenylene.

9. The compound of claim 1, wherein the compound is any one of Chemical Formula 5-3 or 5-4:

wherein in Chemical Formulae 4-1 to 4-4:

Y is O or S;

n1 to n4 are each 0 or 1;

n1+n2+n3+n4 is 2;

one of $HAr_1$ to $HAr_4$ is any one of Chemical Formulae 2-1 to 2-3, and the other one is Chemical Formula 3.

6. The compound of claim 1, wherein n1+n2+n3+n4 is 2 or 3.

7. The compound of claim 1, wherein:

n1 and n2 are each 1, and n3 and n4 are each 0; or n1 and n3 are each 1, and n2 and n4 are each 0; or n1 and n4 are each 1, and n2 and n3 are each 0.

8. The compound of claim 1, wherein the compound is any one of Chemical Formula 5-1 or 5-2:

Chemical Formula 5-3

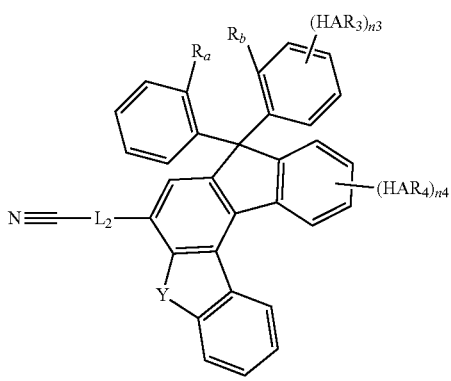

-continued

Chemical Formula 5-4

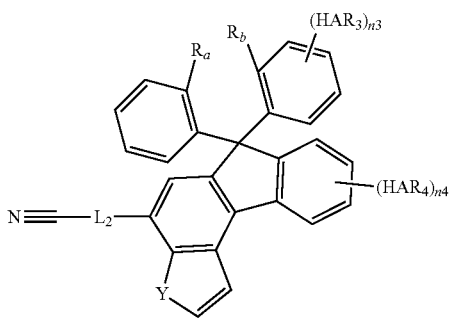

wherein in Chemical Formulas 5-3 and 5-4;
$R_a$ and $R_b$ are each hydrogen, or are combined together to form a single bond;
Y is O or S;
$L_2$ is a single bond or 1,4-phenylene;
n3 and n4 are each 0 or 1;
n3+n4 is 1; and
one of HAr$_3$ and HAr$_4$ is any one of Chemical Formulae 2-1 to 2-3.

10. The compound of claim 1,
wherein the compound is any one of Chemical Formula 5-5 or 5-6:

Chemical Formula 5-5

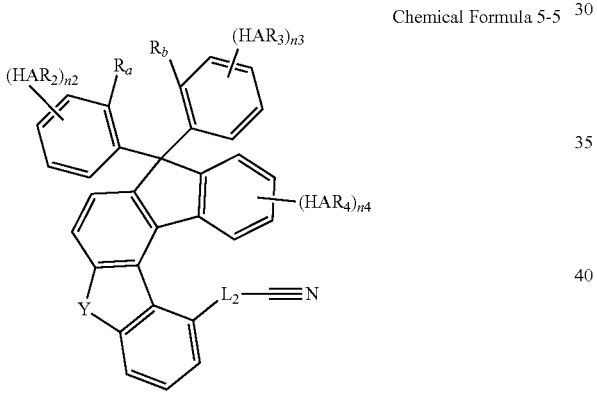

Chemical Formula 5-6

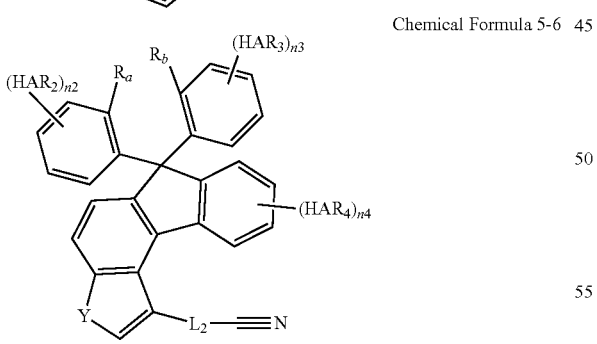

wherein in Chemical Formulas 5-5 and 5-6:
$R_a$ and $R_b$ are each hydrogen, or are combined together to form a single bond;
Y is O or S;
$L_2$ is a single bond or 1,4-phenylene;
n2 to n4 are each 0 or 1;
n2+n3+n4 is 1; and
one of HAr$_2$ to HAr$_4$ is any one of Chemical Formulae 2-1 to 2-3.

11. The compound of claim 1,
wherein n1, n2 and n3 are each 1, and n4 is 0; or
n1, n2 and n4 are each 1, and n3 is 0; or
n1, n3 and n4 are each 1, and n2 is 0; or
n2, n3 and n4 are each 1, and n1 is 0; or
n1 is 2, n2 is 1, and n3 and n4 are each 0; or
n1 is 2, n3 is 1, and n2 and n4 are each 0; or
n1 is 2, n4 is 1, and n2 and n3 is each 0.

12. The compound of claim 1,
wherein the compound is any one of Chemical Formula 6-1 or 6-2:

Chemical Formula 6-1

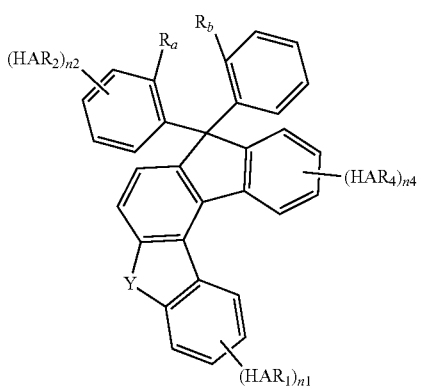

Chemical Formula 6-2

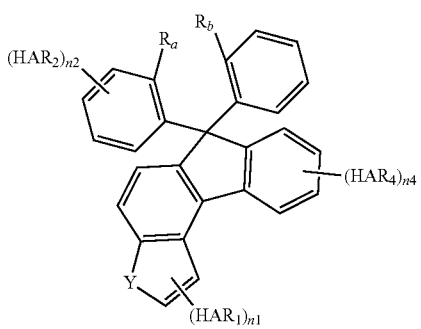

wherein in Chemical Formulas 6-1 and 6-2:
$R_a$ and $R_b$ are each hydrogen, or are combined together to form a single bond;
Y is O or S;
n1, n2 and n4 are each 0, 1, or 2;
n1+n2+n4 is 2;
one of HAr$_1$, HAr$_2$, and HAr$_4$ is any one of Chemical Formulae 2-1 to 2-3, and another one is Chemical Formula 3.

13. The compound of claim 1,
wherein the compound is any one of Chemical Formula 6-3 or 6-4:

Chemical Formula 6-3

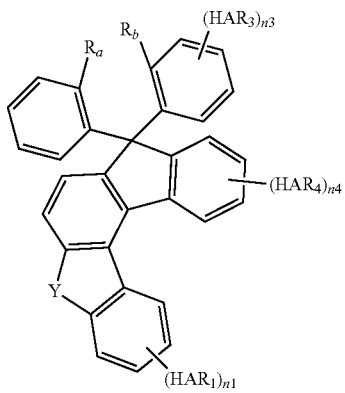

Chemical Formula 6-4

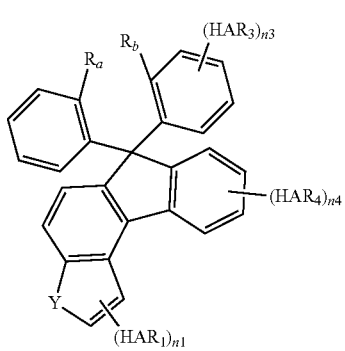

wherein in Chemical Formulas 6-3 and 6-4;

$R_a$ and $R_b$ are each hydrogen, or are combined together to form a single bond;

Y is O or S;

n1, n3 and n4 are each 0, 1, or 2;

n1+n3+n4 is 2; and one of $HAr_1$, $HAr_3$, and $HAr_4$ is anyone of Chemical Formulae 2-1 to 2-3, and another one is Chemical Formula 3.

14. A compound selected from the group consisting of the following compounds:

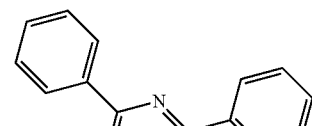
-continued

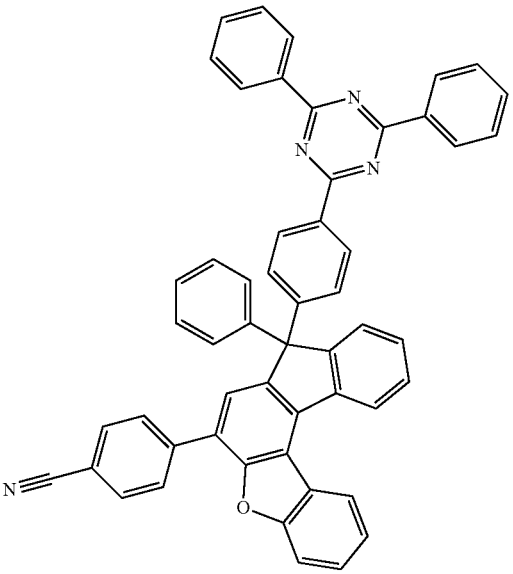

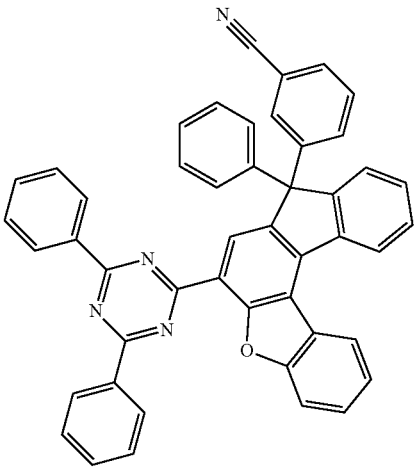

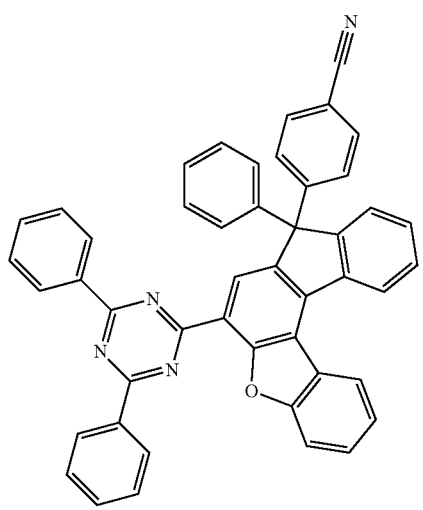

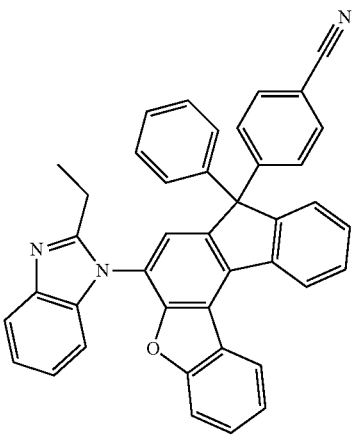

99
-continued
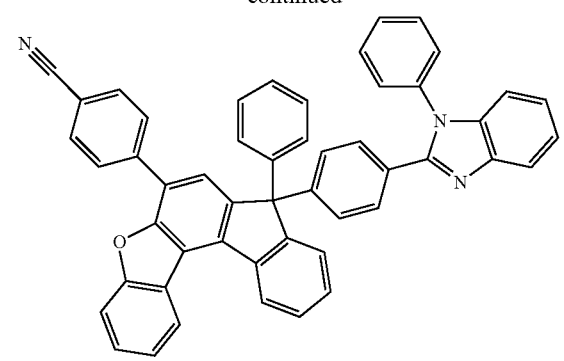
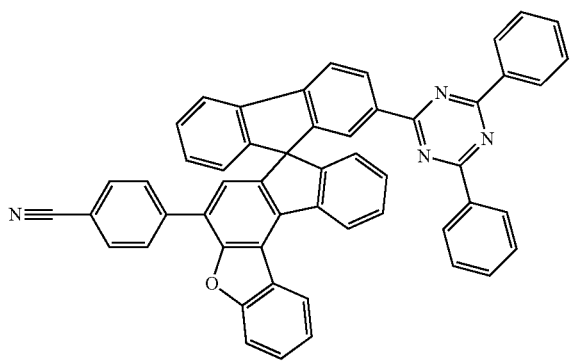
100
-continued
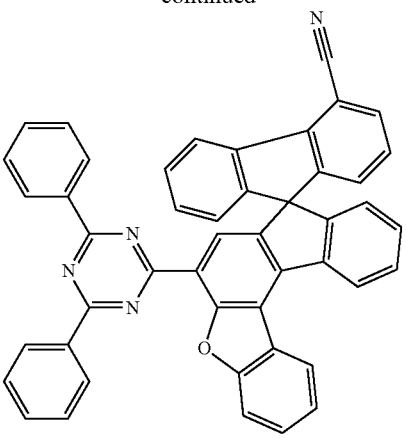
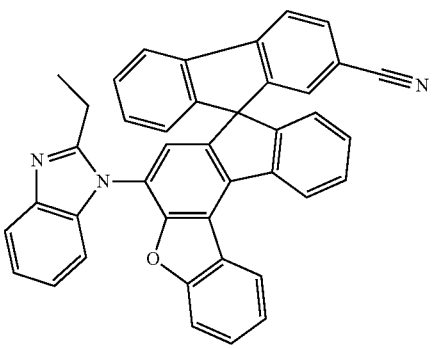
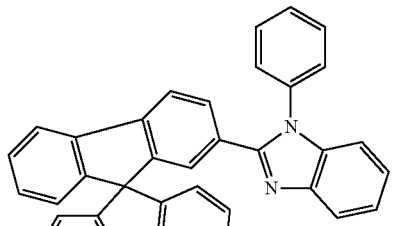
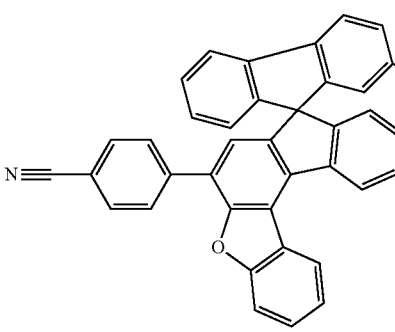

101
-continued
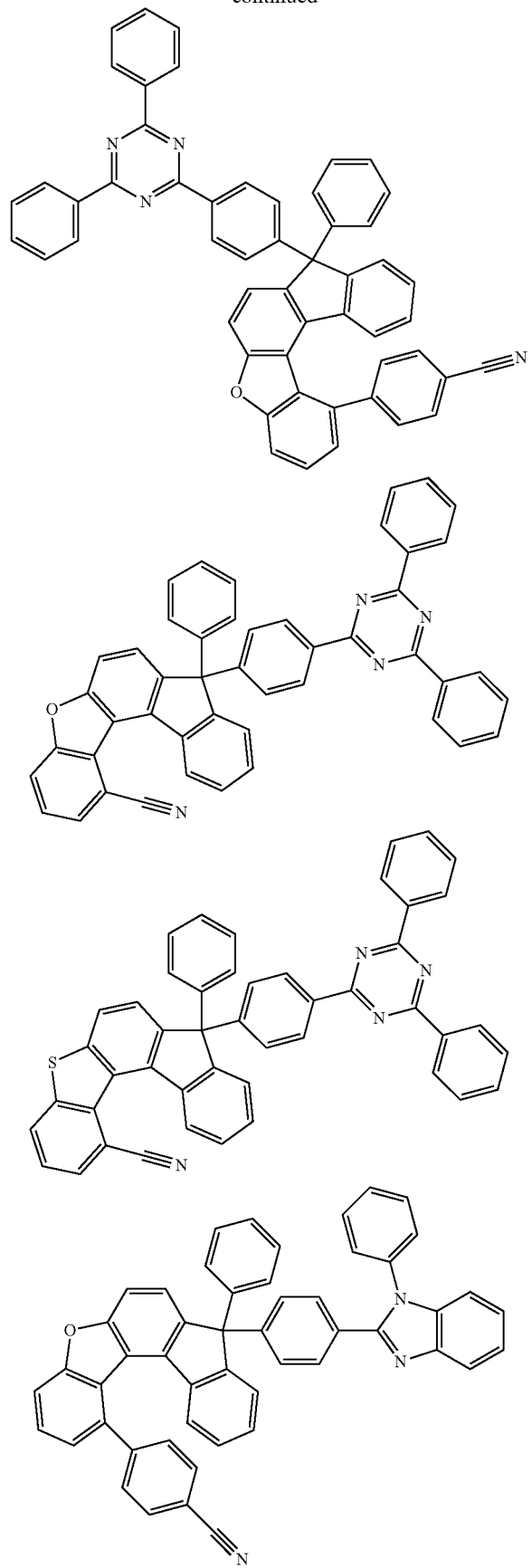
102
-continued
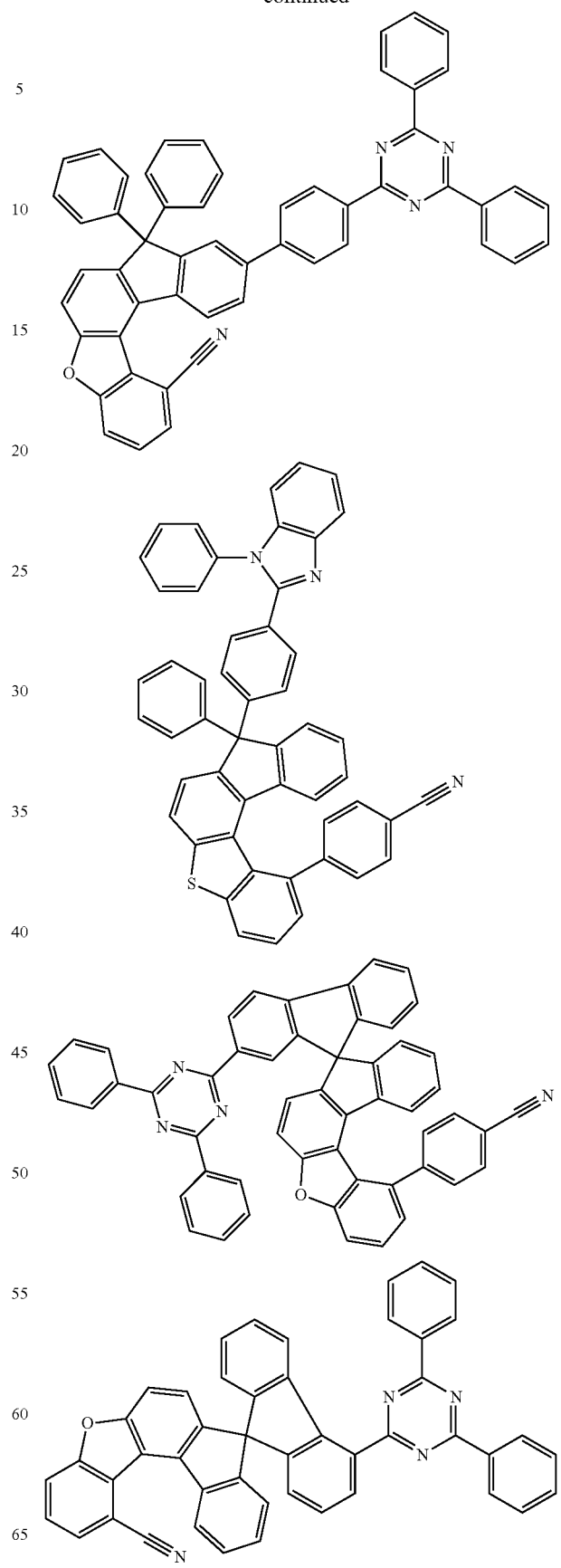

103
-continued
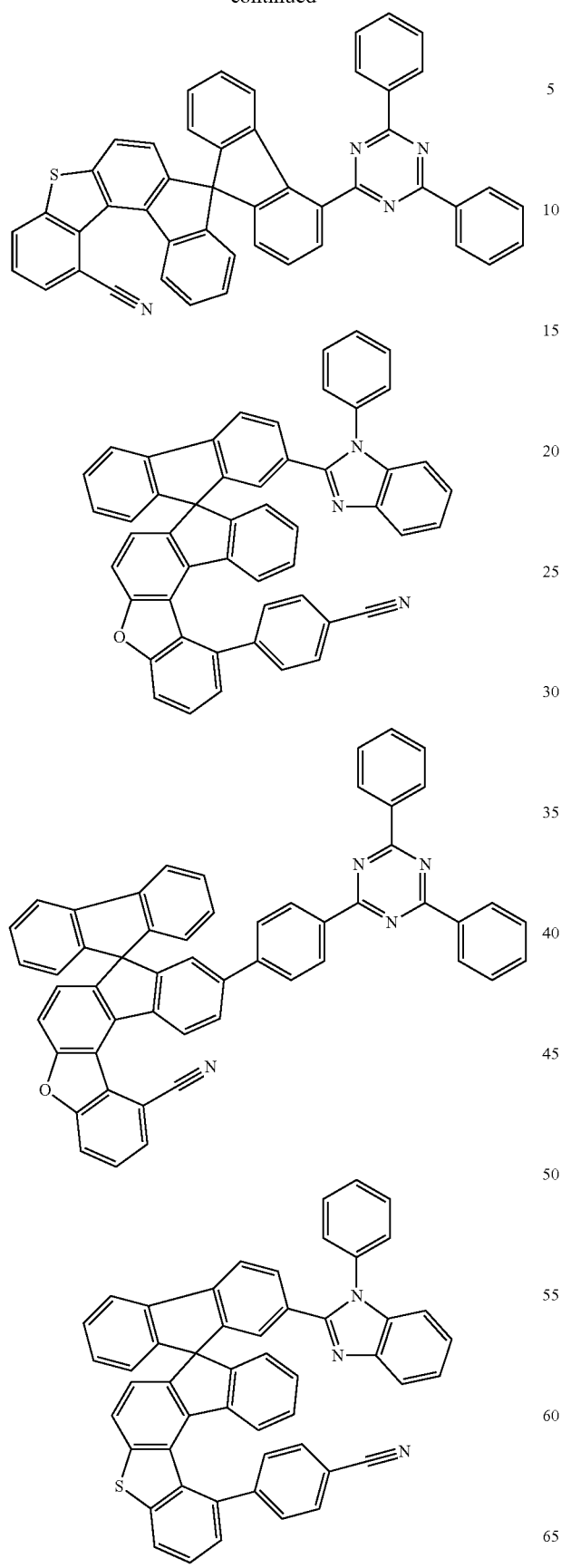
104
-continued
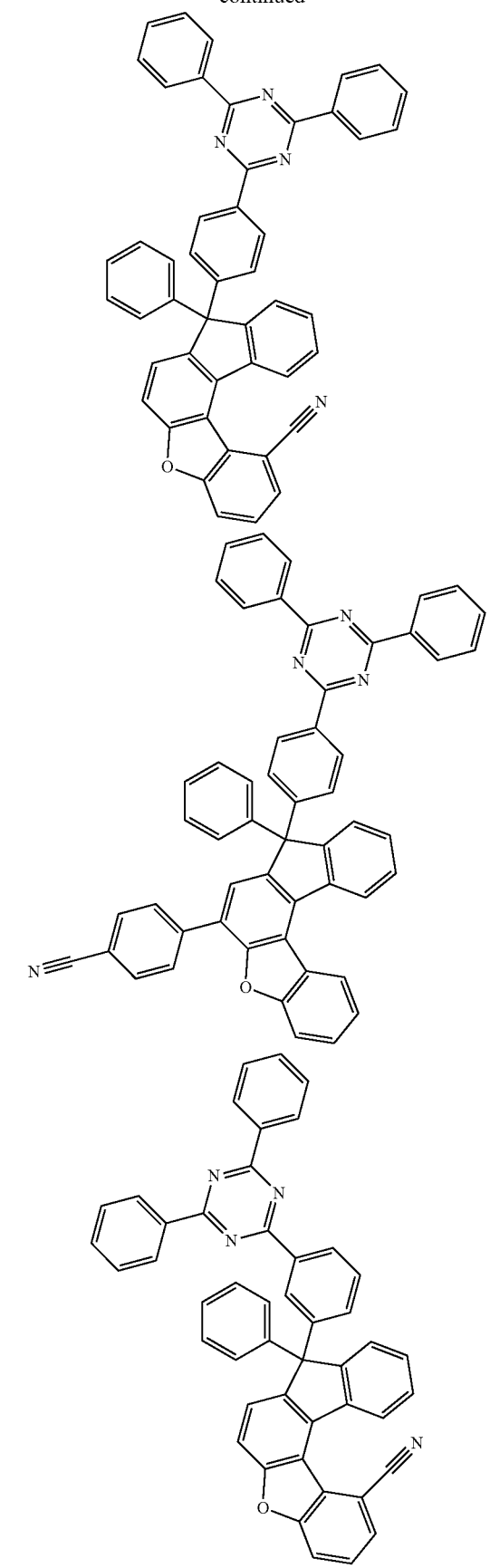

105
-continued
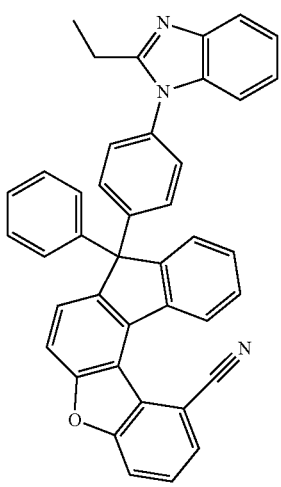
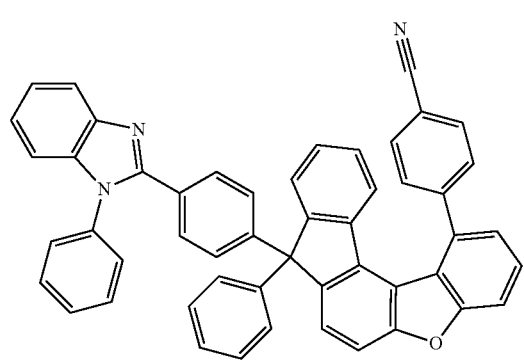
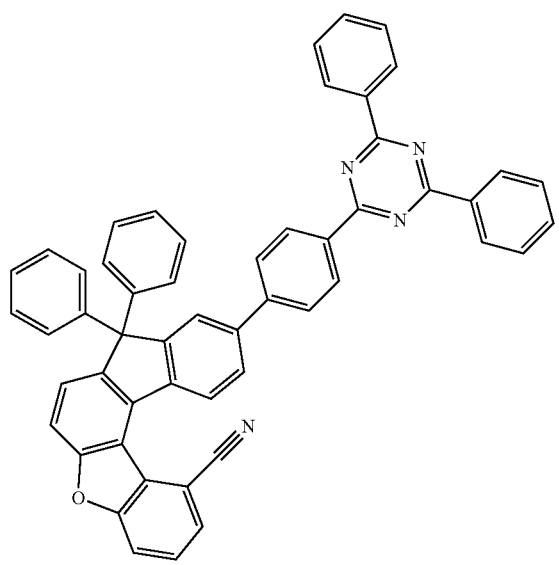
106
-continued
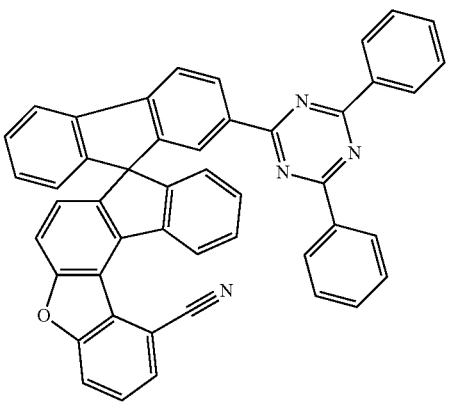
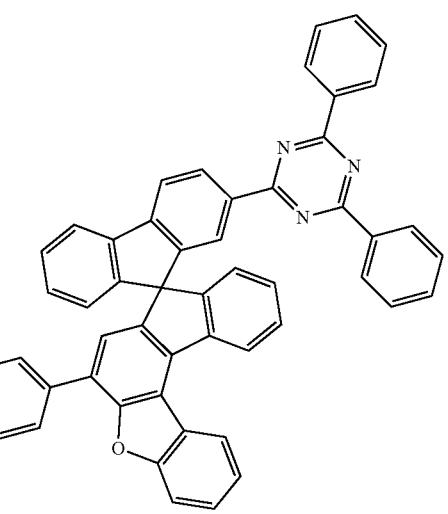
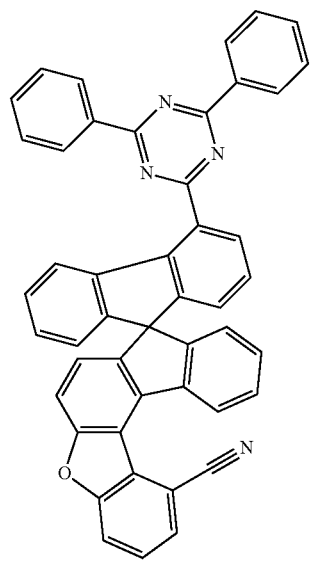

107
-continued
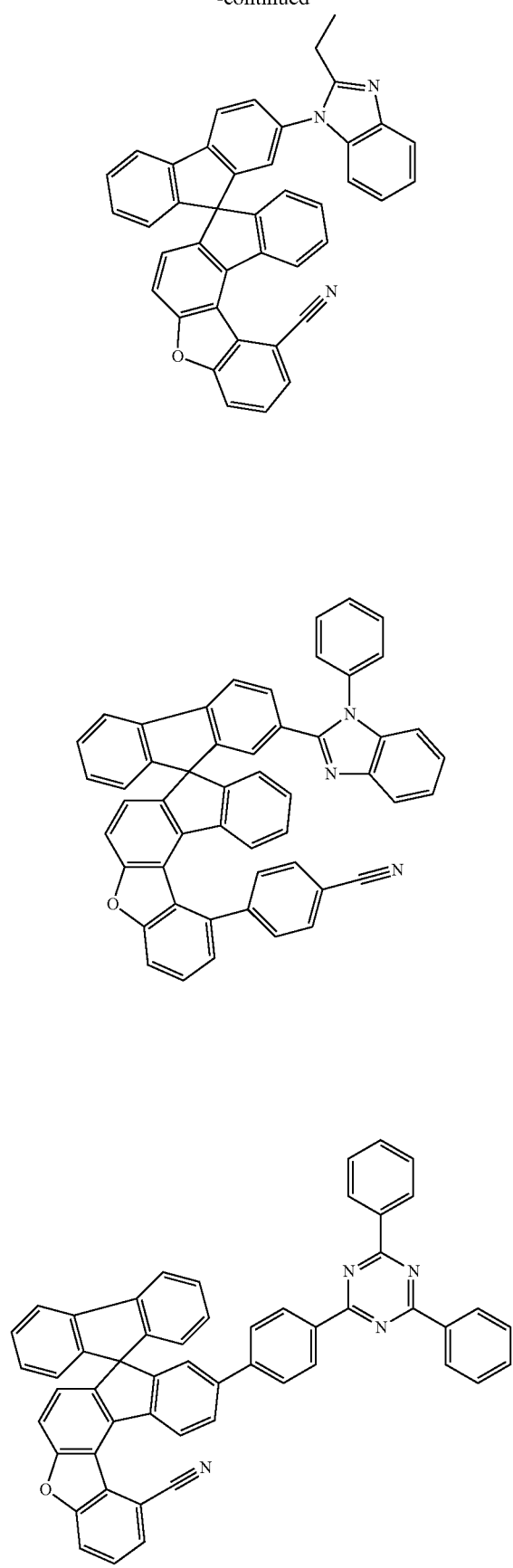
108
-continued
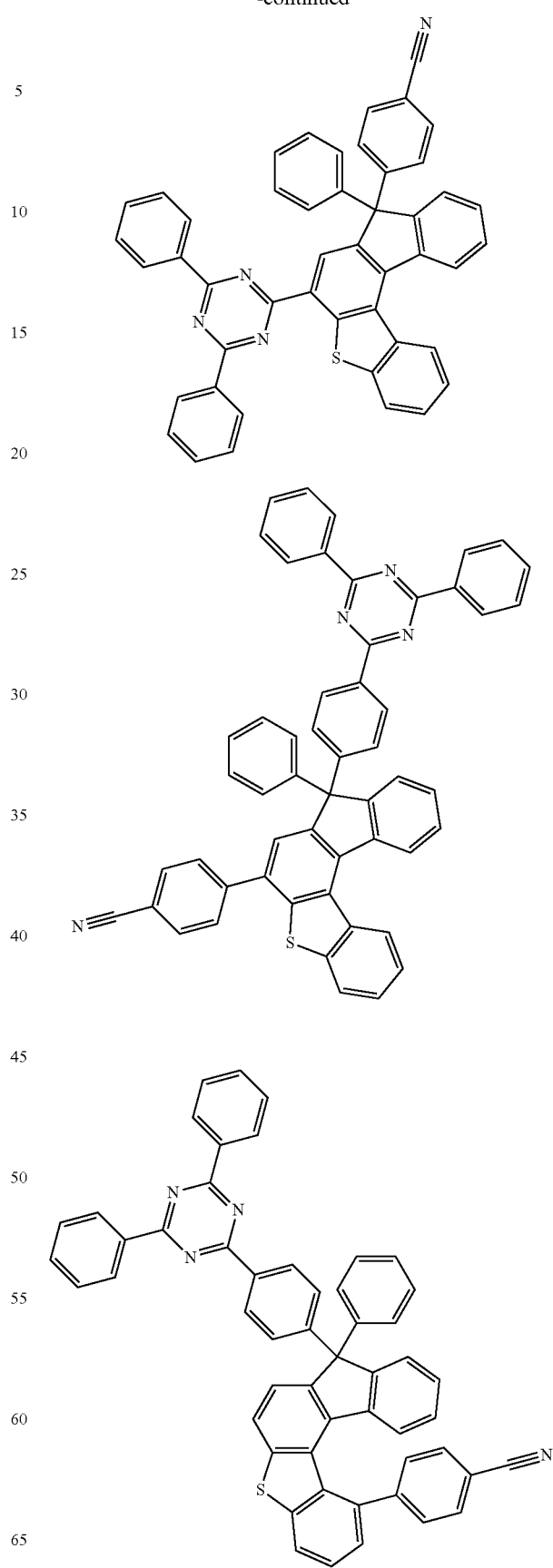

109
-continued
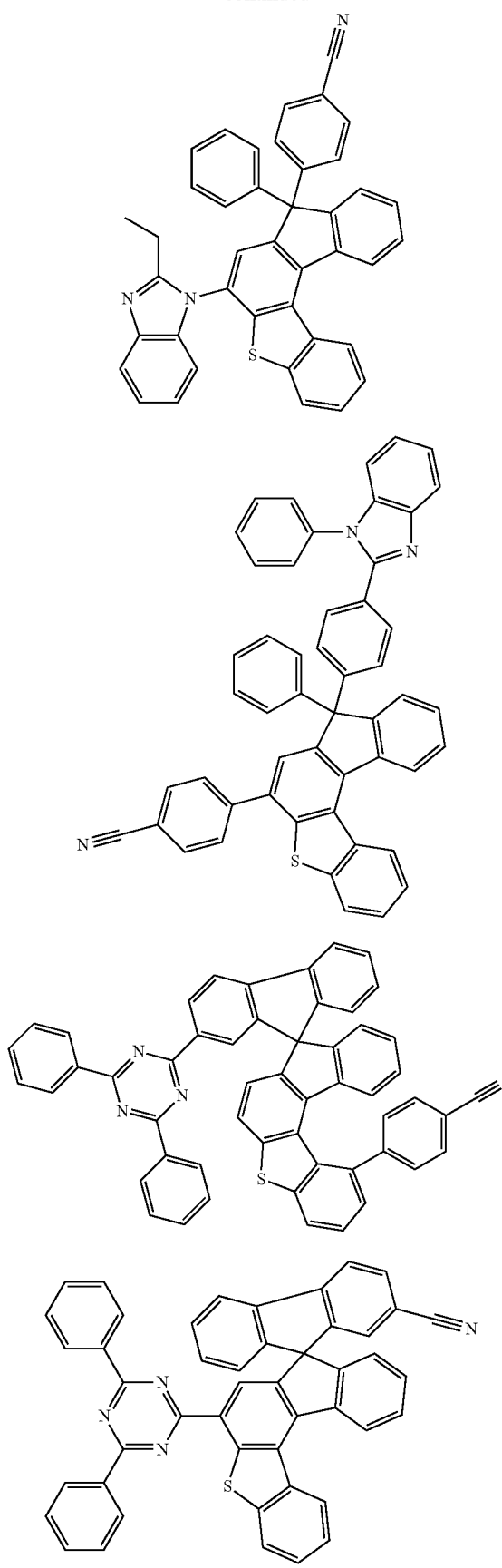
110
-continued
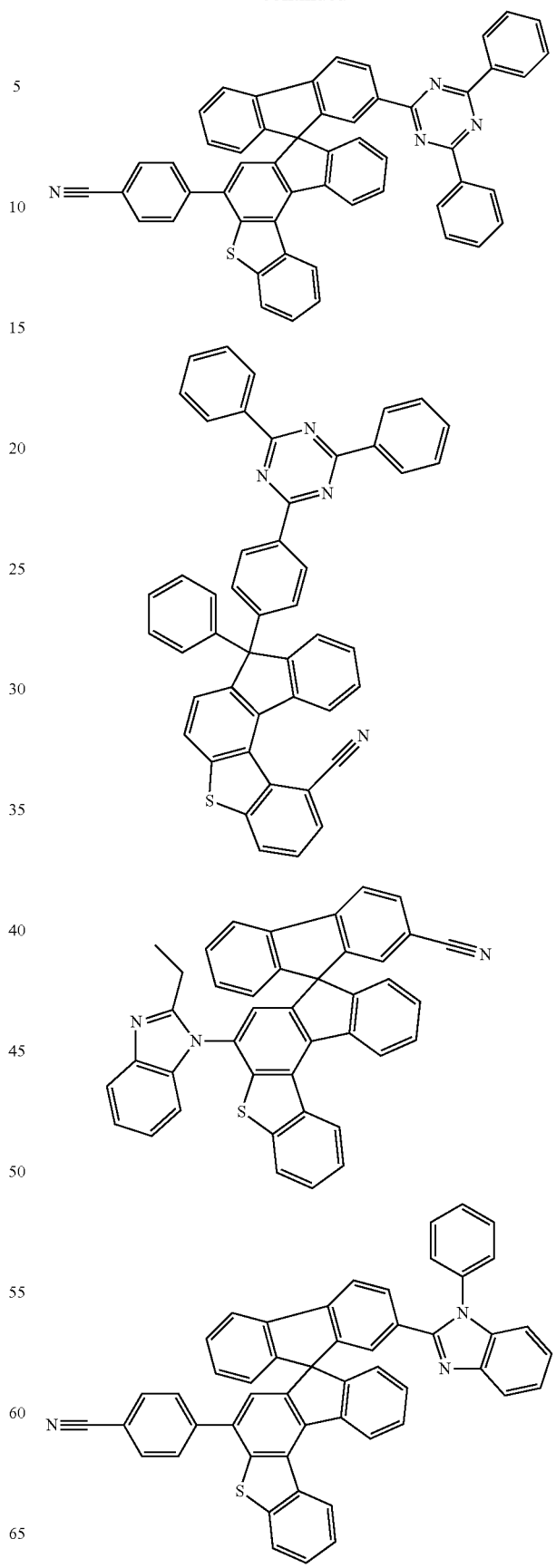

111
-continued
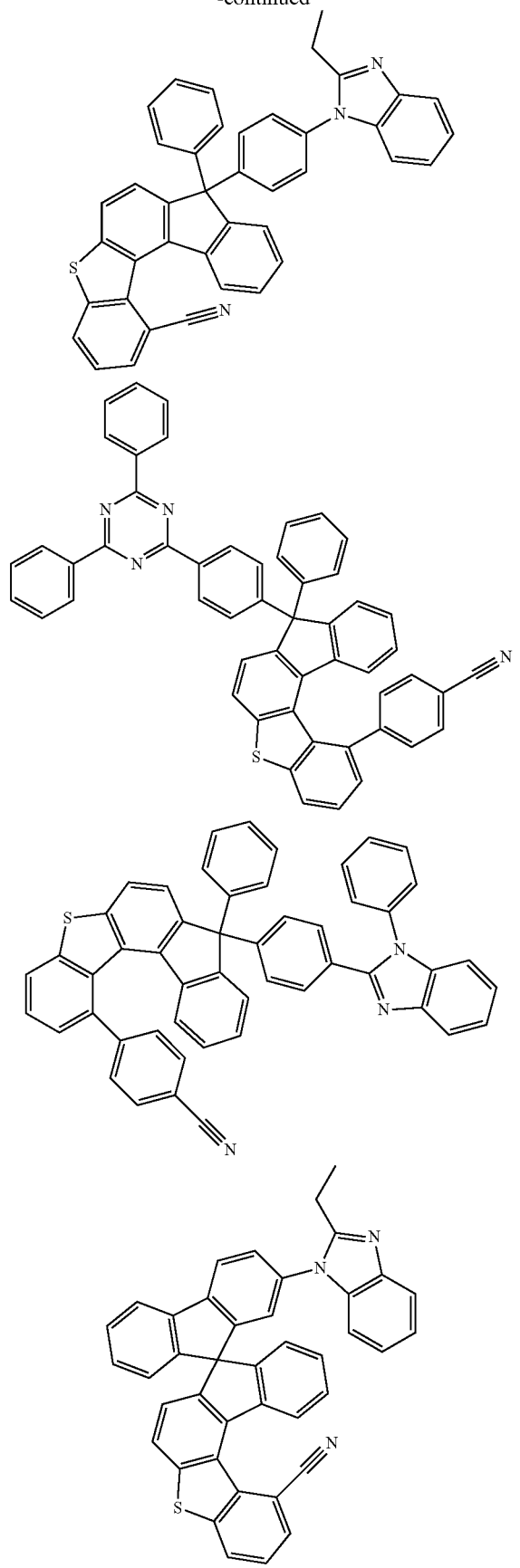
112
-continued
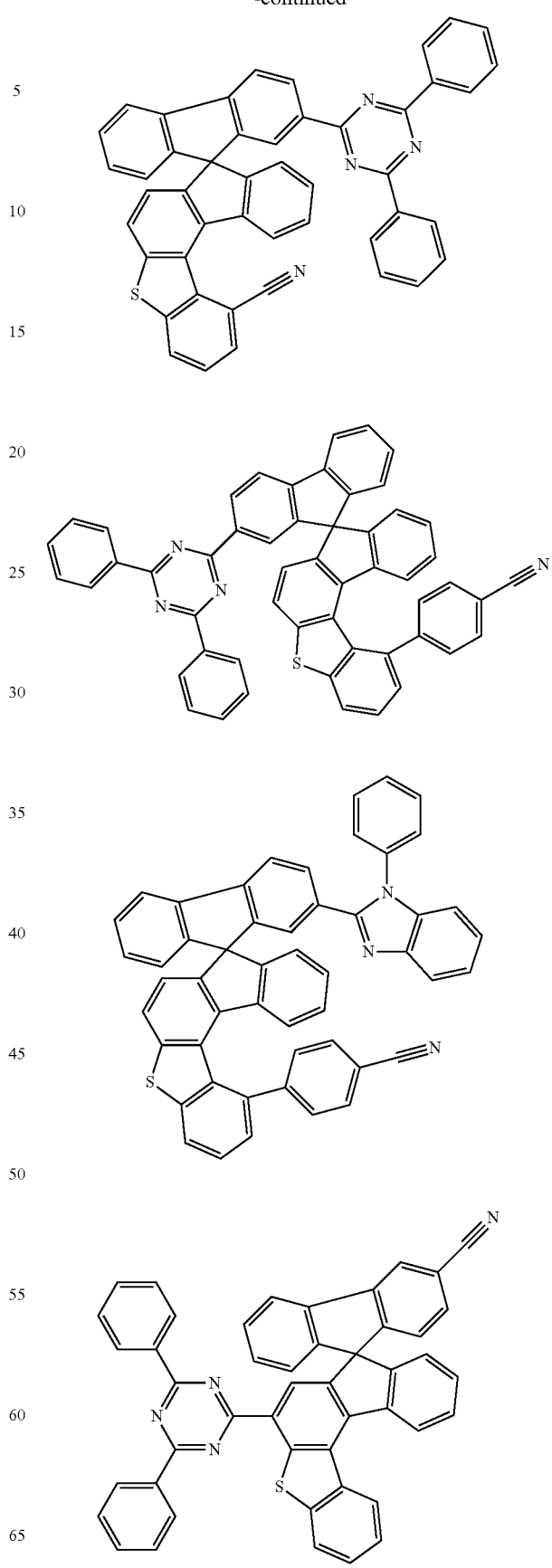

113
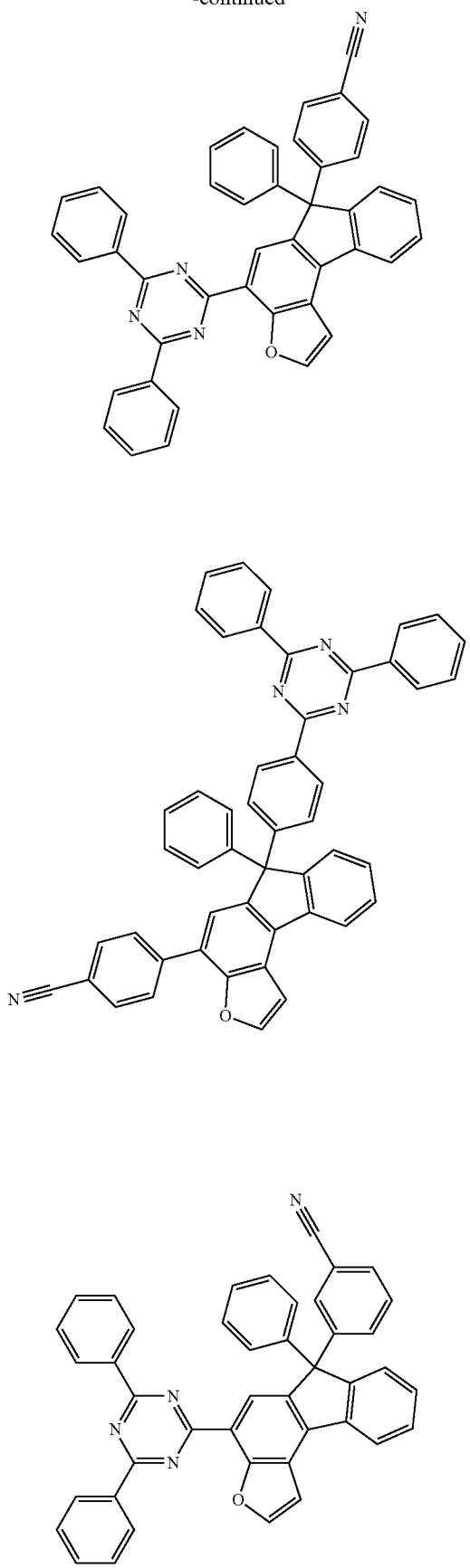
114
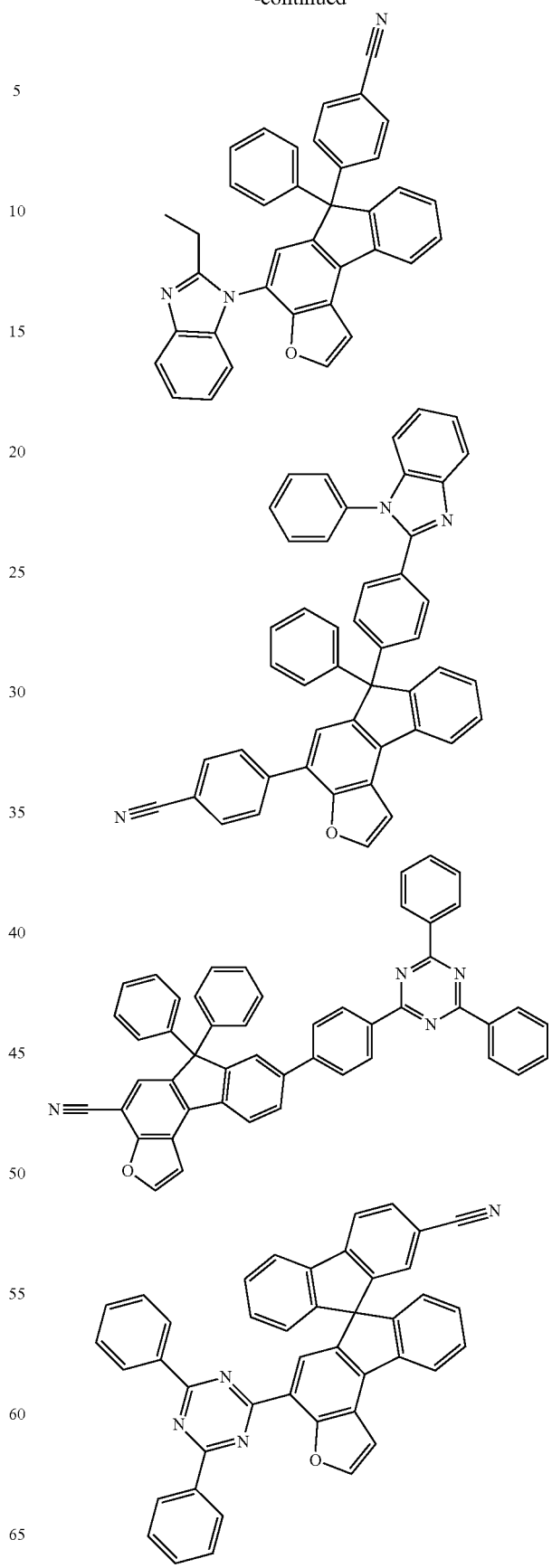

115
-continued
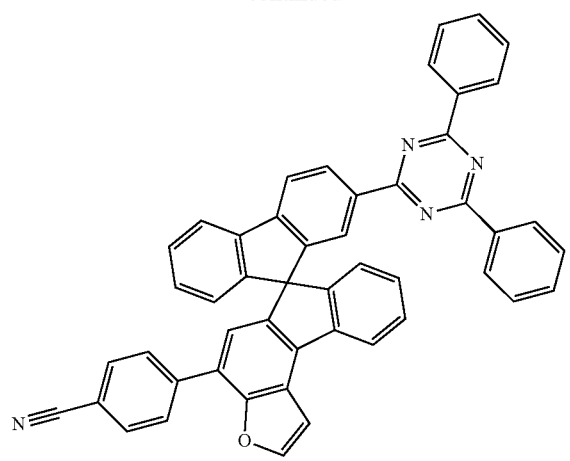
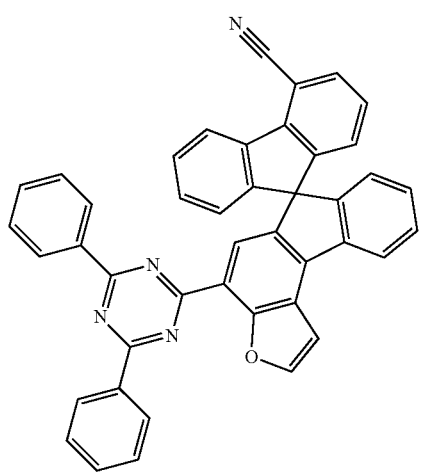
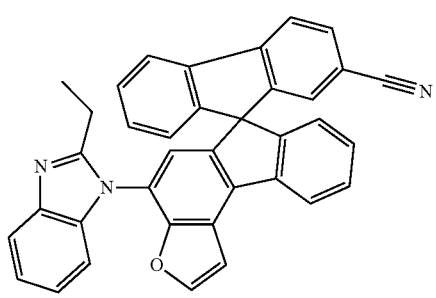
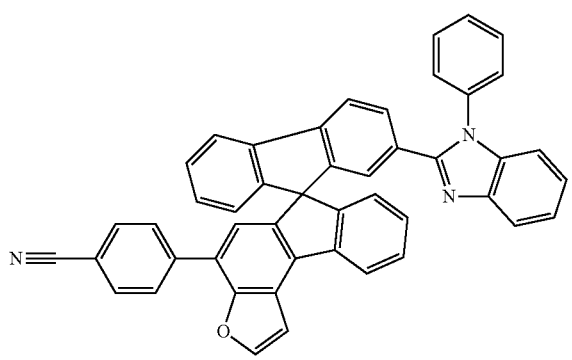
116
-continued
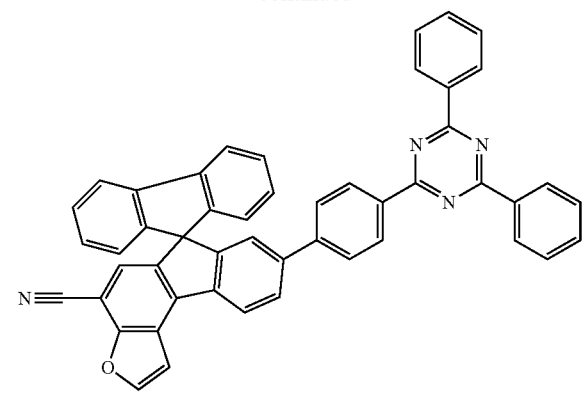
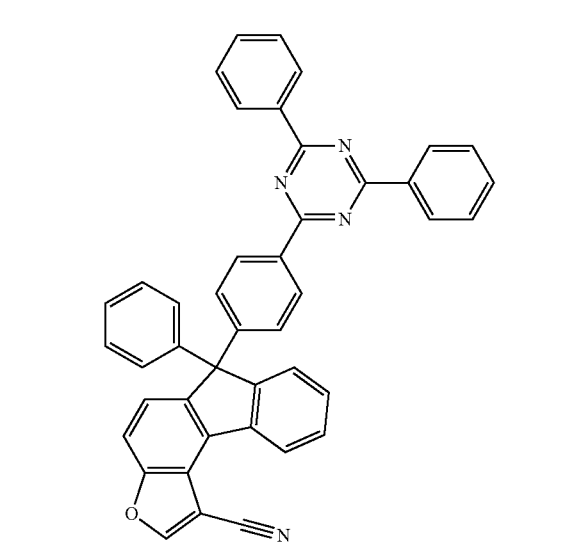
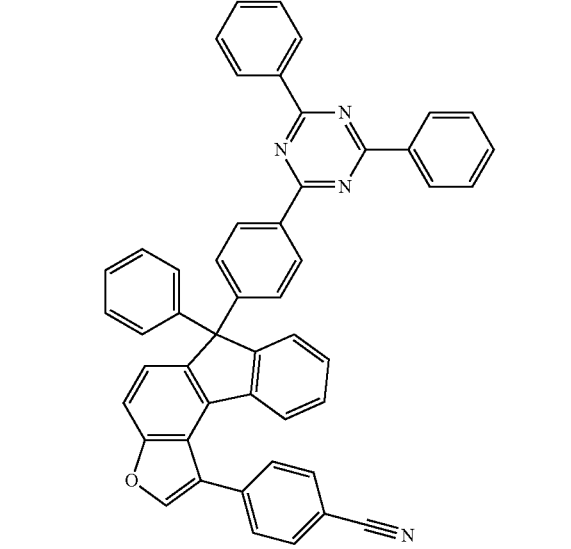

117
-continued
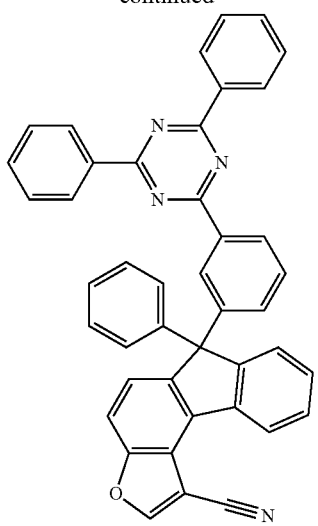
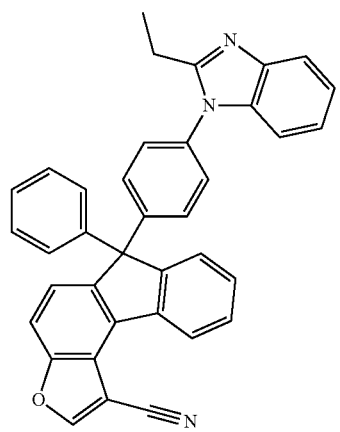
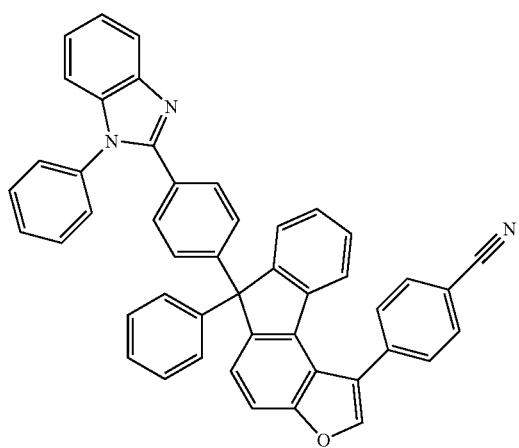
118
-continued
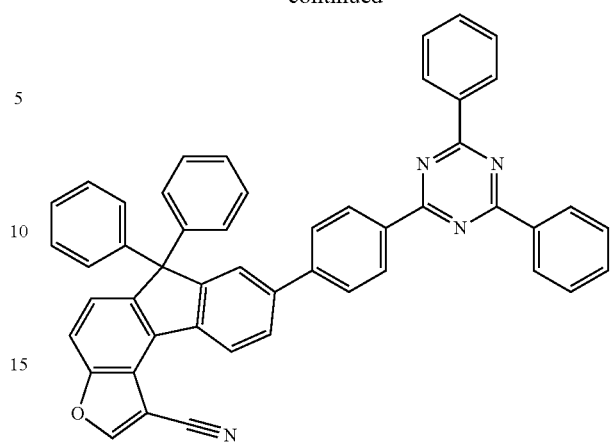
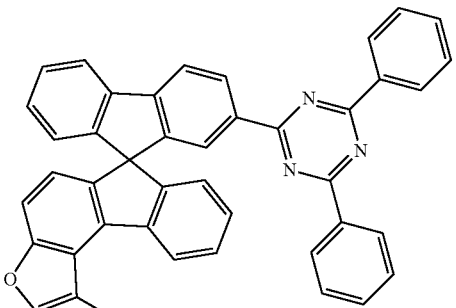
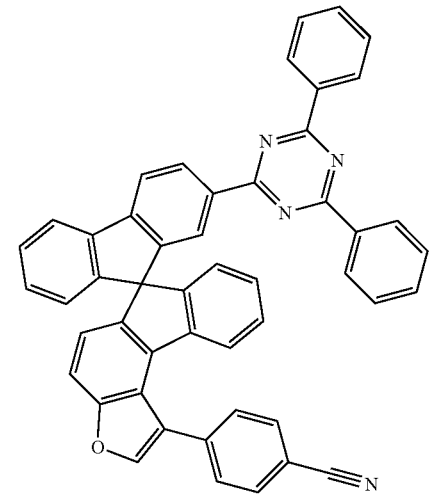

119
-continued
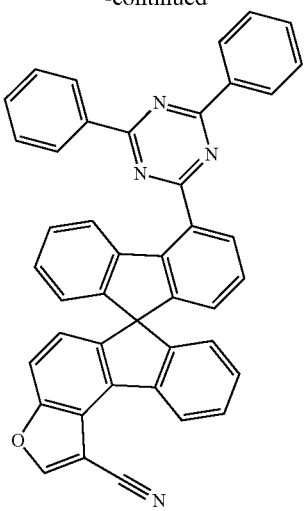
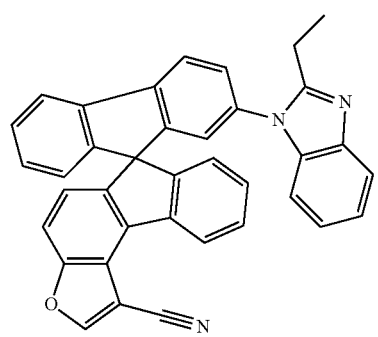
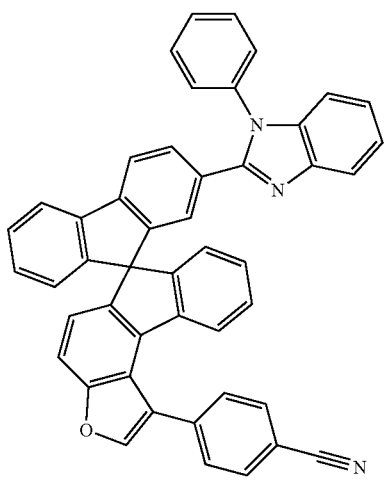
120
-continued
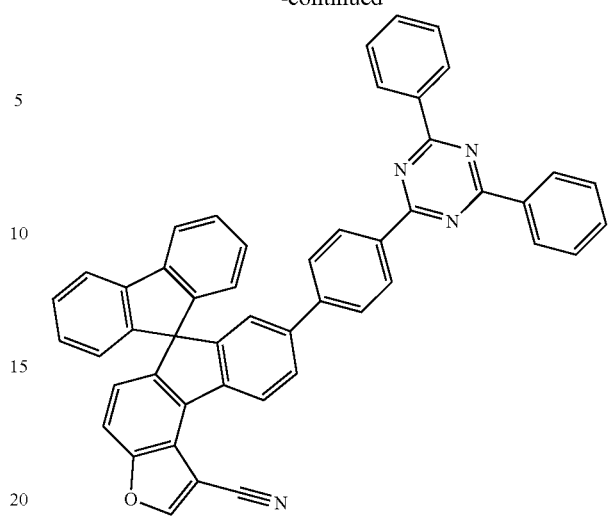
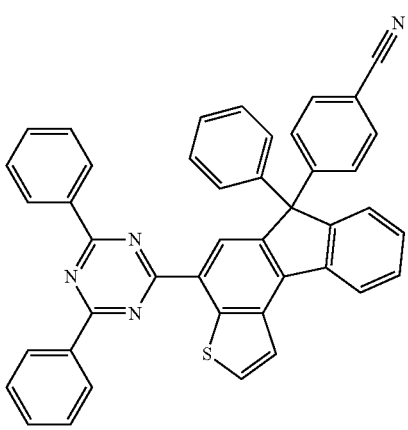
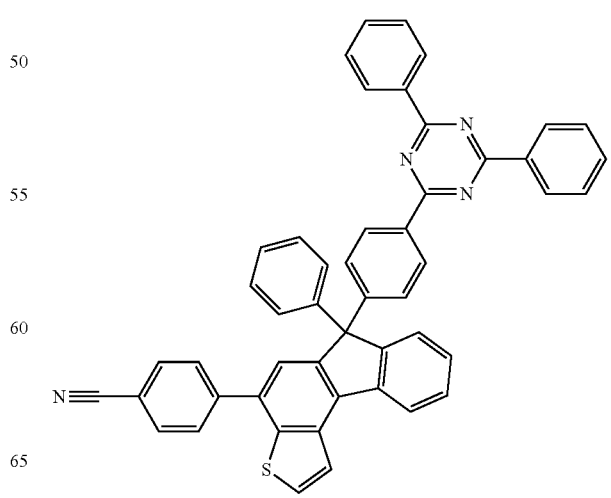

121
-continued
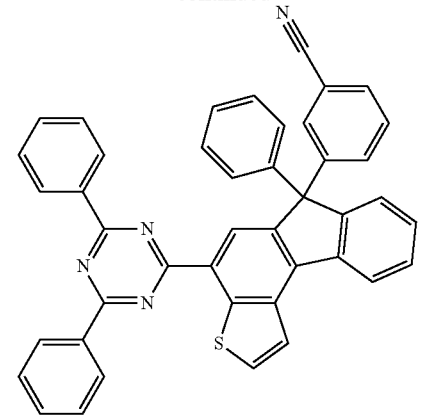
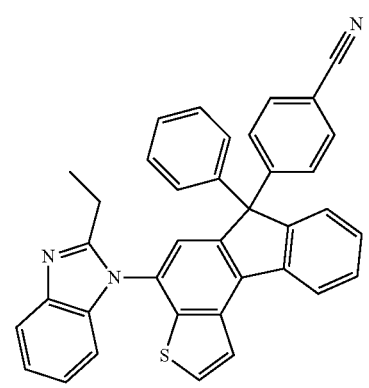
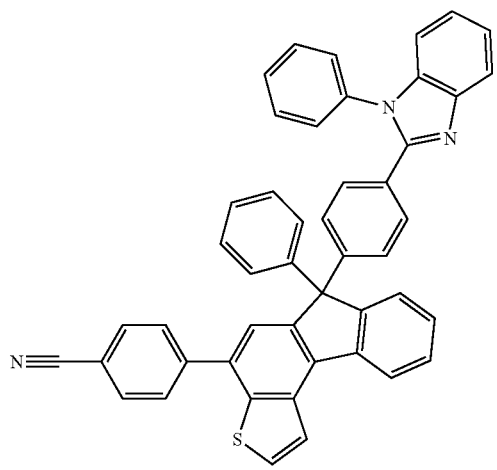
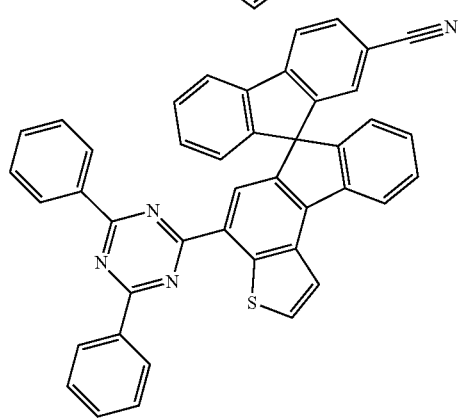
122
-continued
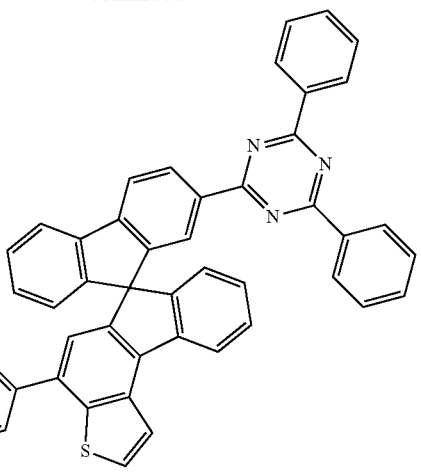
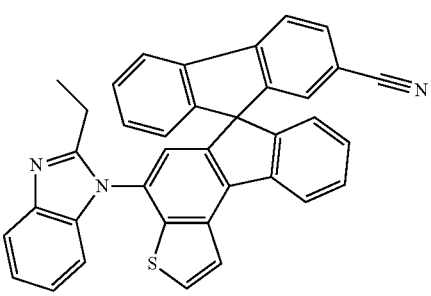
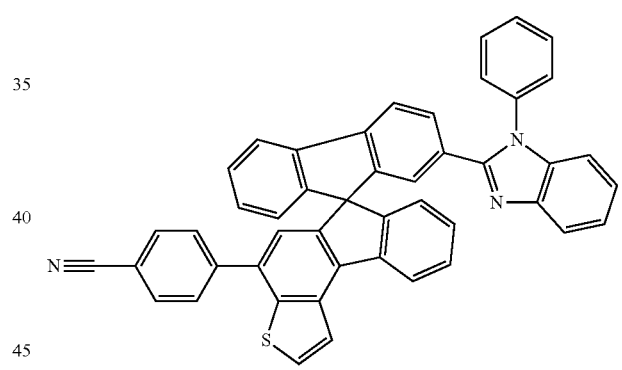
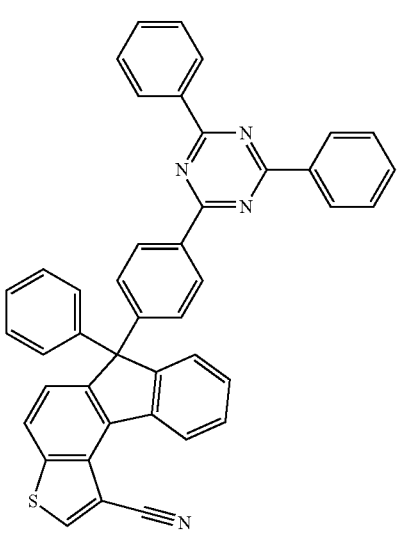

123
-continued
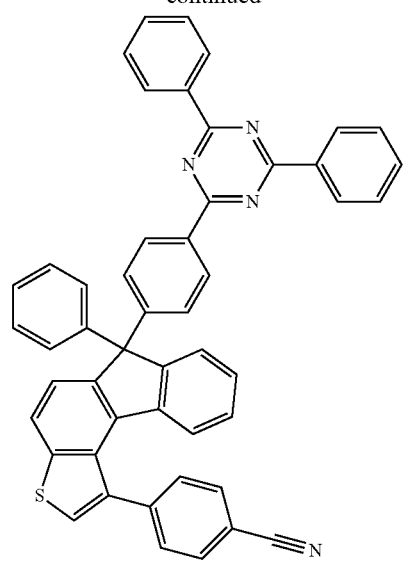
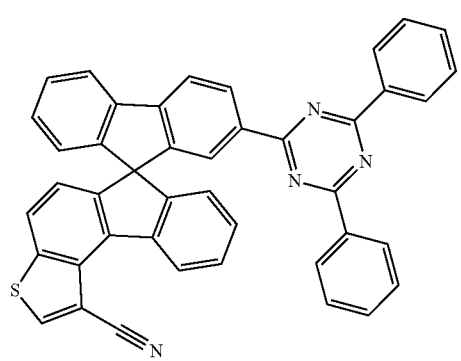
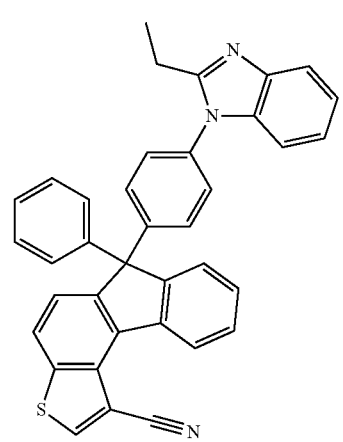
124
-continued
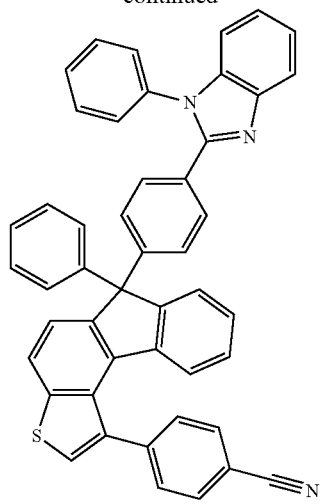
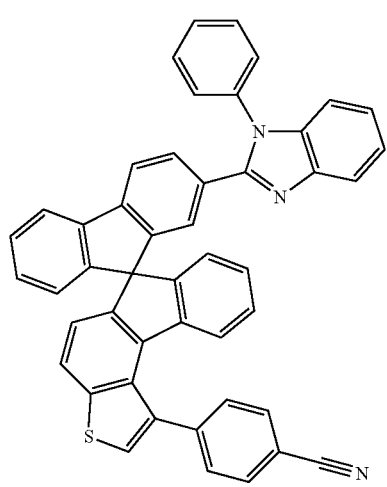
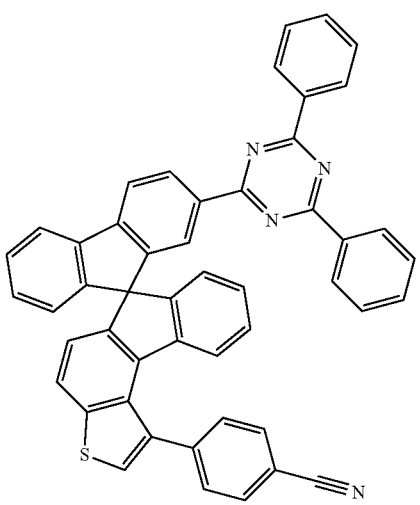

-continued
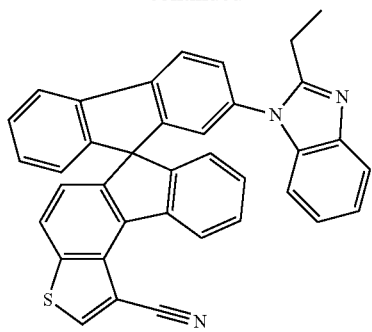
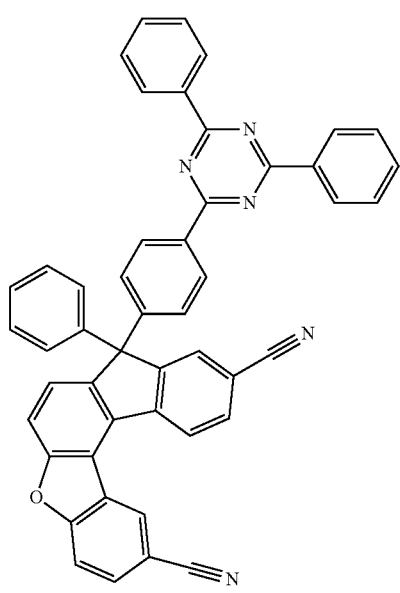
-continued
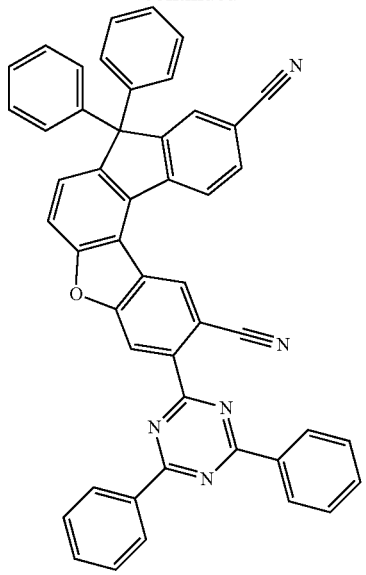
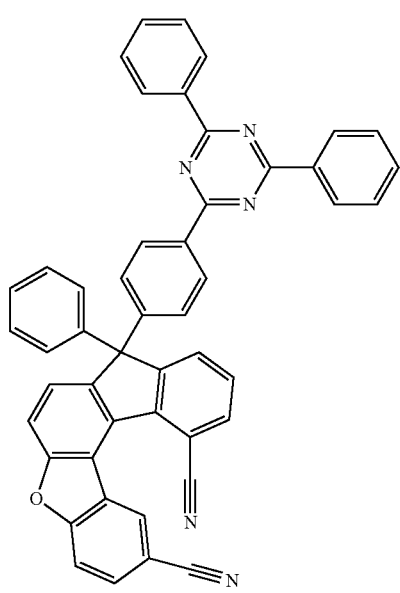
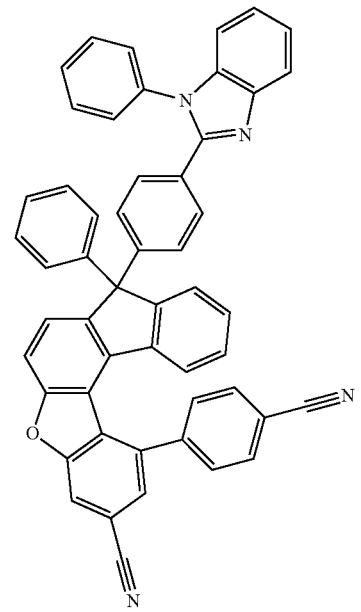

127
-continued
128
-continued
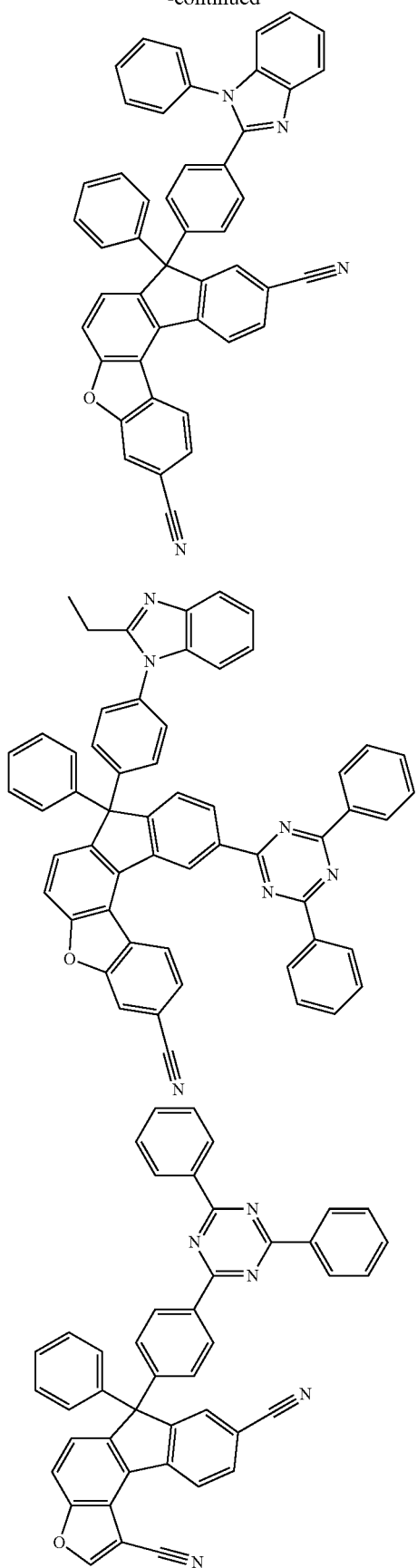
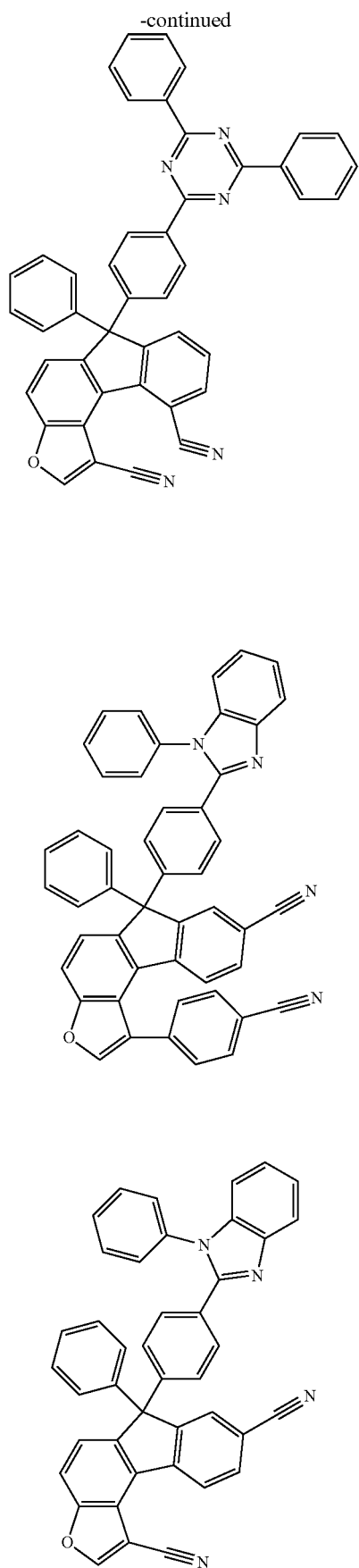

129
-continued
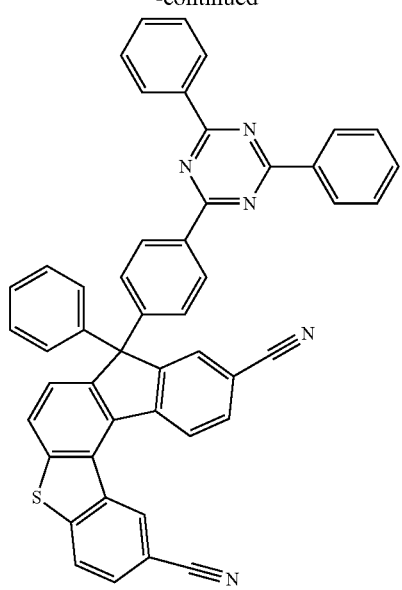
130
-continued
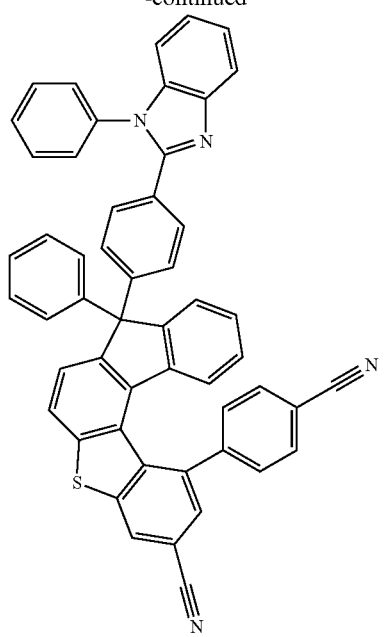
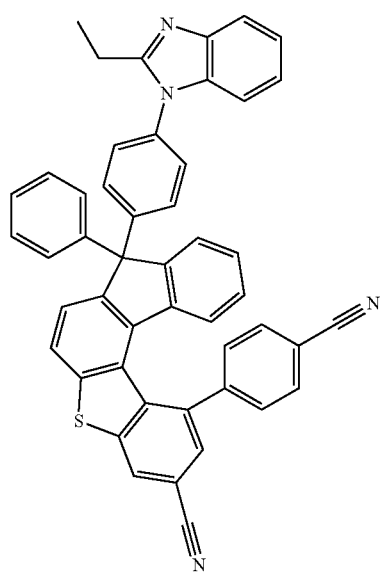
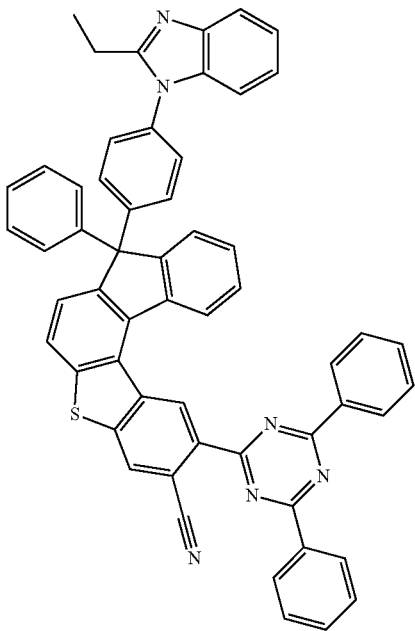

131
-continued
132
-continued
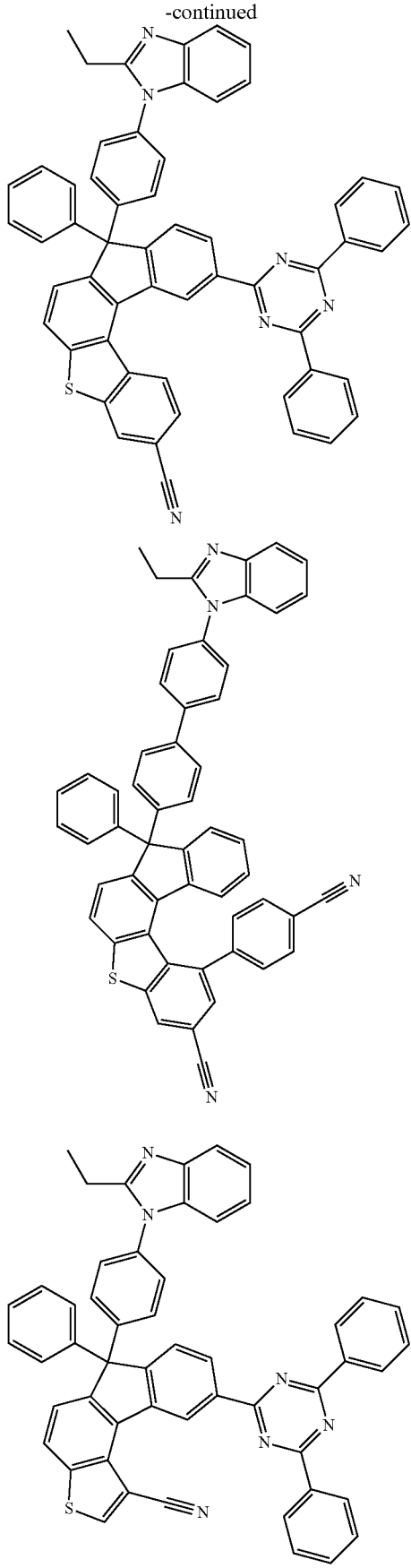
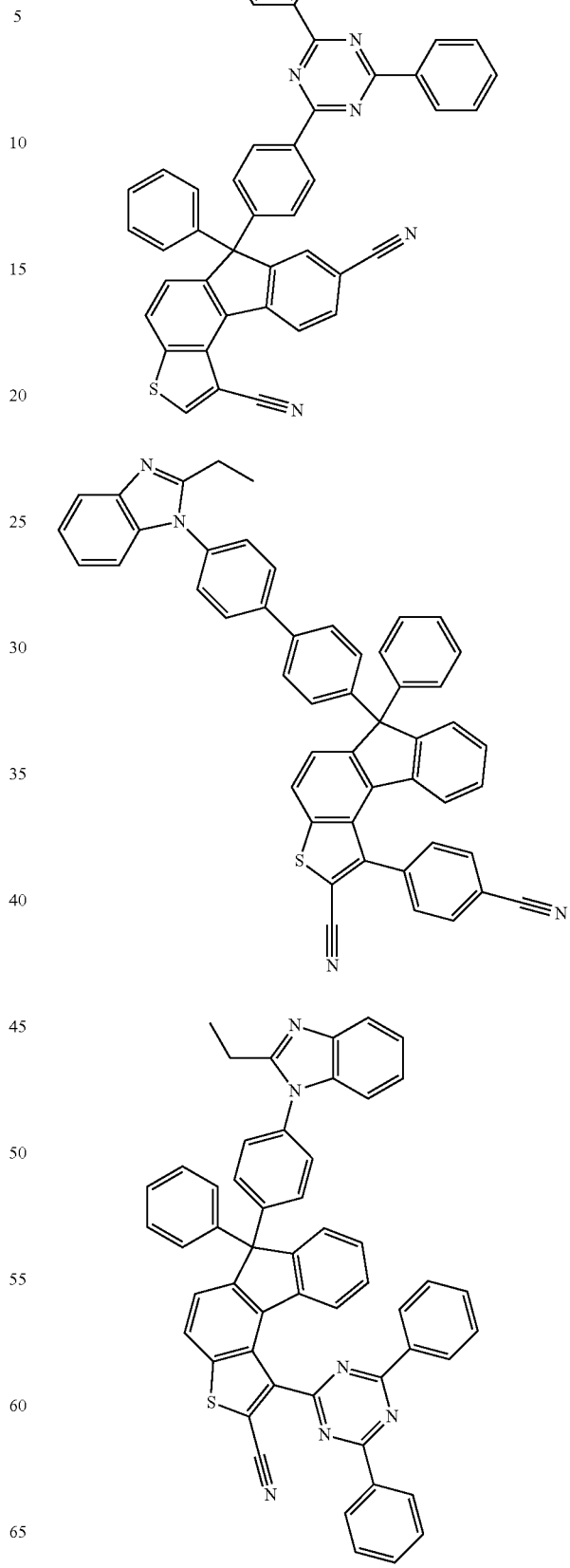

133
-continued
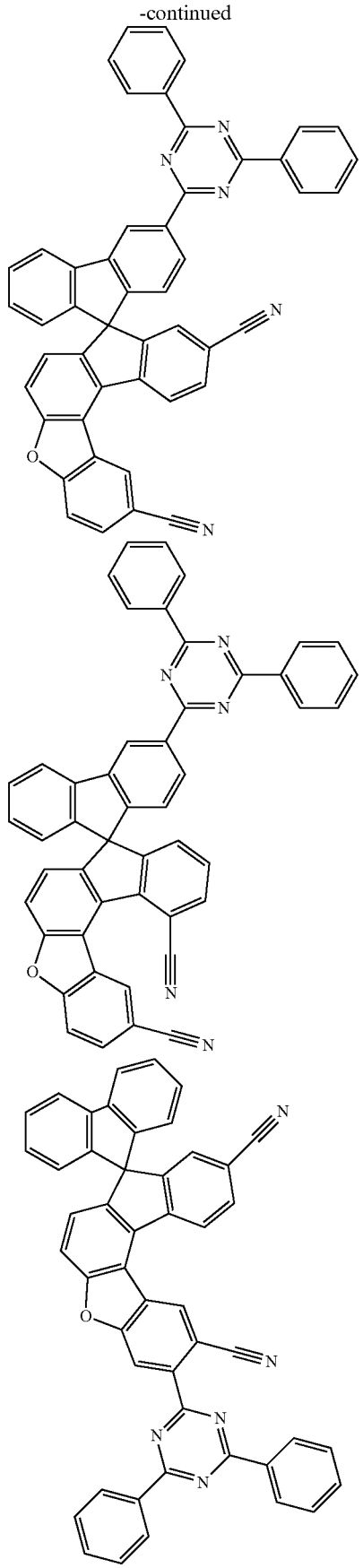
134
-continued

135
-continued
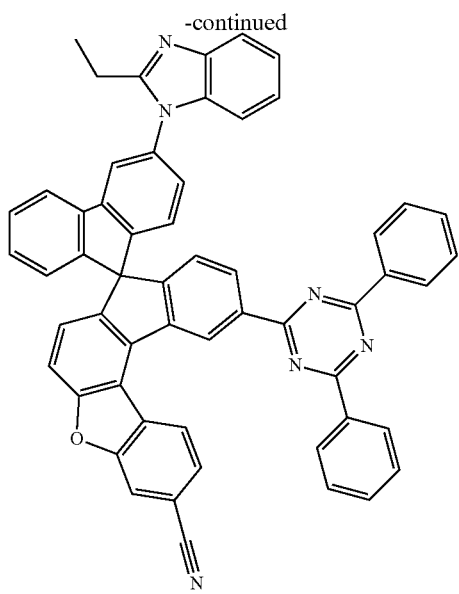
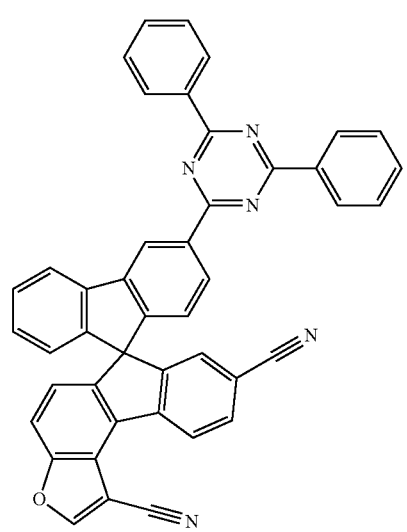
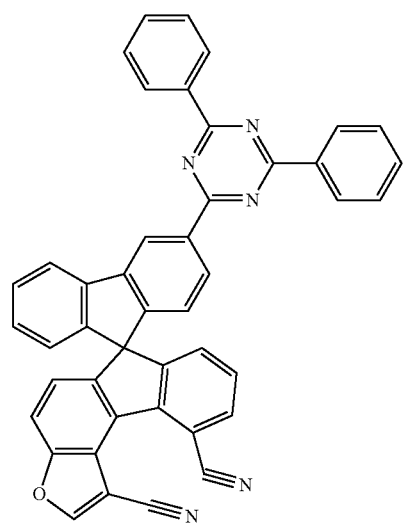
136
-continued
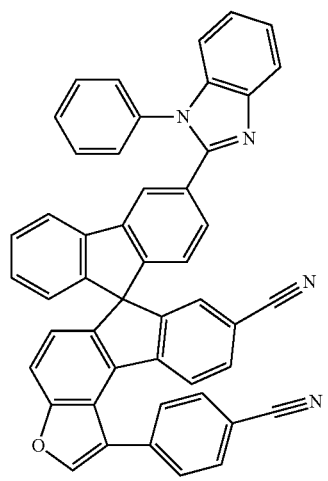
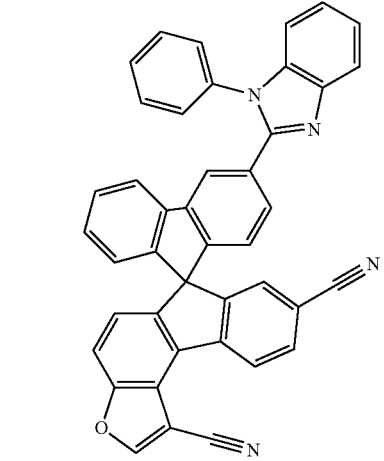 [SMILES: N#Cc1ccc2c(c1)C1(c3ccccc3-c3cc(-c4nc5ccccc5n4-c4ccccc4)ccc31)c1ccc3occ(C#N)c3c1-2]
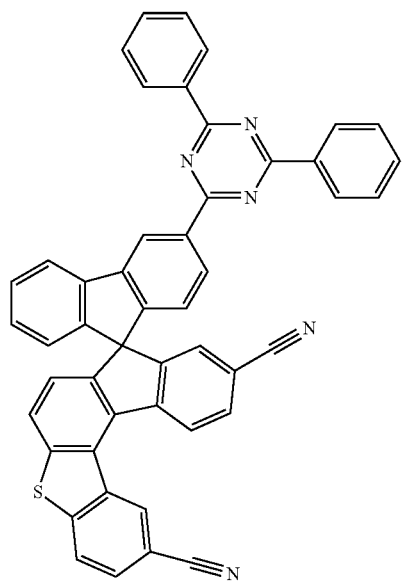

137
-continued
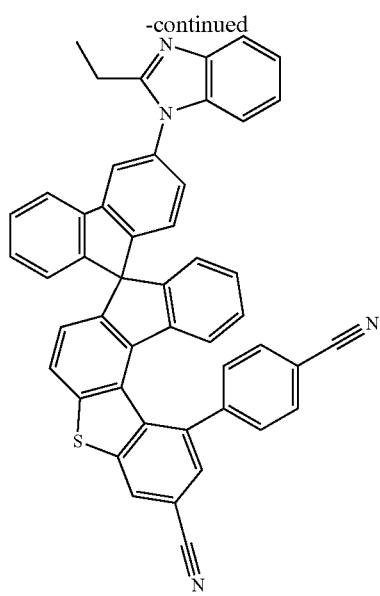
138
-continued
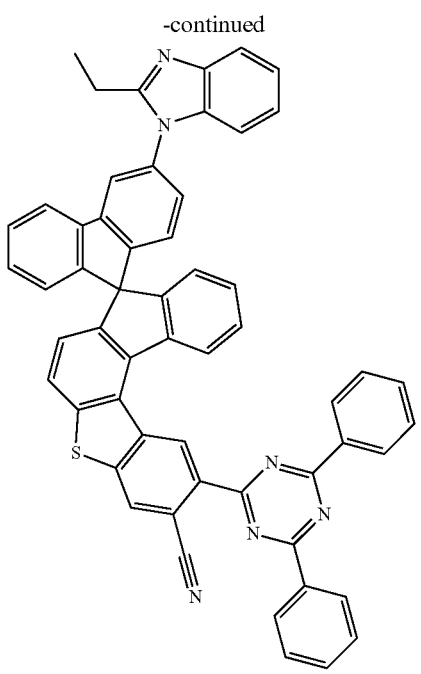
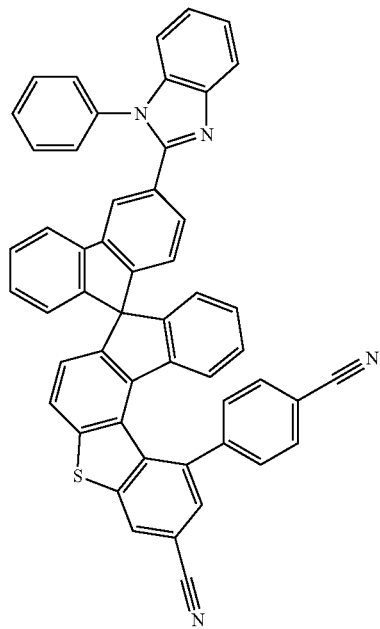
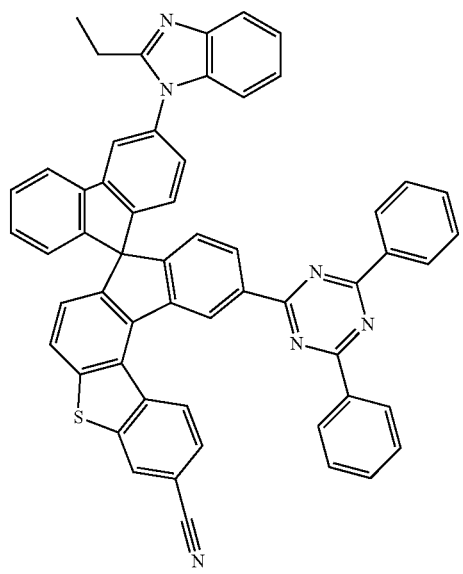

| 139 | 140 |
|---|---|
| -continued | -continued |
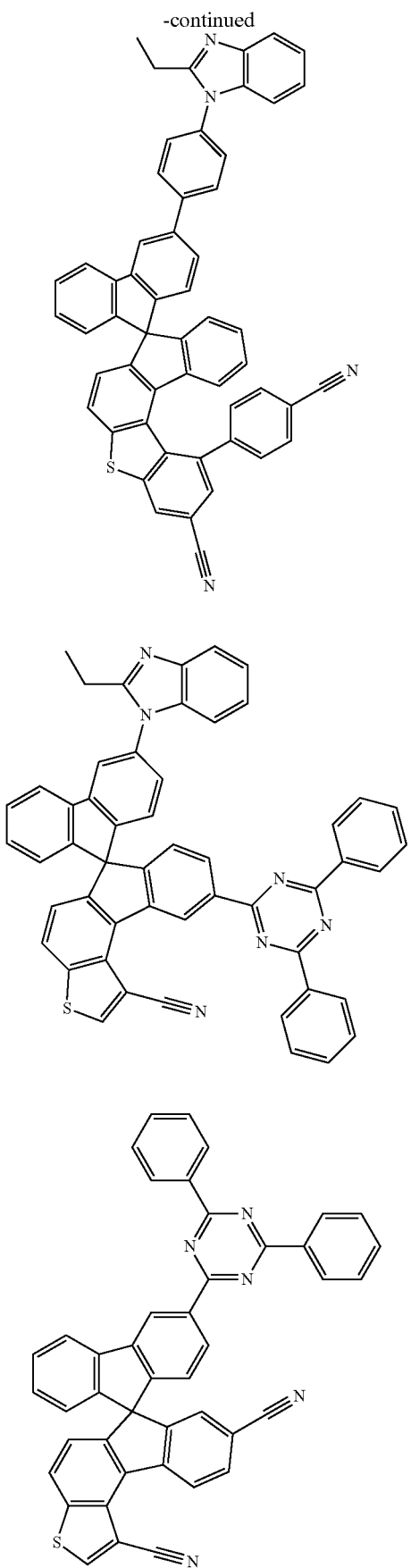
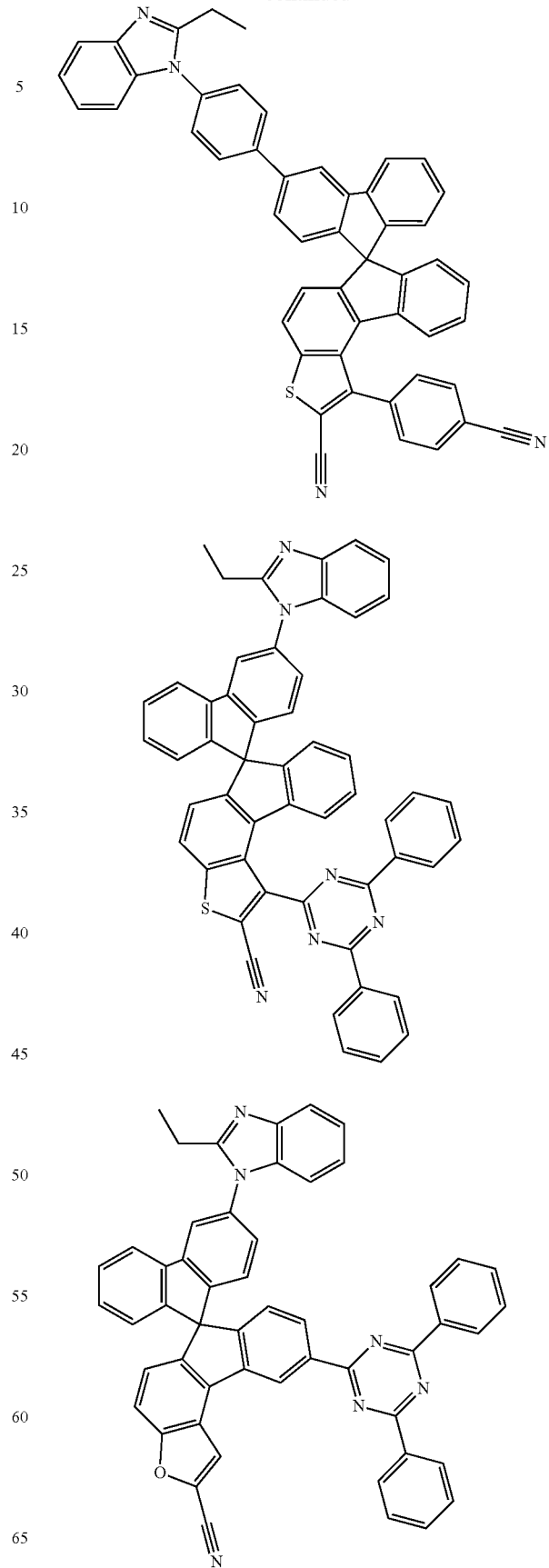

-continued

141

142

143
-continued
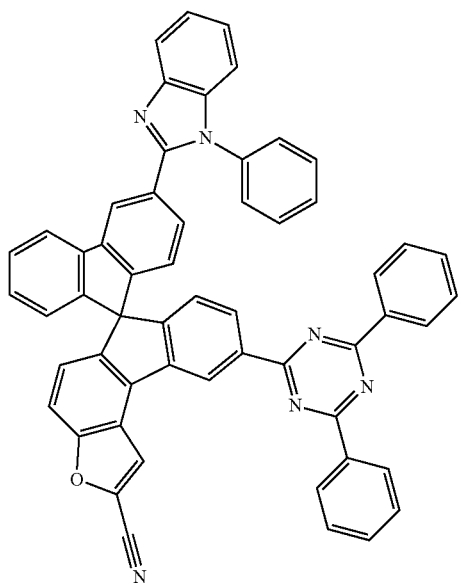
144
-continued
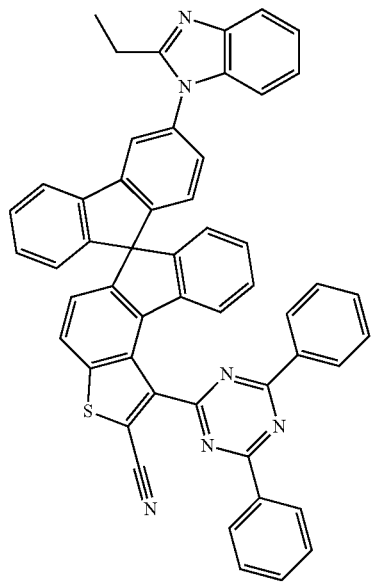
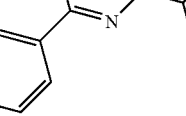

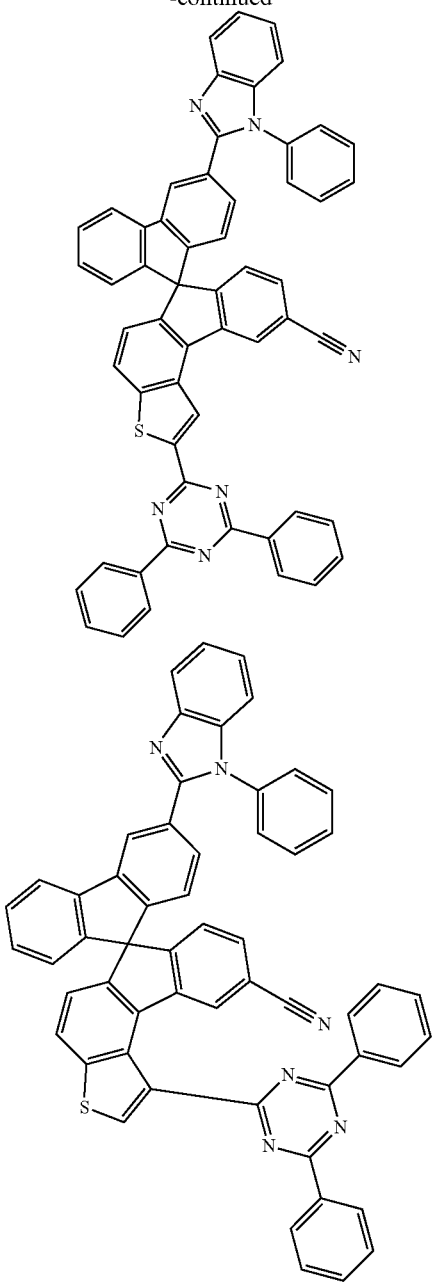

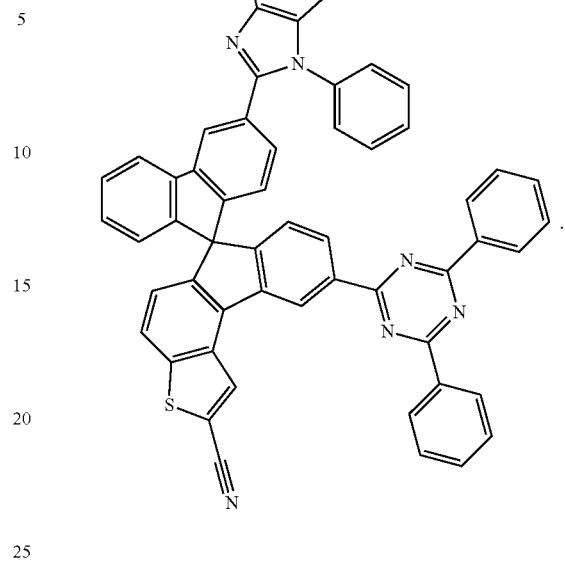

15. An organic light emitting device comprising: a first electrode; a second electrode that is provided to face the first electrode; and one or more organic material layers that are provided between the first electrode and the second electrode, wherein at least one layer of the organic material layers includes the compound according to claim 1.

16. An organic light emitting device comprising: a first electrode; a second electrode that is provided to face the first electrode; and one or more organic material layers that are provided between the first electrode and the second electrode, wherein at least one layer of the organic material layers includes the compound according to claim 14.

* * * * *

UNITED STATES PATENT AND TRADEMARK OFFICE
CERTIFICATE OF CORRECTION

PATENT NO. : 11,980,090 B2
APPLICATION NO. : 17/262114
DATED : May 7, 2024
INVENTOR(S) : Lee et al.

Page 1 of 6

It is certified that error appears in the above-identified patent and that said Letters Patent is hereby corrected as shown below:

In the Claims

In Claim 1, at Column 91, Lines 26-38, the structure of Chemical Formula 1 should be:

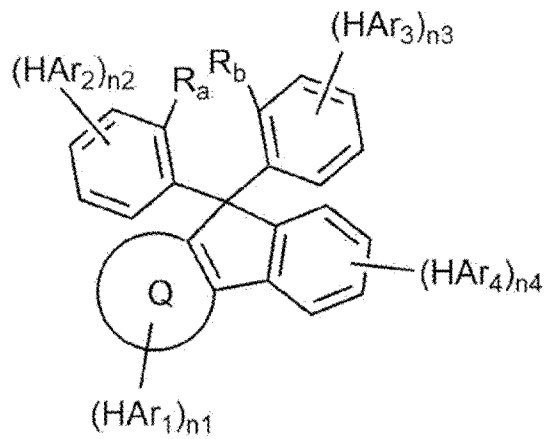

Signed and Sealed this
Ninth Day of July, 2024

Katherine Kelly Vidal
*Director of the United States Patent and Trademark Office*

In Claim 5, at Column 92, Lines 50-66, the structure of Chemical Formula 4-1 should be:
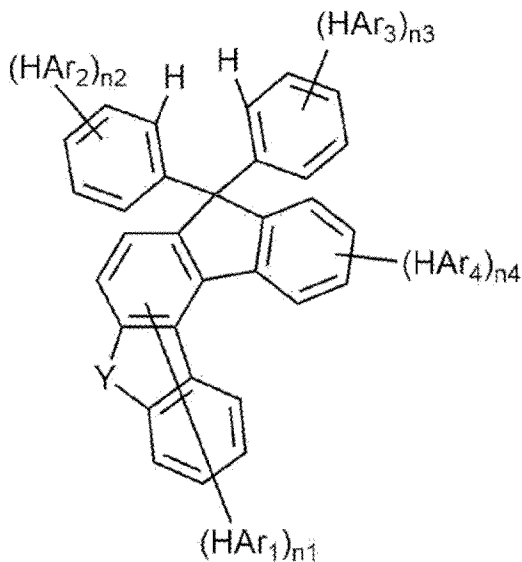
In Claim 5, at Column 93, Lines 1-19, the structure of Chemical Formula 4-2 should be:
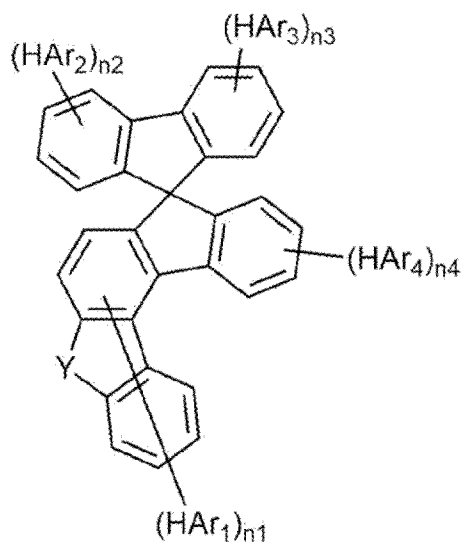

CERTIFICATE OF CORRECTION (continued)
U.S. Pat. No. 11,980,090 B2

In Claim 5, at Column 93, Lines 21-36, the structure of Chemical Formula 4-3 should be:

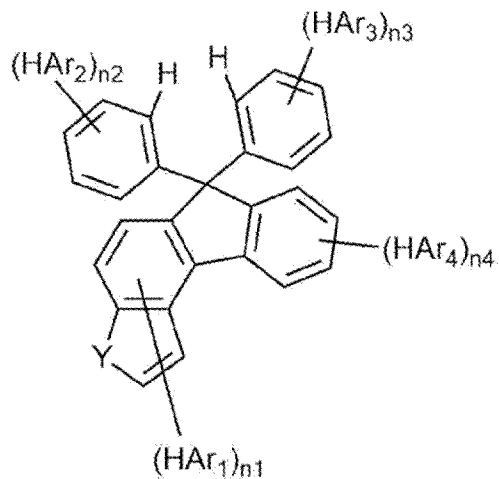

In Claim 5, at Column 93, Lines 38-51, the structure of Chemical Formula 4-4 should be:

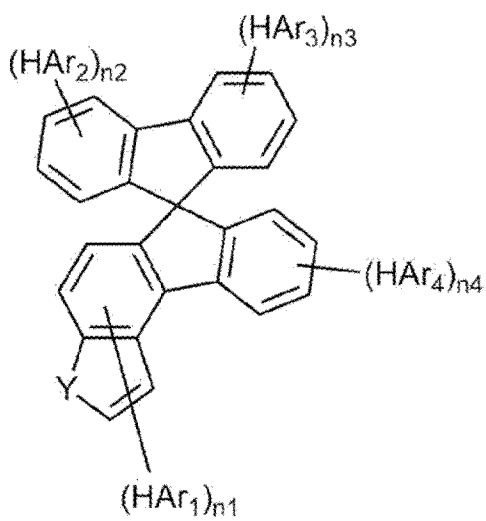

In Claim 9, at Column 94, Lines 53-68, the structure of Chemical Formula 5-3 should be:

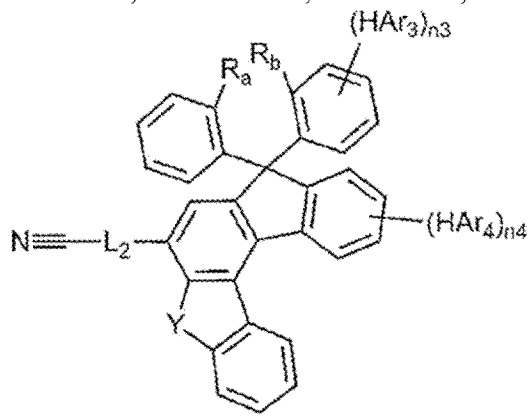

In Claim 9, at Column 95, Lines 3-15, the structure of Chemical Formula 5-4 should be:
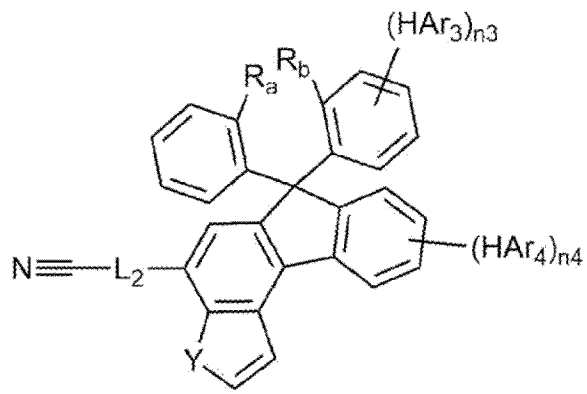
In Claim 10, at Column 95, Lines 30-44, the structure of Chemical Formula 5-5 should be:
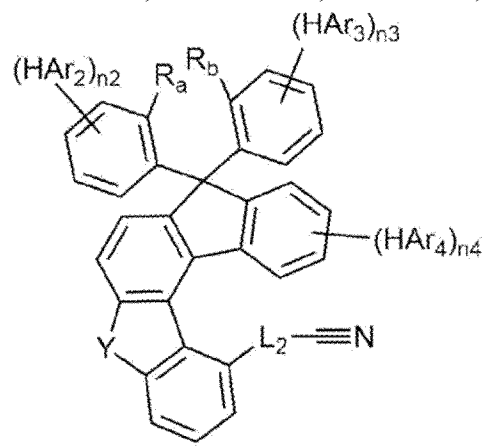
In Claim 10, at Column 95, Lines 46-57, the structure of Chemical Formula 5-6 should be:
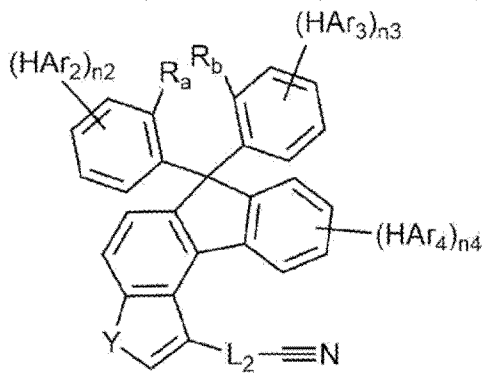

CERTIFICATE OF CORRECTION (continued)
U.S. Pat. No. 11,980,090 B2

In Claim 12, at Column 96, Lines 18-33, the structure of Chemical Formula 6-1 should be:

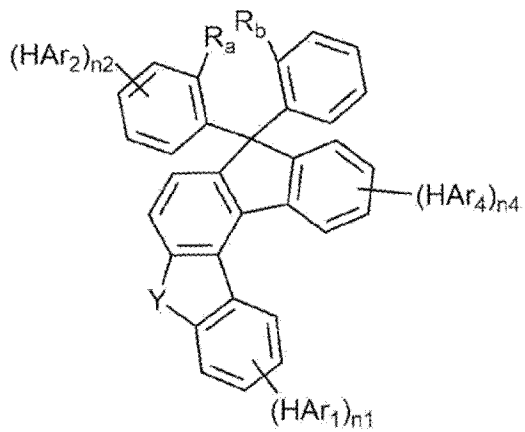

In Claim 12, at Column 96, Lines 39-53, the structure of Chemical Formula 6-2 should be:

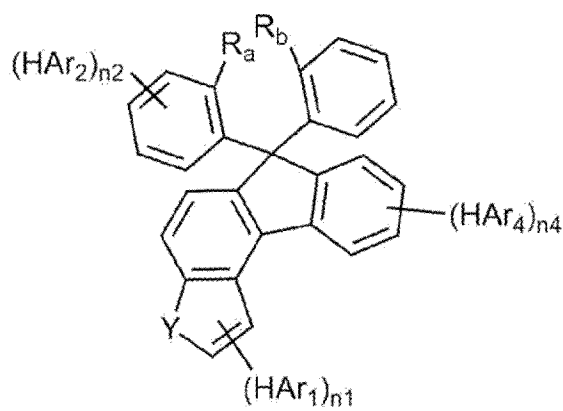

In Claim 13, at Column 97, Lines 3-16, the structure of Chemical Formula 6-3 should be:

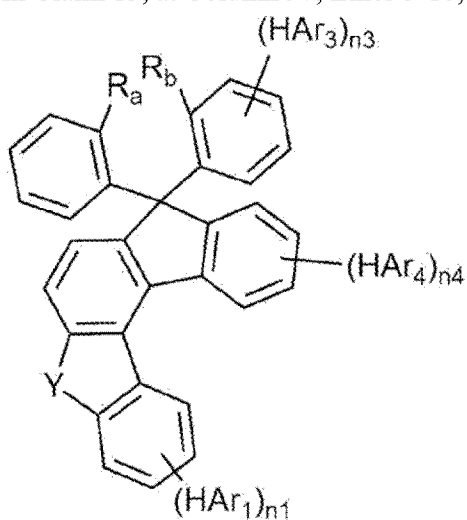

CERTIFICATE OF CORRECTION (continued)
U.S. Pat. No. 11,980,090 B2

In Claim 13, at Column 97, Lines 18-33, the structure of Chemical Formula 6-4 should be: